US006362341B1

(12) United States Patent
Thorsett et al.

(10) Patent No.: US 6,362,341 B1
(45) Date of Patent: Mar. 26, 2002

(54) BENZYL COMPOUNDS WHICH INHIBIT LEUKOCYTE ADHESION MEDIATED BY VLA-4

(75) Inventors: Eugene D. Thorsett, Moss Beach; Christopher M. Semko, Fremont; Michael A. Pleiss, Sunnyvale, all of CA (US); Louis John Lombardo, Belle Meade, NJ (US); Andrei W. Konradi; Francine S. Grant, both of San Francisco, CA (US); Darren B. Dressen, San Mateo, CA (US); Michael S. Dappen, Redwood City, CA (US)

(73) Assignees: Athena Neurosciences, Inc., So. San Francisco, CA (US); American Home Products, Madison, NJ (US)

( * ) Notice: Subject to any disclaimer, the term of this patent is extended or adjusted under 35 U.S.C. 154(b) by 0 days.

(21) Appl. No.: 09/127,601

(22) Filed: Jul. 31, 1998

Related U.S. Application Data

(60) Provisional application No. 60/112,007, filed on Jul. 31, 1997, now abandoned.

(51) Int. Cl.[7] .................. C07D 277/04; A61K 31/426
(52) U.S. Cl. .................. 548/200; 514/227.5; 514/300; 514/365; 514/423; 544/59; 546/225
(58) Field of Search ................. 548/200, 537; 514/365, 330, 227.5, 423; 544/59; 546/225

(56) References Cited

U.S. PATENT DOCUMENTS

| | | |
|---|---|---|
| 4,018,913 A | 4/1977 | Okamoto et al. |
| 4,018,915 A | 4/1977 | Okamoto et al. |
| 4,036,955 A | 7/1977 | Okamoto et al. |
| 4,041,156 A | 8/1977 | Okamoto et al. |
| 4,046,876 A | 9/1977 | Okamoto et al. |
| 4,055,636 A | 10/1977 | Okamoto et al. |
| 4,055,651 A | 10/1977 | Okamoto et al. |
| 4,069,318 A | 1/1978 | Okamoto et al. |
| 4,070,457 A | 1/1978 | Okamoto et al. |
| 4,071,621 A | 1/1978 | Okamoto et al. |
| 4,073,914 A | 2/1978 | Kikumoto et al. |
| 4,074,057 A | 2/1978 | Kawamatsu et al. |
| 4,096,255 A | 6/1978 | Kikumoto et al. |
| 4,097,591 A | 6/1978 | Okamoto et al. |
| 4,104,392 A | 8/1978 | Okamoto et al. |
| 4,804,676 A | 2/1989 | Inaoka et al. |
| 4,910,190 A | 3/1990 | Bergeson et al. |

(List continued on next page.)

FOREIGN PATENT DOCUMENTS

| | | |
|---|---|---|
| AU | 6147073 | 4/1975 |
| DE | 2357334 A | 6/1974 |
| DE | 2655636 A | 6/1977 |
| EP | 0526348 A | 2/1993 |
| GB | 9711143.9 | 5/1997 |
| GB | 971431.3 | 7/1997 |
| GB | 9714316.8 | 7/1997 |
| GB | 9714335.8 | 7/1997 |
| GB | 9722674.0 | 10/1997 |
| GB | 9800680.2 | 1/1998 |
| GB | 9800684.4 | 1/1998 |
| GB | 9800686.9 | 1/1998 |
| JP | 01454732 | 5/1992 |
| JP | 04154732 A | 5/1992 |
| JP | 6-16625 | 1/1994 |
| JP | 08073422 A | 3/1996 |
| WO | WO 92/16549 | 10/1992 |
| WO | WO 94/07815 | 4/1994 |
| WO | WO 94/12181 | 6/1994 |
| WO | WO 95/15973 | 6/1995 |
| WO | WO 96/20725 | 7/1996 |
| WO | WO 96/20949 | 7/1996 |
| WO | WO 96/22966 | 8/1996 |

(List continued on next page.)

OTHER PUBLICATIONS

V. Simanis et al., *Int. J. Pept. Protein Res.* (1982), 19(1), 67–70.

D. Leibfritz et al., *Tetrahedron* (1982),38(14), 2165–81.

A.M. El–Nagger et al., *Acta. Pharm. Jugosl.* (1985), 35 (1), 15–22.

Chemical Abstract No. 126040, vol. 74, No. 23 (Jun. 7, 1971).

Chemical Abstract No. 176262, vol. 99, No. 21 (Nov. 21, 1983).

Chemical Abstract No. 210288, vol. 106, No. 25 (Jun. 22, 1987).

Chemical Abstract No. 167952, vol. 108, No. 19 (May 9, 1988).

Chemical Abstract No. 34164, vol. 125, No. 3 (Jul. 15, 1996).

Engelman, V.W., et al. "Cell Adhesion Integrins as Pharmaceutical Targets." *Ann. Reports in Med. Chem.* 31: 191–200 (1996).

Gamo, K. "Optical resolution of racemic amine derivatives." *Chem. Abs.* 117: 211689 (1992).

Hauptmanh, J., et al. "Degradation of Benzamidine–Type Synthetic Inhibitor of Coagulation Enzymes in Plasma of Various Species." *Thrombosis Research.* 61: 279–284 (1991).

(List continued on next page.)

*Primary Examiner*—Shailendra Kumar
(74) *Attorney, Agent, or Firm*—Burns, Doane, Swecker & Mathis LLP

(57) ABSTRACT

Disclosed are compounds which bind VLA-4. Certain of these compounds also inhibit leukocyte adhesion and, in particular, leukocyte adhesion mediated by VLA-4. Such compounds are useful in the treatment of inflammatory diseases in a mammalian patient, e.g., human, wherein the disease may be, for example, asthma, Alzheimer's disease, atherosclerosis, AIDS dementia, diabetes, inflammatory bowel disease, rheumatoid arthritis, tissue transplantation, tumor metastasis and myocardial ischemia. The compounds can also be administered for the treatment of inflammatory brain diseases such as multiple sclerosis.

18 Claims, No Drawings

U.S. PATENT DOCUMENTS

| | | |
|---|---|---|
| 4,977,168 A | 12/1990 | Bernat et al. |
| 4,981,873 A | 1/1991 | Witte et al. |
| 5,338,755 A | 8/1994 | Wagnon et al. |
| 5,362,902 A | 11/1994 | Barnish et al. |
| 5,397,801 A | 3/1995 | Wagnon et al. |
| 5,481,005 A | 1/1996 | Wagnon et al. |
| 5,578,633 A | 11/1996 | Wagnon et al. |
| 5,650,428 A | 7/1997 | Ohmori et al. |
| 5,686,628 A | 11/1997 | Veale et al. |
| 6,122,888 A1 | 4/2001 | Durette et al. |

FOREIGN PATENT DOCUMENTS

| | | |
|---|---|---|
| WO | WO 97/03094 | 1/1997 |
| WO | WO 98/04247 | 2/1998 |
| WO | WO 98/42656 | 10/1998 |
| WO | WO 98/53814 | 12/1998 |
| WO | WO 98/53817 | 12/1998 |
| WO | WO 98/53818 | 12/1998 |
| WO | WO 98/54207 | 12/1998 |
| WO | WO 98/58902 | 12/1998 |
| WO | WO 99/10312 | 3/1999 |
| WO | WO 99/10313 | 3/1999 |

OTHER PUBLICATIONS

Leibfritz, D., et al. "Synthese Von 2–Methylalanin–Peptiden, Die pH–Abhangigkeit Ihrer 13C–NMR–Spektren Und Eine Neue Methode Zur Auswetung Uber CS–Diagramme." *Tetrahedron.* 18(14): 2165–2181 (1982). (Translation enclosed).

Voigt, B., et al. "Synthese von Nα–(Arylsulfonyl–L–prolyl)–und Nα–Benzyloxycarbonyl–L–prolyl)–D, L–4–amidinophenyl–alaninamiden als Throbininhibitoren." *Pharmazie.* 41: 233–235 (1986).

BENZYL COMPOUNDS WHICH INHIBIT LEUKOCYTE ADHESION MEDIATED BY VLA-4

CROSS-REFERENCE TO RELATED APPLICATIONS

This application claims the benefit of U.S. Provisional Application No. 60/112,007, now abandoned, filed on Jul. 31, 1997, which was converted pursuant to 37 C.F.R. §1.53(c)(2)(i) from U.S. patent application Ser. No. 08/903, 585, filed Jul. 31, 1997, which application is incorporated herein by reference in its entirety.

BACKGROUND OF THE INVENTION

1. Field of the Invention

This invention relates to compounds which inhibit leukocyte adhesion and, in particular, leukocyte adhesion mediated by VLA-4.

REFERENCES

The following publications, patents and patent applications are cited in this publication as superscript numbers:
1 Hemler and Takada, European Patent Application Publication No. 330,506, published Aug. 30, 1989
2 Elices, et al., *Cell,* 60:577–584 (1990)
3 Springer, *Nature,* 346:425–434 (1990)
4 Osborn, *Cell,* 62:3–6 (1990)
5 Vedder, et al., *Surgery,* 106:509 (1989)
6 Pretolani, et al., *J. Exp. Med.,* 180:795 (1994)
7 Abraham, et al., *J. Clin. Invest.,* 93:776 (1994)
8 Mulligan, et al., *J. Immunology,* 150:2407 (1993)
9 Cybulsky, et al., *Science,* 25:788 (1991)
10 Li, et al., *Arterioscler. Thromb.,* 13:197 (1993)
11 Sasseville, et al., *Am. J. Path.,* 144:27 (1994)
12 Yang, et al., *Proc. Nat. Acad. Science (USA),* 90:10494 (1993)
13 Burkly, et al., *Diabetes,* 43:529 (1994)
14 Baron, et al., *J. Clin. Invest.,* 93:1700 (1994)
15 Hamann, et al., *J. Immunology,* 152:3238 (1994)
16 Yednock, et al., *Nature,* 356:63 (1992)
17 Baron, et al., *J. Exp. Med.,* 177:57 (1993)
18 van Dinther-Janssen, et al., *J. Immunology,* 147:4207 (1991)
19 van Dinther-Janssen, et al., *Annals. Rheumatic Dis.,* 52:672 (1993)
20 Elices, et al., *J. Clin. Invest.,* 93:405 (1994)
21 Postigo, et al., *J. Clin. Invest.,* 89:1445 (1991)
22 Paul, et al., *Transpl. Proceed.,* 25:813 (1993)
23 Okarhara, et al., *Can. Res.,* 54:3233 (1994)
24 Paavonen, et al., *Int. J. Can.,* 58:298 (1994)
25 Schadendorf, et al., *J. Path.,* 170:429 (1993)
26 Bao, et al., *Diff.,* 52:239 (1993)
27 Lauri, et al., *British J. Cancer,* 68:862 (1993)
28 Kawaguchi, et al., *Japanese J. Cancer Res.,* 83:1304 (1992)
29 Kogan, et al., U.S. Pat. No. 5,510,332, issued Apr. 23, 1996
30 International Patent Appl. Publication No. WO 96/01644

All of the above publications, patents and patent applications are herein incorporated by reference in their entirety to the same extent as if each individual publication, patent or patent application was specifically and individually indicated to be incorporated by reference in its entirety.

2. State of the Art

VLA-4 (also referred to as α4β1 integrin and CD49d/CD29), first identified by Hemler and Takada[1], is a member of the β1 integrin family of cell surface receptors, each of which comprises two subunits, an α chain and a β chain. VLA-4 contains an α4 chain and a β1 chain. There are at least nine β1 integrins, all sharing the same β1 chain and each having a distinct α chain. These nine receptors all bind a different complement of the various cell matrix molecules, such as fibronectin, laminin, and collagen. VLA-4, for example, binds to fibronectin. VLA-4 is unique among $\beta_1$ integrins in that it also binds non-matrix molecules that are expressed by endothelial and other cells. These non-matrix molecules include VCAM-1, which is expressed on cytokine-activated human umbilical vein endothelial cells in culture. Distinct epitopes of VLA4 are responsible for the fibronectin and VCAM-1 binding activities, and each activity has been shown to be inhibited independently.[2]

Intercellular adhesion mediated by VLA-4 and other cell surface receptors is associated with a number of inflammatory responses. At the site of an injury or other inflammatory stimulus, activated vascular endothelial cells express molecules that are adhesive for leukocytes. The mechanics of leukocyte adhesion to endothelial cells involves, in part, the recognition and binding of cell surface receptors on leukocytes to the corresponding cell surface molecules on endothelial cells. Once bound, the leukocytes migrate across the blood vessel wall to enter the injured site and release chemical mediators to combat infection. For reviews of adhesion receptors of the immune system, see, for example, Springer[3] and Osborn[4].

Inflammatory brain disorders, such as experimental autoimmune encephalomyelitis (EAE), multiple sclerosis (MS) and meningitis, are examples of central nervous system disorders in which the endothelium/leukocyte adhesion mechanism results in destruction to otherwise healthy brain tissue. Large numbers of leukocytes migrate across the blood brain barrier (BBB) in subjects with these inflammatory diseases. The leukocytes release toxic mediators that cause extensive tissue damage resulting in impaired nerve conduction and paralysis.

In other organ systems, tissue damage also occurs via an adhesion mechanism resulting in migration or activation of leukocytes. For example, it has been shown that the initial insult following myocardial ischemia to heart tissue can be further complicated by leukocyte entry to the injured tissue causing still further insult (Vedder et al.[5]). Other inflammatory conditions mediated by an adhesion mechanism include, by way of example, asthma[6-8], Alzheimer's disease, atherosclerosis[9-10], AIDS dementia[11], diabetes 12-14 (including acute juvenile onset diabetes), inflammatory bowel disease[15] (including ulcerative colitis and Crohn's disease), multiple sclerosis[16-17], rheumatoid arthritis[18-21], tissue transplantation[22], tumor metastasis[23-28], meningitis, encephalitis, stroke, and other cerebral traumas, nephritis, retinitis, atopic dermatitis, psoriasis, myocardial ischemia and acute leukocyte-mediated lung injury such as that which occurs in adult respiratory distress syndrome.

In view of the above, assays for determining the VLA-4 level in a biological sample containing VLA-4 would be useful, for example, to diagnosis VLA-4 mediated conditions. Additionally, despite these advances in the understanding of leukocyte adhesion, the art has only recently addressed the use of inhibitors of adhesion in the treatment of inflammatory brain diseases and other inflammatory conditions[29,30]. The present invention addresses these and other needs.

SUMMARY OF THE INVENTION

This invention provides compounds which bind to VLA-4. Such compounds can be used, for example, to assay for the presence of VLA-4 in a sample and, in pharmaceutical compositions, to inhibit cellular adhesion mediated by VLA-4, for example, binding of VCAM-1 to VLA-4. The compounds of this invention have a binding affinity to VLA-4 as expressed by an $IC_{50}$ of about 15 μM or less (as measured by Example 95 below), which compounds are defined by formula I below:

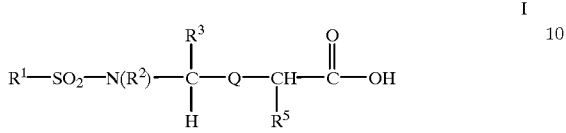

where $R^1$ is selected from the group consisting of alkyl, substituted alkyl, aryl, substituted aryl, cycloalkyl, substituted cycloalkyl, heterocyclic, substituted heterocylic, heteroaryl and substituted heteroaryl;

$R^2$ and $R^3$ together with the nitrogen atom bound to $R^2$ and the carbon atom bound to $R^3$ form a saturated heterocyclic group or a saturated substituted heterocyclic group with the proviso that when monosubstituted, the substituent on said saturated heterocyclic group is not carboxyl;

$R^5$ is selected from the group consisting of —$(CH_2)_n$-aryl and —$(CH_2)_n$-heteroaryl, where n is an integer equal to 1 to 4;

Q is —$C(X)NR^7$— wherein $R^7$ is selected from the group consisting of hydrogen and alkyl, and X is selected from the group consisting of oxygen and sulfur;

and pharmaceutically acceptable salts thereof, with the proviso that when $R^1$ is 2,4,6-trimethylphenyl, $R^2$ and $R^3$ together with the pendent nitrogen and carbon atoms form a pyrrolidinyl ring and Q is —C(O)NH—, then $R^5$ is not benzyl; and with the further proviso that when $R^1$ is p-methylphenyl, $R^2$ and $R^3$ together with the pendent nitrogen and carbon atoms form a pyrrolidinyl ring derived from D-proline and Q is —C(O)NH—, then $R^5$ is not benzyl derived from D-phenylalanine.

In another embodiment, the compounds of this invention can also be provided as prodrugs which convert (e.g., hydrolyze, metabolize, etc.) in vivo to a compound of formula I above. In a preferred example of such an embodiment, the carboxylic acid of the compound of formula I is modified into a group which, in vivo, will convert to a carboxylic acid (including salts thereof). In a particularly preferred embodiment, such prodrugs are represented by compounds of formula IA:

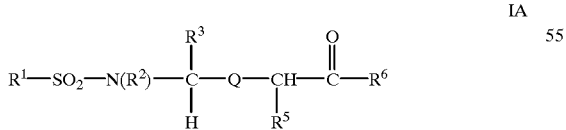

$R^1$ is selected from the group consisting of alkyl, substituted alkyl, aryl, substituted aryl, cycloalkyl, heterocyclic, substituted heterocylic, heteroaryl and substituted heteroaryl;

$R^2$ and $R^3$ together with the nitrogen atom bound to $R^2$ and the carbon atom bound to $R^3$ form a saturated heterocyclic group or a saturated substituted heterocyclic group with the proviso that when monosubstituted, the substituent on said saturated heterocyclic group is not carboxyl;

$R^5$ is selected from the group consisting of —$(CH_2)_n$-aryl and —$(CH_2)_n$-heteroaryl, where n is an integer equal to 1 to 4;

$R^6$ is selected from the group consisting of amino, alkoxy, substituted alkoxy, cycloalkoxy, substituted cycloalkoxy, —O-(N-succinimidyl), —NH-adamantyl, —O-cholest-5-en-3-β-yl, —NHOY where Y is hydrogen, alkyl, substituted alkyl, aryl, and substituted aryl, —$NH(CH_2)_p COOY$ where p is an integer of from 1 to 8 and Y is as defined above, —$OCH_2 NR^9 R^{10}$ where $R^9$ is selected from the group consisting of —C(O)-aryl and —C(O)-substituted aryl and $R^{10}$ is selected from the group consisting of hydrogen and —$CH_2 COOR^{11}$ where $R^{11}$ is alkyl, and —$NHSO_2 Z$ where Z is alkyl, substituted alkyl, cycloalkyl, substituted cycloalkyl, aryl, substituted aryl, heteroaryl, substituted heteroaryl, heterocyclic and substituted heterocyclic;

Q is —$C(X)NR^7$- wherein $R^7$ is selected from the group consisting of hydrogen and alkyl, and X is selected from the group consisting of oxygen and sulfur;

and pharmaceutically acceptable salts thereof, with the following provisos:

A. when $R^1$ is 4-methylphenyl, $R^2$ and $R^3$ together with the pendent nitrogen and carbon atoms form a pyrrolidin-2-yl ring, $R^5$ is benzyl and Q is —C(O)NH—, then $R^6$ is not —$NH(CH_2)_2 CO_2 Et$ or -(1R, 2S,5R)-(–)-menthyl ester;

B. when $R^1$ is 4-methylphenyl, $R^2$ and $R^3$ together with the pendent nitrogen and carbon atoms form a 3-β-phenyl-ring derived from D-proline, $R^5$ is benzyl and Q is —C(O)NH—, then $R^6$ is not —$OCH_2 CH_3$;

C. when $R^1$ is 1-N-methyl-3-methyl-5-chloropyrazol-4-yl, $R^2$ and $R^3$ together with the pendent nitrogen and carbon atoms form a pyrrolidin-2-yl ring, $R^5$ is benzyl and Q is —C(O)NH—, then $R^6$ is not —$OCH_3$;

D. when $R^1$ is 4-methylphenyl, $R^2$ and $R^3$ together with the pendent nitrogen and carbon atoms form a pyrrolidin-2-yl ring, $R^5$ is D-benzyl and Q is —C(O)NH—, then $R^6$ is not —$OCH_2 CH_3$;

E. when $R^1$ is 4-methylphenyl, $R^2$ and $R^3$ together with the pendent nitrogen and carbon atoms form a 5,5-dimethyl-1,1-dioxo-thiaprolyl ring, $R^5$ is benzyl and Q is —C(O)NH—, then $R^6$ is not —$OC(CH_3)_3$; and F. when $R^1$ is 4-methylphenyl, $R^2$ and $R^3$ together with the pendent nitrogen and carbon atoms form a pyrrolidin-2-yl ring derived from D-proline, $R^5$ is benzyl derived from D-phenylalanine and Q is —C(O)NH—, then $R^6$ is not —$OCH_3$;

G. when $R^1$ is n-butyl, $R^2$ and $R^3$ together with the pendent nitrogen and carbon atoms form a pyrrolidin-2-yl ring, $R^5$ is benzyl and Q is —C(O)NH—, then $R^6$ is not —O-benzyl.

Preferably, in the compounds of formula I and IA above, $R^1$ is selected from the group consisting of alkyl, substituted alkyl, aryl, substituted aryl, heterocyclic, substituted heterocylic, heteroaryl and substituted heteroaryl. Even more preferably $R^1$ is selected from the group consisting of 4-methylphenyl, methyl, benzyl, n-butyl, 4-chlorophenyl, 1-naphthyl, 2-naphthyl, 4-methoxyphenyl, phenyl, 2,4,6-trimethylphenyl, 2-(methoxycarbonyl)phenyl, 2-carboxyphenyl, 3,5-dichlorophenyl, 4-trifluoromethylphenyl, 3,4-dichlorophenyl, 3,4-dimethoxyphenyl, 4-(CH$_3$C(O)NH—)phenyl, 4-trifluoromethoxyphenyl, 4-cyanophenyl, isopropyl, 3,5-di-(trifluoromethyl)phenyl, 4-t-butylphenyl, 4-t-butoxyphenyl, 4-nitrophenyl, 2-thienyl, 1-N-methyl-3-methyl-5-chloropyrazol-4-yl, phenethyl, 1-N-methylimidazol-4-yl, 4-bromophenyl, 4-amidinophenyl, 4-methylamidinophenyl, 4-[CH$_3$SC(=NH)]phenyl, 5-chloro-2-thienyl, 2,5-dichloro-4-thienyl, 1-N-methyl-4-pyrazolyl, 2-thiazolyl, 5-methyl-1,3,4-thiadiazol-2-yl, 4-[H$_2$NC(S)]phenyl, 4-aminophenyl, 4-fluorophenyl, 2-fluorophenyl, 3-fluorophenyl, 3,5-difluorophenyl, pyridin-3-yl, pyrimidin-2-yl, and 4-(3'-dimethylamino-n-propoxy)-phenyl.

In one preferred embodiment, R$^2$ and R$^3$ together with the nitrogen atom bound to the R$^2$ substituent and the carbon bound to the R$^3$ substituent form a heterocyclic group or substituted heterocyclic group of 4 to 6 ring atoms having 1 to 2 heteroatoms in the ring selected from nitrogen, oxygen and sulfur, which ring is optionally substituted with 1 to 2 substituents selected from fluoro, methyl, hydroxy, amino, phenyl, thiophenyl and thiobenzyl, or can be fused to another saturated heterocyclic or cycloalkyl ring such as a cyclohexyl ring to provide for a fused ring heterocycle of from 10 to 14 ring atoms having 1 to 2 heteroatoms in the ring selected from nitrogen, oxygen and sulfur. Such heterocyclic rings include thiazolidinyl (e.g., L-thiazolidin-4-yl), piperidinyl (e.g., L-piperidin-2-yl), piperizinyl (e.g., L-piperizin-2-yl), thiomorpholinyl (e.g., L-thiomorpholin-3-yl), pyrrolidinyl (e.g., L-pyrrolidin-2-yl), substituted pyrrolidinyl such as 4-hydroxypyrrolidinyl (e.g., 4-α-(or β-)hydroxy-L-pyrrolidin-2-yl), 4-fluoropyrrolidinyl (e.g., 4-α-(or β-)fluoro-L-pyrrolidin-2-yl), 3-phenylpyrrolidinyl (e.g., 3-α-(or β-)phenyl-L-pyrrolidin-2-yl), 3-thiophenylpyrrolidinyl (e.g., 3-α-(or β-)thiophenyl-L-pyrrolidin-2-yl), 4-aminopyrrolidinyl (e.g., 4-α-(or β-)amino-L-pyrrolidin-2-yl), 3-methoxypyrrolidinyl (e.g., 3-α-(or β-)methoxy-L-pyrrolidin-2-yl), 4,4-dimethylpyrrolidin-2-yl, substituted piperizinyl such as 4-N-Cbz-piperizin-2-yl, substituted thiazolidinyl such as 5,5-dimethylthiazolindin-4-yl, 1,1-dioxo-thiazolidinyl (e.g., L-1,1-dioxo-thiazolidin-4-yl), substituted 1,1-dioxo-thiazolidinyl such as L-1,1-dioxo-5,5-dimethylthiazolidin-4-yl, 1,1-dioxothiomorpholinyl (e.g., L-1,1-dioxo-thiomorpholin-3-yl) and the like. Preferably, such rings do not include those where R$^2$ and R$^3$ together with the nitrogen atom bound to R$^2$ and the carbon atom bound to R$^3$ form a azetidine ring.

Q is preferably —C(O)NH— or —C(S)NH—.

R$^5$ is preferably selected from all possible isomers arising by substitution of the following groups: benzyl, phenethyl, —CH$_2$-(3-indolyl), —CH$_2$-(1-naphthyl), —CH$_2$-(2-naphthyl), —CH$_2$-(2-thienyl), —CH$_2$-(3-pyridyl), —CH$_2$-(5-imidazolyl), —CH$_2$-3-(1,2,4-triazolyl), —CH$_2$-(2-thiazolyl) and the like.

In the compounds of formula IA, R$^6$ is preferably 2,4-dioxo-tetrahydrofuran-3-yl (3,4-enol), methoxy, ethoxy, iso-propoxy, n-butoxy, t-butoxy, cyclopentoxy, neo-pentoxy, 2-α-iso-propyl-4-β-methylcyclohexoxy, 2-β-isopropyl-4-β-methylcyclohexoxy, —NH$_2$, benzyloxy, —NHCH$_2$COOH, —NHCH$_2$CH$_2$COOH, —NH-adamantyl, —NHCH$_2$CH$_2$COOCH$_2$CH$_3$, —NHSO$_2$-p-CH$_3$-φ, —NHOR$^8$ where R$^8$ is hydrogen, methyl, iso-propyl or benzyl, O-(N-succinimidyl), —O-cholest-5-en-3-β-yl, —OCH$_2$—OC(O)C(CH$_3$)$_3$, —O(CH$_2$)$_z$NHC(O)W where z is 1 or 2 and W is selected from the group consisting of pyrid-3-yl, N-methylpyridyl, and N-methyl-1,4-dihydro-pyrid-3-yl, and —NR"C(O)—R' where R' is aryl, heteroaryl or heterocyclic and R" is hydrogen or —CH$_2$C(O)OCH$_2$CH$_3$.

Preferred compounds within the scope of formula I and IA above include by way of example:
N-(methanesulfonyl)-L-prolyl-L-phenylalanine
N-(α-toluenesulfonyl)-L-prolyl-L-phenylalanine
N-(toluene-4-sulfonyl)-L-prolyl-L-phenylalanine
N-(toluene-4-sulfonyl)-L-prolyl-L-(N-methyl)phenylalanine
N-(toluene-4-sulfonyl)-L-pipecolinyl-L-phenylalanine
N-(toluene-4-sulfonyl)-D-prolyl-L-phenylalanine
N-(toluene-4-sulfonyl)-L-(4-hydroxy)prolyl-L-phenylalanine
N-(toluene-4-sulfonyl)-L-prolyl-D,L-homophenylalanine
N-(4-chlorobenzenesulfonyl)-L-prolyl-L-phenylalanine
N-(1-naphthalenesulfonyl)-L-prolyl-L-phenylalanine
N-(2-naphthalenesulfonyl)-L-prolyl-L-phenylalanine
N-(4-methoxybenzenesulfonyl)-L-prolyl-L-phenylalanine
N-(4-tert-butylbenzenesulfonyl)-L-prolyl-L-phenylalanine
N-(toluene4-sulfonyl)-L-(4-fluoro)prolyl-L-phenylalanine
N-(n-butanesulfonyl)-L-prolyl-L-phenylalanine
N-(toluene-4-sulfonyl)-L-(5,5-dimethyl)thiaprolyl-L-phenylalanine
N-(2-methoxycarbonylbenzenesulfonyl)-L-prolyl-L-phenylalanine
N-(2-carboxybenzenesulfonyl)-L-prolyl-L-phenylalanine
N-(toluene-4-sulfonyl)-L-thiaprolyl-L-phenylalanine
N-(3,5-dichlorobenzenesulfonyl)-L-prolyl-L-phenylalanine
N-(4-trifluoromethoxybenzenesulfonyl)-L-prolyl-L-phenylalanine
N-(3,4-dichlorobenzenesulfonyl)-L-prolyl-L-phenylalanine
N-(toluene-4-sulfonyl)-D,L-(3-phenyl)prolyl-L-phenylalanine
N-(3,4-dimethoxybenzenesulfonyl)-L-prolyl-L-phenylalanine
N-(4-nitrobenzenesulfonyl)-L-prolyl-L-phenylalanine
N-(4-acetamidobenzenesulfonyl)-L-prolyl-L-phenylalanine
N-(4-cyanobenzenesulfonyl)-L-prolyl-L-phenylalanine
N-(toluene-4-sulfonyl)-L-prolyl-L-tryptophan
N-(toluene-4-sulfonyl)-L-prolyl-β-(1-naphthyl)-L-alanine
N-(toluene-4-sulfonyl)-L-prolyl-β-(2-naphthyl)-L-alanine
N-(toluene-4-sulfonyl)-L-prolyl-β-(2-thienyl)-L-alanine
N-(isopropanesulfonyl)-L-prolyl-L-phenylalanine
N-(toluene-4-sulfonyl)-L-prolyl-β-(3-pyridyl)-L-alanine
N-(toluene-4-sulfonyl)-L-(4-phenylthio)prolyl-L-phenylalanine
N-(toluene-4-sulfonyl)-(4-benzylthio)-L-prolyl-L-phenylalanine
N-(toluene-4-sulfonyl)-L-prolyl-L-histidine
N-(toluene-4-sulfonyl)-L-(4-amino)prolyl-L-phenylalanine
N-(toluene-4-sulfonyl)-L-prolyl-L-phenylalaninamide
N-(toluene-4-sulfonyl)-L-prolyl-L-phenylalanine benzyl ester
N-(toluene-4-sulfonyl)-L-prolyl-L-phenylalanine ethyl ester
N-(toluene-4-sulfonyl)-L-prolyl-L-phenylalanine N-methoxyamide
N-(toluene-4-sulfonyl)-L-prolyl-L-phenylalanine N-benzyloxyamide
N-(toluene-4-sulfonyl)-L-prolyl-L-phenylalanine N-(toluene-4-sulfonyl)amide
N-(toluene-4-sulfonyl)-L-prolyl-L-phenylalaninyl-β-alanine N-(toluene-4-sulfonyl)-L-prolyl-L-phenylalanine N-hydroxyaimide
N-(toluene-4-sulfonyl)-L-prolyl-L-phenylalanine isopropyl ester
N-(toluene-4-sulfonyl)-L-(4-hydroxy)prolyl-L-phenylalanine
N-(toluene-4-sulfonyl)-L-prolyl-L-phenylalaninyl-(N-benzoyl)glycine ethyl ester
N-(toluene-4-sulfonyl)-L-(4-fluoro)prolyl-L-phenylalanine benzyl ester
N-(toluene-4-sulfonyl)-L-thiaprolyl-L-phenylalanine benzyl ester
N-(toluene-4-sulfonyl)-L-(5,5-dimethyl)thiaprolyl-L-phenylalanine benzyl ester
N-(toluene-4-sulfonyl)-L-(5,5-dimethyl)tiaprolyl-L-phenylalanine ethyl ester
N-(2-methoxycarbonylbenzenesulfonyl)-L-prolyl-L-phenylalanine benzyl ester
N-(toluene-4-sulfonyl)-L-(3-phenyl)prolyl-L-phenylalanine ethyl ester
N-(toluene-4-sulfonyl)-L-(4-methoxy)prolyl-L-phenylalanine
N-(toluene-4-sulfonyl)-L-prolyl-L- phenylalanine (1S,2R,5S)-(+)-menthyl ester
N-(toluene-4-sulfonyl)-L-prolyl-L-phenylalanine N-hydroxysuccinimide ester
N-(toluene-4-sulfonyl)-L-prolyl-L-phenylalanine 2-(nicotinamido)ethyl ester
N-(toluene-4-sulfonyl)-L-prolyl-L-phenylalanine 2-(1-methylpyridinium-3-amido)ethyl ester
N-(toluene-4-sulfonyl)-L-prolyl-L-phenylalanine cholesteryl ester
N-(toluene-4-sulfonyl)-L-prolyl-L-phenylalanine 2-(1-methyl-1,4-dihydropyridinyl-3-amido)ethyl ester
N-(thiophene-2-sulfonyl)-L-prolyl-L-phenylalanine methyl ester
N-(thiophene-2-sulfonyl)-L-prolyl-L-phenylalanine
N-(5-chloro-1,3-dimethylpyrazole4-sulfonyl)-L-prolyl-L-phenylalanine
N-(2-phenylethanesulfonyl)-L-prolyl-L-phenylalanine
N-(1-methylimidazole-4-sulfonyl)-L-prolyl-L-phenylalanine methyl ester
N-(1-methylimidazole-4-sulfonyl)-L-prolyl-L-phenylalanine
N-(4-amidinobenzenesulfonyl)-L-prolyl-L-phenylalanine methyl ester
N-(4-amidinobenzenesulfonyl)-L-prolyl-L-phenylalanine
N-(4-thiomethoxyimidatylbenzene-4-sulfonyl)-L-prolyl-L-phenylalanine methyl ester
N-[4-(N-methylthioamido)benzenesulfonyl]-L-prolyl-L-phenylalanine methyl ester
N-(toluene-4-sulfonyl)-L-prolyl-D,L-β-(1,2,4-triazol-3-yl)alanine
N-(toluene-4-sulfonyl)-L-prolyl-D,L-β-(thiazol-2-yl)alanine
N-[4-(3-dimethylaminopropyloxy)benzenesulfonyl]-L-prolyl-L-phenylalanine
N-(toluene-4-sulfonyl)-L-pyrrolidin-2-yl-thiocarbonyl-L-phenylalanine
N-(4-thiocarbamoylbenzenesulfonyl)-L-(5,5-dimethyl)thiaprolyl-L-phenylalanine benzyl ester
N-(4-cyanobenzenesulfonyl)-L-(5,5-dimethyl)thiaprolyl-L-phenylalanine benzyl ester
N-(toluene-4-sulfonyl)-L-prolyl-D-phenylalanine
N-(toluene-4-sulfonyl)-L-(thiamorpholin-3-carbonyl)-L-phenylalanine
N-(toluene-4-sulfonyl)-[(1,1-dioxo)thiamorpholin-3-carbonyl]-L-phenylalanine
N-(toluene-4-sulfonyl)-L-(3,3-dimethyl)prolyl-L-phenylalanine
N-(toluene-4-sulfonyl)-L-(5,5-dimethyl-1,1-dioxo) thiaprolyl-L-phenylalanine
N-(toluene4-sulfonyl)-[(1,1-dioxo)thiamorpholin-3-carbonyl]-L-phenylalanine ethyl ester
N-(toluene-4-sulfonyl)-L-prolyl-L-phenylalanine tert-butyl ester
N-(toluene-4-sulfonyl)-L-pyrrolidin-2-yl-thiocarbonyl-L-phenylalanine methyl ester
N-(benzenesulfonyl)-L-prolyl-L-phenylalanine methyl ester
N-(toluene-4-sulfonyl)-L-(5-oxo)prolyl-L-phenylalanine ethyl ester
N-(toluene-4-sulfonyl)-L-(5-oxo)prolyl-L-phenylalanine and pharmaceutically acceptable salts thereof, as well as any of the ester compounds recited above wherein one ester is replaced with another ester selected from the group consisting of methyl ester, ethyl ester, n-propyl ester, isopropyl ester, n-butyl ester, isobutyl ester, sec-butyl ester and tert-butyl ester.

This invention also provides methods for binding VLA-4 in a biological sample which method comprises contacting the biological sample with a compound of formula I or IA above under conditions wherein said compound binds to VLA4.

Certain of the compounds of formula I and IA above are also useful in reducing VLA-4 mediated inflammation in vivo.

This invention also provides pharmaceutical compositions comprising a pharmaceutically acceptable carrier and a therapeutically effective amount of one or more of the compounds of formula I or IA above, with the exception that $R^3$ and $R^5$ are derived from L-amino acids or other similarly configured starting materials. Alternatively, racemic mixtures can be used.

The pharmaceutical compositions may be used to treat VLA4 mediated disease conditions. Such disease conditions include, by way of example, asthma, Alzheimer's disease, atherosclerosis, AIDS dementia, diabetes (including acute juvenile onset diabetes), inflammatory bowel disease (including ulcerative colitis and Crohn's disease), multiple sclerosis, rheumatoid arthritis, tissue transplantation, tumor metastasis, meningitis, encephalitis, stroke, and other cerebral traumas, nephritis, retinitis, atopic dermatitis, psoriasis, myocardial ischemia and acute leukocyte-mediated lung injury such as that which occurs in adult respiratory distress syndrome.

Accordingly, this invention also provides methods for the treatment of an inflammatory disease in a patient mediated by VLA-4 which methods comprise administering to the patient the pharmaceutical compositions described above.

Preferred compounds of formula I and IA above include those set forth in Table I below:

TABLE I $$R^1—SO_2—N(R^2)—\underset{H}{\overset{R^3}{C}}—Q—\underset{R^5}{CH}—\overset{O}{\overset{\|}{C}}—R^{6'}$$

| R¹ | R² | R³ R⁵ | R⁶' | Q = —C(O)NR⁷—R⁷ |
|---|---|---|---|---|
| H₃C— | R²/R³ = cyclic 3 carbon atoms (L-pyrrolidinyl) | —CH₂-φ | —OH | H |
| φ-CH₂— | R²/R³ = cyclic 3 carbon atoms (L-pyrrolidinyl) | —CH₂-φ | —OH | H |
| p-CH₃-φ- | R²/R³ = cyclic 3 carbon atoms (L-pyrrolidinyl) | —CH₂-φ | —OH | H |
| p-CH₃-φ- | R²/R³ = cyclic 3 carbon atoms (L-pyrrolidinyl) | —CH₂-φ | —OH | —CH₃ |
| p-CH₃-φ- | R²/R³ = cyclic 4 carbon atoms (L-piperidin-2-yl) | —CH₂-φ | —OH | H |
| p-CH₃-φ- | R²/R³ = cyclic 3 carbon atoms (D-pyrrolidinyl) | —CH₂-φ | —OH | H |
| p-CH₃-φ- | R²/R³ = —CH₂CH(OH)CH₂— (L-4-β-hydroxy-pyrrolidinyl) | —CH₂-φ | —OH | H |
| p-CH₃-φ- | R²/R³ = cyclic 2 carbon atoms (L-isomer) | —CH₂-φ | —OH | H |
| p-CH₃-φ- | R²/R³ = cyclic 3 carbon atoms (L-pyrrolidinyl) | —CH₂CH₂-φ | —OH | H |
| p-Cl-φ- | R²/R³ = cyclic 3 carbon atoms (L-pyrrolidinyl) | —CH₂-φ | —OH | H |
| 1-naphthyl- | R²/R³ = cyclic 3 carbons atoms (L-pyrrolidinyl) | —CH₂-φ | —OH | H |
| 2-naphthyl- | R²/R³ = cyclic 3 carbon atoms (L-pyrrolidinyl) | —CH₂-φ | —OH | H |
| p-CH₃O-φ- | R²/R³ = cyclic 3 carbon atoms (L-pyrrolidinyl) | —CH₂-φ | —OH | H |
| p-(t-butyl)-φ- | R²/R³ = cyclic 3 carbon atoms (L-pyrrolidinyl) | —CH₂-φ | —OH | H |
| p-CH₃-φ- | R²/R³ = cyclic —CH₂CH(F)CH₂— (4-β-fluoro-L-pyrrolidinyl) | —CH₂-φ | —OH | H |
| p-CH₃-φ- | R²/R³ = cyclic —CH₂CH(F)CH₂— (4-α-fluoro-L-pyrrolidinyl) | —CH₂-φ | —OH | H |
| n-butyl | R²/R³ = cyclic 3 carbon atoms (L-pyrrolidinyl) | —CH₂-φ | —OH | H |
| p-CH₃-φ- | R²/R³ = cyclic —CH₂S—C(CH₃)₂— (L-5,5-dimethylthiazolidin-4-yl) | —CH₂-φ | —OH | H |
| o-methoxy-carbonyl-φ- | R²/R³ = cyclic 3 carbon atoms (L-pyrrolidinyl) | —CH₂-φ | —OH | H |
| o-carboxyl-φ- | R²/R³ = cyclic 3 carbon atoms (L-pyrrolidinyl) | —CH₂-φ | —OH | H |
| p-CH₃-φ- | R²/R³ = cyclic —CH₂SCH₂— (L-thiazolidin-4-yl) | —CH₂-φ | —OH | H |
| 3,5-dichloro-φ- | R²/R³ = cyclic 3 carbon atoms (L-pyrrolidinyl) | —CH₂-φ | —OH | H |
| p-trifluoro-methoxy-φ- | R²/R³ = cyclic 3 carbon atoms | —CH₂-φ | —OH | H |

TABLE I-continued $$R^1-SO_2-N(R^2)-\underset{H}{\overset{R^3}{C}}-Q-\underset{R^5}{CH}-\overset{O}{\overset{\|}{C}}-R^{6'}$$

| R¹ | R² | R³ R⁵ | R⁶' | Q = —C(O)NR⁷—R⁷ |
|---|---|---|---|---|
| 3,4-dichloro-φ- | R²/R³ = cyclic 3 carbon atoms (L-pyrrolidinyl) | —CH₂-φ | —OH | H |
| p-CH₃-φ- | R²/R³ = cyclic —CH₂CH₂CH(φ)- (3-β-phenyl-L-pyrrolidin-2-yl) | —CH₂-φ | —OH | H |
| 3,4-dimethoxy-φ- | R²/R³ = cyclic 3 carbon atoms (L-pyrrolidinyl) | —CH₂-φ | —OH | H |
| φ- | R²/R³ = cyclic —CH₂CH₂CH(φ)- (3-β-phenyl-L-pyrrolidinyl) | —CH₂-φ | —OH | H |
| p-nitro-φ- | R²/R³ = cyclic 3 carbon atoms (L-pyrrolidinyl) | —CH₂-φ | —OH | H |
| p-CH₃C(O)NH-φ- | R²/R³ = cyclic 3 carbon atoms (L-pyrrolidinyl) | —CH₂-φ | —OH | H |
| p-cyano-φ- | R²/R³ = cyclic 3 carbon atoms (L-pyrrolidinyl) | —CH₂-φ | —OH | H |
| p-CH₃-φ- | R²/R³ = cyclic 3 carbon atoms (L-pyrrolidinyl) | (3-indolyl)-CH₂— | —OH | H |
| p-CH₃-φ- | R²/R³ = cyclic 3 carbon atoms (L-pyrrolidinyl) | —CH₂-(1-naphthyl) | —OH | H |
| p-CH₃-φ- | R²/R³ = cyclic 3 carbon atoms (L-pyrrolidinyl) | —CH₂-(2-naphthyl) | —OH | H |
| p-CH₃-φ- | R²/R³ = cyclic 3 carbon atoms (L-pyrrolidinyl) | —CH₂-(2-thienyl) | —OH | H |
| isopropyl | R²/R³ = cyclic 3 carbon atoms (L-pyrrolidinyl) | —CH₂φ | —OH | H |
| p-CH₃-φ- | R²/R³ = cyclic 3 carbon atoms (L-pyrrolidinyl) | 3-pyridyl-CH₂— | —OH | H |
| p-CH₃-φ- | R²/R³ = cyclic —CH₂CH(Sφ)CH₂— (3-α-thienyl-L-pyrrolidinyl-2-yl) | —CH₂-φ | —OH | H |
| p-CH₃-φ- | R²/R³ = cyclic —CH₂CH(SCH₂φ)CH₂— 3-(α-thienyl-D-pyrrolidinyl-2-yl) | —CH₂-φ | —OH | H |
| p-CH₃-φ- | R²/R³ = cyclic 3 carbon atoms (L-pyrrolidinyl) | imidazol-5-yl-CH₂— | —OH | H |
| p-CH₃-φ- | R²/R³ = cyclic —CH₂CH(NH₂)CH₂— (4-α-amino-L-pyrrolidin-2-yl) | —CH₂-φ | —OH | H |
| p-CH₃-φ- | R²/R³ = 4-α-amino-D-pyrrolidin-2-yl | —CH₂-φ | —OH | H |
| p-CH₃-φ- | R²/R³ = cyclic 3 carbon atoms (L-pyrrolidinyl) | —CH₂-φ | —NH₂ | H |
| p-CH₃-φ- | R²/R³ = cyclic 3 carbon atoms (L-pyrrolidinyl) | —CH₂-φ | —O—CH₂-φ | H |
| p-CH₃-φ- | R²/R³ = cyclic 3 carbon atoms (L-pyrrolidinyl) | —CH₂-φ | —O-ethyl | H |
| p-CH₃-φ- | R²/R³ = cyclic 3 carbon atoms (L-pyrrolidinyl) | —CH₂-φ | —NHOCH₃ | H |
| p-CH₃-φ- | R²/R³ = cyclic 3 carbon atoms (L-pyrrolidinyl) | —CH₂-φ | —NHO—CH₂-φ | H |
| p-CH₃-φ- | R²/R³ = cyclic | —CH₂-φ | —NHSO₂-(p- | H |

TABLE I-continued

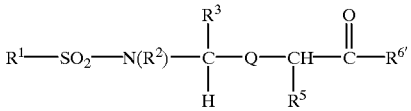

| R¹ | R² | R³ | R⁵ | R⁶' | Q = —C(O)NR⁷—R⁷ |
|---|---|---|---|---|---|
| | 3 carbon atoms (L-pyrrolidinyl) | | | methylphenyl) | |
| p-CH₃-φ- | R²/R³ = cyclic 3 carbon atoms (L-pyrrolidinyl) | | —CH₂-φ | —NH(CH₂)₂—CO₂H | H |
| p-CH₃-φ- | R²/R³ = cyclic 3 carbon atoms (L-pyrrolidinyl) | | —CH₂-φ | —NHOH | H |
| p-CH₃-φ- | R²/R³ = cyclic 3 carbon atoms (L-pyrrolidinyl) | | —CH₂-φ | —O-isopropyl | H |
| p-CH₃-φ- | R²/R³ = cyclic —CH₂CH(OH)CH₂— (4-α-hydroxy-D-pyrrolidin-2-yl) | | —CH₂-φ | —OH | H |
| p-CH₃-φ- | R²/R³ = cyclic 3 carbon atoms (L-pyrrolidinyl) | | —CH₂-φ | —OCH₂NC(O)φ \| EtOC(O)CH₂ | H |
| p-CH₃-φ- | R²/R³ = cyclic —CH₂CH(F)CH₂— (4-β-fluoro-L-pyrrolidinyl) | | —CH₂-φ | —O—CH₂-φ | H |
| p-CH₃-φ- | R²/R³ = cyclic —CH₂CH(F)CH₂— (4-α-fluoro-L-pyrrolidinyl) | | —CH₂-φ | —O—CH₂-φ | H |
| p-CH₃-φ- | R²/R³ = cyclic —CH₂S—CH₂— (L-thiazolidin-4-yl) | | —CH₂-φ | —O—CH₂-φ | H |
| p-CH₃-φ- | R²/R³ = cyclic —CH₂S—C(CH₃)₂— (L-5,5-dimethylthiazolidin-4-yl) | | —CH₂-φ | —O—CH₂-φ | H |
| p-CH₃-φ- | R²/R³ = cyclic —CH₂S—C(CH₃)₂— (L-5,5-dimethylthiazolidin-4-yl) | | —CH₂-φ | —OCH₂CH₃ | H |
| methoxycarbonyl-φ | R²/R³ = cyclic 3 carbon atoms (L-pyrrolidinyl) | | —CH₂-φ | —O—CH₂-φ | H |
| p-CH₃-φ- | R²/R³ = cyclic —CH₂CH₂CH(φ)- (3-β-phenyl-L-pyrrolidin-2-yl) | | —CH₂-φ | —OCH₂CH₃ | H |
| p-CH₃-φ- | R²/R³ = cyclic —CH₂CH(OCH₃)CH₂— (3-methoxy-L-pyrrolidin-2-yl) | | —CH₂-φ | OH | H |
| p-CH₃-φ- | R²/R³ = cyclic 3 carbon atoms (L-pyrrolidinyl) | | —CH₂-φ | 2-β-isopropyl-4-α-methyl-cyclohex-1-oxy | H |
| p-CH₃-φ- | R²/R³ = cyclic 3 carbon atoms (L-pyrrolidinyl) | | —CH₂-φ | —O—(N-succinimidyl) | H |
| p-CH₃-φ- | R²/R³ = cyclic 3 carbon atoms (L-pyrrolidinyl) | | —CH₂-φ | —OCH₂CH₂—NHC(O)-pyrid-3-yl | H |
| p-CH₃-φ- | R²/R³ = cyclic 3 carbon atoms (L-pyrrolidinyl) | | —CH₂-φ | —OCH₂CH₂—NHC(O)—N-methylpyrid-3-yl | H |
| p-CH₃-φ- | R²/R³ = cyclic 3 carbon atoms (L-pyrrolidinyl) | | —CH₂-φ | —O-cholest-5-en-3-β-yl | H |
| p-CH₃-φ- | R²/R³ = cyclic 3 carbon atoms (L-pyrrolidinyl) | | —CH₂-φ | —OCH₂CH₂—NHC(O)—N-N-methyl-1,4-dihydro-pyrid-3-yl | H |
| 2-thienyl | R²/R³ = cyclic 3 carbon atoms (L-pyrrolidinyl) | | —CH₂-φ | —OCH₃ | H |
| 2-thienyl | R²/R³ = cyclic 3 carbon atoms (L-pyrrolidinyl) | | —CH₂-φ | —OH | H |
| 1-N-methyl-3- | R²/R³ = cyclic | | —CH₂-φ | —OH | H |

TABLE I-continued $$R^1-SO_2-N(R^2)-\underset{H}{\overset{R^3}{C}}-Q-\underset{R^5}{CH}-\overset{O}{\overset{\|}{C}}-R^{6'}$$

| R¹ | R² | R³ R⁵ | R⁶' | Q = —C(O)NR⁷—R⁷ |
|---|---|---|---|---|
| methyl-5-chloropyrazol-4-yl | 3 carbon atoms (L-pyrrolidinyl) | | | |
| φ-CH₂CH₂— | R²/R³ = cyclic 3 carbon atoms (L-pyrrolidinyl) | —CH₂-φ | —OH | H |
| 1-N-methyl-imidazol-4-yl | R²/R³ = cyclic 3 carbon atoms (L-pyrrolidinyl) | —CH₂-φ | —OCH₃ | H |
| 1-N-methyl-imidazol-4-yl | R²/R³ = cyclic 3 carbon atoms (L-pyrrolidinyl) | —CH₂-φ | —OH | H |
| p-(NH₂C)-φ- ‖ NH | R²/R³ = cyclic 3 carbon atoms (L-pyrrolidinyl) | —CH₂-φ | —OCH₃ | H |
| p-(NH₂C)-φ- ‖ NH | R²/R³ = cyclic 3 carbon atoms (L-pyrrolidinyl) | —CH₂-φ | —OH | H |
| p-(CH₃SC)-φ- ‖ NH | R²/R³ = cyclic 3 carbon atoms (L-pyrrolidinyl) | —CH₂-φ | —OCH₃ | H |
| p-(CH₃NHC)-φ- ‖ NH | R²/R³ = cyclic 3 carbon atoms (L-pyrrolidinyl) | —CH₂-φ | —OCH₃ | H |
| p-CH₃-φ- | R²/R³ = cyclic 3 carbon atoms (L-pyrrolidinyl) | —CH₂-3-(1,2,4-triazolyl) | —OH | H |
| p-CH₃-φ- | R²/R³ = cyclic 3 carbon atoms (L-pyrrolidinyl) | —CH₂-2-thiazolyl | —OH | H |
| p-[—O(CH₂)₃—N(CH₃)₂]-φ- | R²/R³ = cyclic 3 carbon atoms (L-pyrrolidinyl) | —CH₂-φ | —OH | H |
| p-CH₃-φ- | R²/R³ = cyclic 3 carbon atoms (L-pyrrolidinyl) | —CH₂-φ | —OH | Q = —C(S)NH— |
| p-NH₂(S)C-φ- | R²/R³ = cyclic —CH₂—S—C(CH₃)₂— (L-5,5-dimethylthiazolidin-4-yl) | —CH₂-φ | —OCH₂-φ | H |
| p-NC-φ- | R²/R³ = cyclic —CH₂—S—C(CH₃)₂— (L-5,5-dimethylthiazolidin-4-yl) | —CH₂-φ | —OCH₂-φ | H |
| p-CH₃-φ- | R²/R³ = cyclic 3 carbon atoms (L-pyrrolidinyl) | —CH₂-φ | —OH | H |
| p-CH₃-φ- | R²/R³ = cyclic —CH₂CH₂—S—CH₂CH₂— (L-5,5-dimethylthiazolidin-4-yl) | —CH₂-φ | —OH | H |
| p-CH₃-φ- | R²/R³ = cyclic —CH₂CH₂—SO₂—CH₂— (L-1,1-dioxothiomorpholin-3-yl) | —CH₂-φ | —OH | H |
| p-CH₃-φ- | R²/R³ = cyclic —CH₂—CH₂—C(CH₃)₂— (L-4,4-dimethylpyrrolidinyl) | —CH₂-φ | —OH | H |
| p-CH₃-φ- | R²/R³ = cyclic —CH₂—SO₂—C(CH₃)₂— (L-1,1-dioxo-5,5-dimethylthiazolidin-4-yl) | —CH₂-φ | —OH | H |
| p-CH₃-φ- | R²/R³ = cyclic —CH₂CH₂—SO₂—CH₂— (L-1,1-dioxothiomorpholin-3-yl) | —CH₂-φ | —OCH₂CH₃ | H |
| p-CH₃-φ- | R²/R³ = cyclic 3 carbon atoms (L-pyrrolidinyl) | —CH₂-φ | —OC(CH₃)₃ | H |

TABLE I-continued $$R^1\text{---}SO_2\text{---}N(R^2)\text{---}\underset{H}{\overset{R^3}{C}}\text{---}Q\text{---}\underset{R^5}{CH}\text{---}\overset{O}{\overset{\|}{C}}\text{---}R^{6'}$$

| $R^1$ | $R^2$ | $R^3$ $R^5$ | $R^{6'}$ | Q = —C(O)NR$^7$—R$^7$ |
|---|---|---|---|---|
| p-CH$_3$-φ- | $R^2/R^3$ = cyclic 3 carbon atoms (L-pyrrolidinyl) | —CH$_2$-φ | —OCH$_3$ | Q = —C(S)NH— |
| φ- | $R^2/R^3$ = cyclic 3 carbon atoms (L-pyrrolidinyl) | —CH$_2$-φ | —OCH$_3$ | H |
| p-CH$_3$-φ- | $R^2/R^3$ = cyclic —C(O)—CH$_2$—CH$_2$— (L-5-oxopyrrolidinyl) | —CH$_2$-φ | —OCH$_2$CH$_3$ | H |
| p-CH$_3$-φ- | $R^2/R^3$ = cyclic —C(O)—CH$_2$—CH$_2$— (L-5-oxopyrrolidinyl) | —CH$_2$-φ | —OH | H |

DETAILED DESCRIPTION OF THE INVENTION

As above, this invention relates to compounds which inhibit leukocyte adhesion and, in particular, leukocyte adhesion mediated by VLA-4. However, prior to describing this invention in further detail, tile following terms will first be defined.

Definitions

As used herein, "alkyl" refers to alkyl groups preferably having from 1 to 10 carbon atoms and more preferably 1 to 6 carbon atoms. This term is exemplified by groups such as methyl, t-butyl, n-heptyl, octyl and the like.

"Substituted alkyl" refers to an alkyl group, preferably of from 1 to 10 carbon atoms, having from 1 to 5 substituents selected from the group consisting of alkoxy, substituted alkoxy, acyl, acylamino, thiocarbonylamino, acyloxy, amino, amidino, alkyl amidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, cyano, halogen, hydroxyl, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted aryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$-NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl) amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from alkyl, substituted alkyl, aryl, substituted aryl, heteroaryl, substituted heteroaryl, heterocyclic and substituted heterocyclic, and substituted alkyl groups having amino groups blocked by conventional blocking groups such as Boc, Cbz, formyl, and the like, and allyl/substituted alkyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

"Alkoxy" refers to the group "alkyl-O—" which includes, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

"Substituted alkoxy" refers to the group "substituted alkyl-O—".

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)— cycloalkyl-C(O)—, substituted cycloalkyl-C(O)—, aryl-C(O)—, substituted aryl-C(O)—, heteroaryl-C(O)—, substituted heteroaryl-C(O), heterocyclic-C(O)—, and substituted heterocyclic-C(O)—, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acylamino" refers to the group —C(O)NRR where each R is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic, and where each R is joined to form, together with the nitrogen atom, a heterocyclic or substituted heterocyclic ring, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Thiocarbonylamino" refers to the group —C(S)NRR where each R is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic, and where each R is joined to form, together with the nitrogen atom, a heterocyclic or substituted heterocyclic ring, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O—, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Alkenyl" refers to an alkenyl group preferably having from 2 to 10 carbon atoms, and more preferably 2 to 6 carbon atoms, and having at least 1, and preferably from 1–2, sites of alkenyl unsaturation.

"Substituted alkenyl" refers to alkenyl groups having from 1 to 5 substituents selected from the group consisting of alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$-N-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic and —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from alkyl, substituted alkyl, aryl, substituted aryl, heteroaryl, substituted heteroaryl, heterocyclic and substituted heterocyclic, and substituted alkenyl groups having amino groups blocked by conventional blocking groups such as Boc, Cbz, formyl, and the like, and alkenyl/substituted alkenyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

"Alkynyl" refers to an alkynyl group preferably having from 2 to 10 carbon atoms, and more preferably 3 to 6 carbon atoms, and having at least 1, and preferably from 1–2, sites of alkynyl unsaturation.

"Substituted alkynyl" refers to alkynyl groups having from 1 to 5 substituents selected from the group consisting of alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic and —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from alkyl, substituted alkyl, aryl, substituted aryl, heteroaryl, substituted heteroaryl, heterocyclic and substituted heterocyclic, and substituted alkynyl groups having amino groups blocked by conventional blocking groups such as Boc, Cbz, formyl, and the like, and alkynyl/substituted alkynyl groups substituted with —SO₂-alkyl, —SO₂-substituted alkyl, —SO₂-alkenyl, —SO₂-substituted alkenyl, —SO₂-cycloalkyl, —SO₂-substituted cycloalkyl, —SO₂-aryl, —SO₂-substituted aryl, —SO₂-heteroaryl, —SO₂-substituted heteroaryl, —SO₂-heterocyclic, —SO₂-substituted heterocyclic and —SO₂NRR where R is hydrogen or alkyl.

"Amidino" refers to the group

and the term "alkylamidino" refers to compounds having 1 to 3 alkyl groups (e.g.,

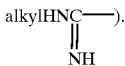

"Thioamidino" refers to the group

where R is hydrogen or alkyl.

"Aminoacyl" refers to the groups —NRC(O)alkyl, —NRC(O)substituted alkyl, —NRC(O)cycloalkyl, —NRC(O)substituted cycloalkyl, —NRC(O)alkenyl, —NRC(O)substituted alkenyl, —NRC(O)alkynyl, —NRC(O)substituted alkynyl, —NRC(O)aryl, —NRC(O)substituted aryl, —NRC(O)heteroaryl, —NRC(O)substituted heteroaryl, —NRC(O)heterocyclic, and —NRC(O)substituted heterocyclic where R is hydrogen or alkyl, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonyloxy" refers to the groups —NRC(O)O-alkyl, —NRC(O)O-substituted alkyl, —NRC(O)O-alkenyl, —NRC(O)O-substituted alkenyl, —NRC(O)O-alkynyl, —NRC(O)O-substituted alkynyl, —NRC(O)O-cycloalkyl, —NRC(O)O-substituted cycloalkyl, —NRC(O)O-aryl, —NRC(O)O-substituted aryl, —NRC(O)O-heteroaryl, —NRC(O)O-substituted heteroaryl, —NRC(O)O-heterocyclic, and —NRC(O)O-substituted heterocyclic where R is hydrogen or alkyl, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Oxycarbonylamino" refers to the groups —OC(O)NH₂, —OC(O)NRR, —OC(O)NR-alkyl, —OC(O)NR-substituted alkyl, —OC(O)NR-alkenyl, —OC(O)NR-substituted alkenyl, —OC(O)NR-alkynyl, —OC(O)NR-substituted alkynyl, —OC(O)NR-cycloalkyl, —OC(O)NR-substituted cycloalkyl, —OC(O)NR-aryl, —OC(O)NR-substituted aryl, —OC(O)NR-heteroaryl, —OC(O)NR-substituted heteroaryl, —OC(O)NR-heterocyclic, and —C(O)NR-substituted heterocyclic where R is hydrogen, alkyl or where each R is joined to form, together with the nitrogen atom, a heterocyclic or substituted heterocyclic ring, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Oxythiocarbonylamino" refers to the groups —OC(S)NH₂, —OC(S)NRR, —OC(S)NR-alkyl, —OC(S)NR-substituted alkyl, —OC(S)NR-alkenyl, —OC(S)NR-substituted alkenyl, —OC(S)NR-alkynyl, —OC(S)NR-substituted alkynyl, —OC(S)NR-cycloalkyl, —OC(S)NR-substituted cycloalkyl, —OC(S)NR-aryl, —OC(S)NR-substituted aryl, —OC(S)NR-heteroaryl, —OC(S)NR-substituted heteroaryl, —OC(S)NR-heterocyclic, and —OC(S)NR-substituted heterocyclic where R is hydrogen or allyl, or where each R is joined to form, together with the nitrogen atom, a heterocyclic or substituted heterocyclic ring, and wherein alkyl, substituted alkyl, alkenyl, substituted alkenyl, alkynyl, substitute-d alkynyl, cycloalkyl, substituted cycloalkyl, aryl, substituted aryl, heteroaryl, substituted heteroaryl, heterocyclic and substituted heterocyclic are as defined herein.

"Aminocarbonylamino" refers to the groups —NRC(O)NRR, —NRC(O)NR-alkyl, —NRC(O)NR-substituted alkyl, —NRC(O)NR-alkenyl, —NRC(O)NR-substituted alkenyl, —NRC(O)NR-alkynyl, —NRC(O)NR-substituted alkynyl, —NRC(O)NR-aryl, —NRC(O)NR-substituted aryl, —NRC(O)NR-cycloalkyl, —NRC(O)NR-substituted cycloalkyl, —NRC(O)NR-heteroaryl, —NRC(O)NR-substituted heteroaryl, —NRC(O)NR-heterocyclic, and —NRC(O)NR-substituted heterocyclic where each R is independently hydrogen or alkyl, or where each R is joined to form, together with the nitrogen atom, a heterocyclic or substituted heterocyclic ring, as well as where one of the amino groups is blocked by conventional blocking groups such as Boc, Cbz, formyl, and the like, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminothiocarbonylamino" refers to the groups —NRC(S)NRR, —NRC(S)NR-alkyl, —NRC(S)NR-substituted alkyl, —NRC(S)NR-alkenyl, —NRC(S)NR-substituted alkenyl, —NRC(S)NR-alkynyl, —NRC(S)NR-substituted alkynyl, —NRC(S)NR-aryl, —NRC(S)NR-substituted aryl, —NRC(S)NR-cycloalkyl, —NRC(S)NR-substituted cycloalkyl, —NRC(S)NR-heteroaryl, —NRC(S)NR-substituted heteroaryl, —NRC(S)NR-heterocyclic, and —NRC(S)NR-substituted heterocyclic where each R is independently hydrogen or alkyl, or where each R is joined to form, together with the nitrogen atom, a heterocyclic or substituted heterocyclic ring, as well as where one of the amino groups is blocked by conventional blocking groups such as Boc, Cbz, formyl, and the like, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aryl" or "Ar" refers to an unsaturated aromatic carbocyclic group of from 6 to 14 carbon atoms having a single ring (e.g., phenyl) or multiple condensed rings (e.g., naphthyl or anthryl), which condensed rings may or may not be aromatic (e.g., 2-benzoxazolinone, 2H-1,4-benzoxazin-3(4H)-one-7yl, and the like). Preferred aryls include phenyl and naphthyl.

"Substituted aryl" refers to aryl groups which are substituted with from 1 to 3 substituents selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxylamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, oxycarbonylamino, oxythiocarbonylamino, —S(O)$_2$-alkyl, —S(O)$_2$-substituted alkyl, —S(O)$_2$-cycloalkyl, —S(O)$_2$-substituted cycloalkyl, —S(O)$_2$-alkenyl, —S(O)$_2$-substituted alkenyl, —S(O)$_2$-aryl, —S(O)$_2$-substituted aryl, —S(O)$_2$-heteroaryl, —S(O)$_2$-substituted heteroaryl, —S(O)$_2$-heterocyclic, —S(O)$_2$-substituted heterocyclic, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic and —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from alkyl, substituted alkyl, aryl, substituted aryl, heteroaryl, substituted heteroaryl, heterocyclic and substituted heterocyclic, and amino groups on the substituted aryl blocked by conventional blocking groups such as Boc, Cbz, formyl, and the like, or substituted with —SO$_2$NRR where R is hydrogen or alkyl.

"Aryloxy" refers to the group aryl-O— which includes, by way of example, phenoxy, naphthoxy, and the like.

"Substituted aryloxy" refers to substituted aryl-O— groups.

"Aryloxyaryl" refers to the group -aryl-O-aryl

"Substituted aryloxyaryl" refers to aryloxyaryl groups substituted with from 1 to 3 substituents on either or both aryl rings selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxylamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, oxycarbonylamino, oxythiocarbonylamino, —S(O)$_2$-alkyl, —S(O)$_2$-substituted alkyl, —S(O)$_2$-cycloalkyl, —S(O)$_2$-substituted cycloalkyl, —S(O)$_2$-alkenyl, —S(O)$_2$-substituted alkenyl, —S(O)$_2$-aryl, —S(O)$_2$-substituted aryl, —S(O)$_2$-heteroaryl, —S(O)$_2$-substituted heteroaryl, —S(O)$_2$-heterocyclic, —S(O)$_2$-substituted heterocyclic, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic and —NRS(O)$_2$—NR-substituted heterocyclic where R is hydrogen or allyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from alkyl, substituted alkyl, aryl, substituted aryl, heteroaryl, substituted heteroaryl, heterocyclic and substituted heterocyclic, and amino groups on the substituted aryl blocked by conventional blocking groups such as Boc, Cbz, formyl, and the like, or substituted with —SO$_2$NRR where R is hydrogen or alkyl.

"Cycloalkyl" refers to cyclic alkyl groups of from 3 to 8 carbon atoms having a single cyclic ring including, by way of example, cyclopropyl, cyclobutyl, cyclopentyl, cyclooctyl and the like. Excluded from this definition are multi-ring alkyl groups such as adamantanyl, etc.

"Cycloalkenyl" refers to cyclic alkenyl groups of from 3 to 8 carbon atoms having single or multiple unsaturation but which are not aromatic.

"Substituted cycloalkyl" and "substituted cycloalkenyl" refer to cycloalkyl and cycloalkenyl groups, preferably of from 3 to 8 carbon atoms, having from 1 to 5 substituents selected from the group consisting of oxo (=O), thioxo (=S), alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic and —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from alkyl, substituted alkyl, aryl, substituted aryl, heteroaryl, substituted heteroaryl, heterocyclic and substituted heterocyclic, and substituted alkynyl groups having amino groups blocked by conventional blocking groups such as Boc, Cbz, formyl, and the like, and alkynyl/substituted alkynyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

"Cycloalkoxy" refers to —O-cycloalkyl groups.

"Substituted cycloalkoxy" refers to —O-substituted cycloalkyl groups.

"Guanidino" refers to the groups —NRC(=NR)NRR, —NRC(=NR)NR-alkyl, —NRC(=NR)NR-substituted alkyl, —NRC(=NR)NR-alkenyl, —NRC(=NR)NR-substituted alkenyl, —NRC(=NR)NR-alkynyl, —NRC(=NR)NR-substituted alkynyl, —NRC(=NR)NR-aryl, —NRC(=NR)NR-substituted aryl, —NRC(=NR)NR-cycloalkyl, —NRC(=NR)NR-substituted cycloalkyl, —NRC(=NR)NR-heteroaryl, —NRC(=NR)NR-substituted heteroaryl, —NRC(=NR)NR-heterocyclic, and —NRC(=NR)NR-substituted heterocyclic where each R is independently hydrogen and alkyl, as well as where one of the amino groups is blocked by conventional blocking groups such as Boc, Cbz, formyl, and the like, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Guanidinosulfone" refers to the groups —NRC(=NR)NRSO$_2$-alkyl, —NRC(=NR)NRSO$_2$-substituted alkyl, —NRC(=NR)NRSO$_2$-alkenyl, —NRC(=NR)NRSO$_2$-substituted alkenyl, —NRC(=NR)NRSO$_2$-alkynyl, —NRC(=NR)NRSO$_2$-substituted alkynyl, —NRC(=NR)NRSO$_2$-aryl, —NRC(=NR)NRSO$_2$-substituted aryl, —NRC(=NR)NRSO$_2$-cycloalkyl, —NRC(=NR)NRSO$_2$-substituted cycloalkyl, —NRC(=NR)NRSO$_2$-heteroaryl, —NRC(=NR)NRSO$_2$-substituted heteroaryl, —NRC(=NR)NRSO$_2$-heterocyclic, and —NRC(=NR)NRSO$_2$-substituted heterocyclic where each R is independently hydrogen and alkyl, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Halo" or "halogen" refers to fluoro, chloro, bromo and iodo and preferably is either chloro or bromo.

"Heteroaryl" refers to an aromatic carbocyclic group of from 2 to 10 carbon atoms and 1 to 4 heteroatoms selected from oxygen, nitrogen and sulfur within the ring. Such heteroaryl groups can have a single ring (e.g., pyridyl or furyl) or multiple condensed rings (e.g., indolizinyl or benzothienyl). Preferred heteroaryls include pyridyl, pyrrolyl, indolyl and furyl.

"Substituted heteroaryl" refers to heteroaryl groups which are substituted with from 1 to 3 substituents selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxylamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, oxycarbonylamino, oxythiocarbonylamino, —S(O)$_2$-alkyl, —S(O)$_2$-substituted alkyl, —S(O)$_2$-cycloalkyl, —S(O)$_2$-substituted cycloalkyl, —S(O)$_2$-alkenyl, —S(O)$_2$-substituted alkenyl, —S(O)$_2$-aryl, —S(O)$_2$-substituted aryl, —S(O)$_2$-heteroaryl, —S(O)$_2$-substituted heteroaryl, —S(O)$_2$-heterocyclic, —S(O)$_2$-substituted heterocyclic, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted allyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic and —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from alkyl, substituted alkyl, aryl, substituted aryl, heteroaryl, substituted heteroaryl, heterocyclic and substituted heterocyclic, and amino groups on the substituted aryl blocked by conventional blocking groups such as Boc, Cbz, formyl, and the like, or substituted with —SO$_2$NRR where R is hydrogen or alkyl.

"Heteroaryloxy" refers to the group —O-heteroaryl and "substituted heteroaryloxy" refers to the group —O-substituted heteroaryl.

"Heterocycle" or "heterocyclic" refers to a saturated or unsaturated group having a single ring or multiple condensed rings having from 1 to 10 carbon atoms and from 1 to 4 hetero atoms selected from nitrogen, sulfur or oxygen within the ring wherein, in fused ring systems, one or more the rings can be aryl or heteroaryl.

"Saturated heterocyclic" refers to heterocycles of single or multiple condensed rings lacking unsaturation in any ring (e.g., carbon to carbon unsaturation, carbon to nitrogen unsaturation, nitrogen to nitrogen unsaturation, and the like).

"Unsaturated heterocyclic" refers to non-aromatic heterocycles of single or multiple condensed rings having unsaturation in any ring (e.g., carbon to carbon unsaturation, carbon to nitrogen unsaturation, nitrogen to nitrogen unsaturation, and the like).

"Substituted heterocyclic" refers to heterocycle groups which are substituted with from 1 to 3 substituents selected from the group consisting of oxo (=O), thioxo (=S), alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxylcycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic and —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from alkyl, substituted alkyl, aryl, substituted aryl, heteroaryl, substituted heteroaryl, heterocyclic and substituted heterocyclic, and substituted alkynyl groups having amino groups blocked by conventional blocking groups such as Boc, Cbz, formyl, and the like, and alkynyl/substituted alkynyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

Examples of heterocycles and heteroaryls include, but are not limited to, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholino, thiomorpholino, piperidinyl, pyrrolidine, tetrahydrofuranyl, and the like.

"Saturated substituted heterocyclic" refers to substituted heterocycles of single or multiple condensed rings lacking unsaturation in any ring (e.g., carbon to carbon unsaturation, carbon to nitrogen unsaturation, nitrogen to nitrogen unsaturation, and the like).

"Unsaturated substituted heterocyclic" refers to non-aromatic substituted heterocycles of single or multiple condensed rings having unsaturation in any ring (e.g., carbon to carbon unsaturation, carbon to nitrogen unsaturation, nitrogen to nitrogen unsaturation, and the like).

"Heterocyclyloxy" refers to the group —O-heterocyclic and "substituted heterocyclyloxy" refers to the group —O-substituted heterocyclic.

"Thiol" refers to the group —SH,

"Thioalkyl" refers to the groups —S-alkyl

"Substituted thioalkyl" refers to the group —S-substituted alkyl.

"Thocycloalkyl" refers to the groups —S-cycloalkyl.

"Substituted thiocycloalkyl" refers to the group —S-substituted cycloalkyl.

"Thioaryl" refers to the group —S-aryl and "substituted thioaryl" refers to the group —S-substituted aryl.

"Thioheteroaryl" refers to the group —S-heteroaryl and "substituted thioheteroaryl" refers to the group —S-substituted heteroaryl.

"Thioheterocyclic" refers to the group —S-heterocyclic and "substituted thioheterocyclic" refers to the group —S-substituted heterocyclic.

"Pharmaceutically acceptable salt" refers to pharmaceutically acceptable salts of a compound of formula I or IA, which salts are derived from a variety of organic and inorganic counter ions well known in the art and include, by way of example only, sodium, potassium, calcium, magnesium, ammonium, tetraalkylammonium, and the like; and when the compound of formula I or IA contains a basic functionality, salts of organic or inorganic acids, such as hydrochloride, hydrobromide, tartrate, mesylate, acetate, maleate, oxalate and the like.

Compound Preparation

The compounds of this invention can be prepared from readily available starting materials using the following general methods and procedures. It will be appreciated that where topical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, *Protecting Groups in Organic Synthesis*, Second Edition, Wiley, New York, 1991, and references cited therein.

Furthermore, the compounds of this invention will typically contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of His invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

In a preferred method of synthesis, the compounds of formulas I and IA, wherein Q is —C(O)NR$^7$—, are prepared by first coupling an amino acid of formula II:

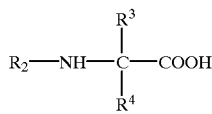

II wherein R$^2$ and R$^3$ are as defined in formulas I and IA, and R$^4$ is hydrogen, with a sulfonyl chloride of formula III:

III wherein R$^1$ is as defined in formulas I and IA, to provide an N-sulfonyl amino acid of formula IV:

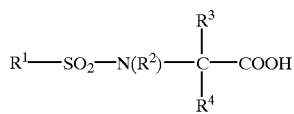

IV wherein R$^1$–R$^4$ are as defined above.

This reaction is typically conducted by reacting the amino acid of formula II with at least one equivalent, preferably about 1.1 to about 2 equivalents, of sulfonyl chloride III in an inert diluent such as dichloromethane and the like. Generally, the reaction is conducted at a temperature ranging from about –70° C. to about 40° C. for about 1 to about 24 hours. Preferably, this reaction is conducted in the presence of a suitable base to scavenge the acid generated during the reaction. Suitable bases include, by way of example, tertiary amines, such as triethylamine, diisopropylethylamine, N-methylmorpholine and the like. Alternatively, the reaction can be conducted under Schotten-Daumann-type conditions using aqueous alkali, such as sodium hydroxide and the like, as the base. Upon completion of the reaction, the resulting N-sulfonyl amino acid IV is recovered by conventional methods including neutralization, extraction, precipitation, chromatography, filtration and the like.

The amino acids of formula II employed in the above reaction are either known compounds or compounds that can be prepared from known compounds by conventional synthetic procedures. Examples of suitable amino acids for use in this reaction include, but are not limited to, L-proline, trans4-hydroxyl-L-proline, cis-4-hydroxyl-L-proline, trans-3-phenyl-L-proline, cis-3-phenyl-L-proline, L-(2-methyl) proline, L-pipecolinic acid, L-indoline-2-carboxylic acid, L-1,2,3,4-tetrahydroisoquinoline-3-carboxylic acid, L-thiazolidine-4-carboxylic acid, L-(5,5-dimethyl) thiazolidine-4-carboxylic acid, L-thiamorpholine-3-carboxylic acid, glycine, 2-tert-butylglycine, D,L-phenylglycine, L-alanine, α-methylalanine, N-methyl-L-phenylalanine, L-diphenylalanine, sarcosine, D,L-phenylsarcosine, L-aspartic acid β-tert-butyl ester, L-glutamic acid γ-tert-butyl ester, L-(O-benzyl)serine, 1-aminocyclopropanecarboxylic acid, 1-aminocyclobutanecarboxylic acid, 1-aminocyclopentanecarboxylic acid (cycloleucine) 1-aminocyclohexanecarboxylic acid, L-serine and the like. If desired, the corresponding carboxylic acid esters of the amino acids of formula II, such as the methyl esters, ethyl esters and the like, can be employed in the above reaction with the sulfonyl chloride III. Subsequent hydrolysis of the ester group to the carboxylic acid using conventional reagents and conditions, i.e., treatment with an alkali metal hydroxide in an inert diluent such as methanol/water, then provides the N-sulfonyl amino acid IV.

Similarly, the sulfonyl chlorides of formula HI employed in the above reaction are either known compounds or compounds that can be prepared from known compounds by conventional synthetic procedures. Such compounds are typically prepared from the corresponding sulfonic acid, i.e., from compounds of the formula R$^1$—SO$_3$H where R$^1$ is as defined above, using phosphorous trichloride and phosphorous pentachloride. This reaction is generally conducted by contacting the sulfonic acid with about 2 to 5 Be molar equivalents of phosphorous trichloride and phosphorous pentachloride, either neat or in an inert solvent, such as dichloromethane, at a temperature in the range of about 0° C. to about 80° C. for about 1 to about 48 hours to afford the sulfonyl chloride. Alternatively, the sulfonyl chlorides of formula III can be prepared from the corresponding thiol compound, i.e., from compounds of the formula R$^1$—SH where R$^1$ is as defined above, by treating the thiol with chlorine (Cl$_2$) and water under conventional reaction conditions.

Examples of sulfonyl chlorides suitable for use in this invention include, but are not limited to, methanesulfonyl chloride, 2-propanesulfonyl chloride, 1-butanesulfonyl chloride, benzenesulfonyl chloride, 1-naphthalenesulfonyl chloride, 2-naphthalenesulfonyl chloride, p-toluenesulfonyl chloride, α-toluenesulfonyl chloride, 4-acetamidobenzenesulfonyl chloride, 4-amidinobenzenesulfonyl chloride, 4-tert-butylbenzenesulfonyl chloride, 4-bromobenzenesulfonyl chloride, 2-carboxybenzenesulfonyl chloride, 4-cyanobenzenesulfonyl chloride, 3,4-dichlorobenzenesulfonyl chloride, 3,5-dichlorobenzenesulfonyl chloride, 3,4-dimethoxybenzenesulfonyl chloride, 3,5- ditrifluoromethylbenzenesulfonyl chloride, 4-fluorobenzenesulfonyl chloride, 4-methoxybenzenesulfonyl chloride, 2-methoxycarbonylbenzenesulfonyl chloride, 4-methylamidobenzenesulfonyl chloride, 4-nitrobenzenesulfonyl chloride, 4-thioamidobenzenesulfonyl chloride, 4-trifluoromethylbenzenesulfonyl chloride, 4-trifluoromethoxybenzenesulfonyl chloride, 2,4,6-trimethylbenzenesulfonyl chloride, 2-phenylethanesulfonyl chloride, 2-thiophenesulfonyl chloride, 5-chloro-2-thiophenesulfonyl chloride, 2,5-dichloro-4-thiophenesulfonyl chloride, 2-thiazolesulfonyl chloride, 2-methyl-4-tiiazolesulfonyl chloride, 1-methyl-4-imidazolesulfonyl chloride, 1-methyl-4-pyrazolesulfonyl chloride, 5-chloro-1,3-dimethyl-4-pyrazolesulfonyl chloride, 3-pyridinesulfonyl chloride, 2-pyrimidinesulfonyl chloride and the like. If desired, a sulfonyl fluoride, sulfonyl bromide or sulfonic acid anhydride may be used in place of the sulfonyl chloride in the above reaction to form the N-sulfonyl amino acids of formula IV.

The compounds of formula I are then prepared by coupling the intermediate N-sulfonyl amino acid of formula IV with an amino acid derivative of formula VI:

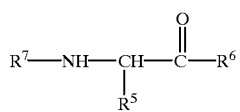

VI wherein $R^5$–$R^7$ are as in formulas I and IA. This coupling reaction is typically conducted using well-known coupling reagents such as carbodiimides, BOP reagent (benzotriazol-1-yloxy-tris(dimethylamino)phosphonium hexafluorophosphonate) and the like. Suitable carbodiimides include, by way of example, dicyclohexylcarbodiimide (DCC), 1-(3-dimethylaminopropyl)-3-ethylcarbodiimide (EDC) and the like. If desired, polymer supported forms of carbodiimide coupling reagents may also be used including, for example, those described in *Tetrahedron Letters,* 34(48), 7685 (1993). Additionally, well-known coupling promoters, such as N-hydroxysuccinimide, 1-hydroxybenzotriazole and the like, may be used to facilitate the coupling reaction.

This coupling reaction is typically conducted by contacting the N-sulfonylamino acid IV with about 1 to about 2 equivalents of the coupling reagent and at least one equivalent, preferably about 1 to about 1.2 equivalents, of amino acid derivative VI in an inert diluent, such as dichloromethane, chloroform, acetonitrile, tetrahydrofuran, N,N-dimethylformamide and the like. Generally, this reaction is conducted at a temperature ranging from about 0° C. to about 37° C. for about 12 to about 24 hours. Upon completion of the reaction, the compound of formula I is recovered by conventional methods including neutralization, extraction, precipitation, chromatography, filtration, and the like.

Alternatively, the N-sulfonyl amino acid IV can be converted into an acid halide and the acid halide coupled with amino acid derivative VI to provide compounds of formula I. The acid halide of VI can be prepared by contacting VI with an inorganic acid halide, such as thionyl chloride, phosphorous trichloride, phosphorous tribromide or phosphorous pentachloride, or, preferably, with oxalyl chloride under conventional conditions. Generally, this reaction is conducted using about 1 to 5 molar equivalents of the inorganic acid halide or oxalyl chloride, either neat or in an inert solvent, such as dichloromethane or carbon tetrachloride, at temperature in the range of about 0° C. to about 80° C. for about 1 to about 48 hours. A catalyst, such as N,N-dimethylformamide, may also be used in this reaction.

The acid halide of N-sulfonyl amino acid IV is then contacted with at least one equivalent, preferably about 1.1 to about 1.5 equivalents, of amino acid derivative VI in an inert diluent, such as dichloromethane, at a temperature ranging from about −70° C. to about 40° C. for about 1 to about 24 hours. Preferably, this reaction is conducted in the presence of a suitable base to scavenge the acid generated during the reaction. Suitable bases include, by way of example, tertiary amines, such as triethylamine, diisopropylethylamine, N-methylmorpholine and the like. Alternatively, the reaction can be conducted under Schotten-Baumann-type conditions using aqueous alkali, such as sodium hydroxide and the like. Upon completion of the reaction, the compound of formula I is recovered by conventional methods including neutralization, extraction, precipitation, chromatography, filtration, and the like.

Alternatively, the compounds of formula I can be prepared by first forming a diamino acid derivative of formula VII:

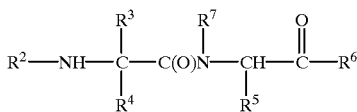

VII wherein $R^2$–$R^7$ are as defined above. The diamino acid derivatives of formula VII can be readily prepared by coupling an amino acid of formula II with an amino acid derivative of formula VI using conventional amino acid coupling techniques and reagents, such as carbodiimides, BOP reagent and the like, as described above. Diamino acid VII can then be sulfonated using a sulfonyl chloride of formula III and using the synthetic procedures described above to provide a compound of formula I.

The amino acid derivatives of formula VI employed in the above reactions are either known compounds or compounds that can be prepared from known compounds by conventional synthetic procedures. For example, amino acid derivatives of formula VI can be prepared by C-alkylating commercially available diethyl 2-acetamidomalonate (Aldrich, Milwaukee, Wis., USA) with an alkyl or substituted alkyl halide. This reaction is typically conducted by treating the diethyl 2-acetamidomalonate with at least one equivalent of sodium ethoxide and at least one equivalent of an alkyl or substituted alkyl halide in refluxing ethanol for about 6 to about 12 hours. The resulting C-alkylated malonate is then deacetylated, hydrolyzed and decarboxylated by heating in aqueous hydrochloric acid at reflux for about 6 to about 12 hours to provide the amino acid, typically as the hydrochloride salt.

Examples of amino acid derivatives of formula VI suitable for use in the above reactions include, but are not limited to, L-tryptophan methyl ester, L-phenylalanine methyl ester, L-phenylalanine isopropyl ester, L-phenylalanine benzyl ester, L-phenylalaninamide, N-methyl-L-phenylalanine benzyl ester, D,L-homophenylalanine methyl ester, β-(1-naphthyl)-L-alanine methyl ester, β-(2-naphthyl)-L-alanine methyl ester, β-(2-thienyl)-L-alanine methyl ester, β-(2-pyridyl)-L-alanine methyl ester, β-(3-pyridyl)-L-alanine methyl ester, β-(4-pyridyl)-L-alanine methyl ester, β-(2-thiazolyl)-D,L-alanine methyl ester, β-(1,2,4-triazol-3-yl)-D,L-alanine methyl ester, and the like. If desired, of course, other esters or amides of the above-described compounds may also be employed.

For ease of synthesis, the compounds of formula I are typically prepared as an ester, i.e., where $R^6$ is an alkoxy or substituted alkoxy group and the like. If desired, the ester group can be hydrolysed using conventional conditions and reagents to provide the corresponding carboxylic acid. Typically, this reaction is conducted by treating the ester with at least one equivalent of an alkali metal hydroxide, such as lithium, sodium or potassium hydroxide, in an inert diluent, such as methanol or mixtures of methanol and water, at a temperature ranging from about 0° C. to about 24° C. for about 1 to about 12 hours. Alternatively, benzyl esters may be removed by hydrogenolysis using a palladium catalyst, such as palladium on carbon. The resulting carboxylic acids may be coupled, if desired, to amines such as β-alanine ethyl ester, hydroxyamines such as hydroxylamine and N-hydroxysuccinimide, alkoxyamines and substituted alkoxyamines such as O-methylhydroxylamine and O-benzylhydroxylamine, and the like, using conventional coupling reagents and conditions as described above.

As will be apparent to those skilled in the art, other functional groups present on any of the substituents of the compounds of formula I can be readily modified or derivatized either before or after the above-described coupling reactions using well-known synthetic procedures. For example, a nitro group present on a substituent of a compound of formula I or an intermediate thereof may be readily reduced by hydrogenation in the presence of a palladium catalyst, such as palladium on carbon, to provide the corresponding amino group. This reaction is typically conducted at a temperature of from about 20° C. to about 50° C. for about 6 to about 24 hours in an inert diluent, such as methanol. Compounds having a nitro group on the $R^5$ substituent can be prepared, for example, by using a 4-nitrophenylalanine derivative and the like in the above-described coupling reactions.

Similarly, a pyridyl group can be hydrogenated in the presence of a platinum catalyst, such as platinum oxide, in an acidic diluent to provide the corresponding piperidinyl analogue. Generally, this reaction is conducted by treating the pyridine compound with hydrogen at a pressure ranging from about 20 psi to about 60 psi, preferably about 40 psi, in the presence of the catalyst at a temperature of about 20° C. to about 50° C. for about 2 to about 24 hours in an acidic diluent, such as a mixture of methanol and aqueous hydrochloric acid. Compounds having a pyridyl group can be readily prepared by using, for example, β-(2-pyridyl)-, β-(3-pyridyl)- or β-(4-pyridyl)-L-alanine derivatives in the above-described coupling reactions.

By way of illustration, a compound of formula I, or an intermediate thereof, having a substituent containing a primary or secondary amino group, such as where $R^1$ is a 4-aminophenyl group, can be readily N-acylated using conventional acylating reagents and conditions to provide the corresponding amide. This acylation reaction is typically conducted by treating the amino compound with at least one equivalent, preferably about 1.1 to about 1.2 equivalents, of a carboxylic acid in the presence of a coupling reagent such as a carbodiimide, BOP reagent (benzotriazol-1-yloxy-tris (dimethylamino)phosphonium hexafluorophosphonate) and the like, in an inert diluent, such as dichloromethane, chloroform, acetonitrile, tetrahydrofuran, N,N-dimethylformamide and the like, at a temperature ranging from about 0° C. to about 37° C. for about 4 to about 24 hours. Preferably, a promoter, such as N-hydroxysuccinimide, 1-hydroxybenzotriazole and the like, is used to facilitate the acylation reaction. Examples of carboxylic acids suitable for use in this reaction include, but are not limited to, N-tert-butyloxycarbonylglycine, N-tert-butyloxycarbonyl-L-phenylalanine, N-tert-butyloxycarbonyl-L-aspartic acid benzyl ester, benzoic acid, N-tert-butyloxycarbonylisonipecotic acid, N-methylisonipecotic acid, N-tert-butyloxycarbonylnipecotic acid, N-tert-butyloxycarbonyl-L-tetrahydroisoquinoline-3-carboxylic acid, N-(toluene-4-sulfonyl)-L-proline and the like.

Alternatively, a compound of formula I or an intermediate thereof containing a primary or secondary amino group can be N-acylated using an acyl halide or a carboxylic acid anhydride to form the corresponding amide. This reaction is typically conducted by contacting the amino compound with at least one equivalent, preferably about 1.1 to about 1.2 equivalents, of the acyl halide or carboxylic acid anhydride in an inert diluent, such as dichloromethane, at a temperature ranging from about −70° C. to about 40° C. for about 1 to about 24 hours. If desired, an acylation catalyst such as 4-(N,N-dimethylamino)pyridine may be used to promote the acylation reaction. The acylation reaction is preferably conducted in the presence of a suitable base to scavenge the acid generated during the reaction. Suitable bases include, by way of example, tertiary amines, such as triethylamine, diisopropylethylamine, N-methylmorpholine and the like. Alternatively, the reaction can be conducted under Schotten-Baumann-type conditions using aqueous alkali, such as sodium hydroxide and the like.

Examples of acyl halides and carboxylic acid anhydrides suitable for use in this reaction include, but are not limited to, 2-methylpropionyl chloride, trimethylacetyl chloride, phenylacetyl chloride, benzoyl chloride, 2-bromobenzoyl chloride, 2-methylbenzoyl chloride, 2-trifluoromethylbenzoyl chloride, isonicotinoyl chloride, nicotinoyl chloride, picolinoyl chloride, acetic anhydride, succinic anhydride and the like. Carbamyl chlorides, such as N,N-dimethylcarbamyl chloride, N,N-diethylcarbamyl chloride and the like, can also be used in this reaction to provide ureas. Similarly, dicarbonates, such as di-tert-butyl dicarbonate, may be employed to provide carbamates.

In a similar manner, a compound of formula I or an intermediate thereof containing a primary or secondary amino group may be N-sulfonated to form a sulfonamide using a sulfonyl halide or a sulfonic acid anhydride. Sulfonyl halides and sulfonic acid anhydrides suitable for use in this reaction include, but are not limited to, methanesulfonyl chloride, chloromethanesulfonyl chloride, p-toluenesulfonyl chloride, trifluoromethanesulfonic anhydride and the like. Similarly, sulfamoyl chlorides, such as dimethylsulfamoyl chloride, can be used to provide sulfamides (e.g., >N—$SO_2$—N<).

Additionally, a primary and secondary amino group present on a substituent of a compound of formula I, or an intermediate thereof, can be reacted with an isocyanate or a thioisocyanate to give a urea or thiourea, respectively. This reaction is typically conducted by contacting the amino compound with at least one equivalent, preferably about 1.1 to about 1.2 equivalents, of the isocyanate or thioisocyanate in an inert diluent, such as toluene and the like, at a temperature ranging from about 24° C. to about 37° C. for about 12 to about 24 hours. The isocyanates and thioisocyanates used in this reaction are commercially available or can be prepared from commercially available compounds using well-known synthetic procedures. For example, isocyanates and thioisocyanates are readily prepared by reacting the appropriate amine with phosgene or thiophosgene. Examples of isocyanates and thioisocyanates suitable for use in this reaction include, but are not limited to, ethyl isocyanate, n-propyl isocyanate, 4-cyanophenyl isocyanate, 3-methoxyphenyl isocyanate, 2-phenylethyl isocyanate, methyl thioisocyanate, ethyl thioisocyanate, 2-phenylethyl thioisocyanate, 3-phenylpropyl thioisocyanate, 3-(N,N-diethylamino)propyl thioisocyanate, phenyl thioisocyanate, benzyl thioisocyanate, 3-pyridyl thioisocyanate, fluorescein isothiocyanate (isomer I), and the like.

Furthermore, when a compound of formula I or an intermediate thereof contains a primary or secondary amino group, the amino group can be reductively alkylated using aldehydes or ketones to form a secondary or tertiary amino group. This reaction is typically conducted by contacting the amino compound with at least one equivalent, preferably about 1.1 to about 1.5 equivalents, of an aldehyde or ketone and at least one equivalent based on the amino compound of a metal hydride reducing agent, such as sodium cyanoborohydride, in an inert diluent, such as methanol, tetrahydrofuran, mixtures thereof and the like, at a temperature ranging from about 0° C. to about 50° C. for about 1 to about 72 hours. Aldehydes and ketones suitable for use in this reaction include, by way of example, benzaldehyde, 4-chlorobenzaldehyde, valeraldehyde and the like.

In a similar manner, when a compound of formula I, or an intermediate thereof, has a substituent containing a hydroxyl group, the hydroxyl group can be further modified or derivatized either before or after the above coupling reactions to provide, by way of example, ethers, carbamates and the like.

By way of example, a compound of formula I or an intermediate thereof having a substituent containing a hydroxyl group, such as where RI is a 4-hydroxyphenyl group, can be readily O-alkylated to form ethers. This O-alkylation reaction is typically conducted by contacting the hydroxy compound with a suitable alkali or alkaline earth metal base, such as potassium carbonate, in an inert diluent, such as acetone, 2-butanone and the like, to form the alkali or alkaline earth metal salt of the hydroxyl group. This salt is generally not isolated, but is reacted in situ with at least one equivalent of an alkyl or substituted alkyl halide or sulfonate, such as an alkyl chloride, bromide, iodide, mesylate or tosylate, to afford the ether. Generally, this reaction is conducted at a temperature ranging from about 60° C. to about 150° C. for about 24 to about 72 hours. Preferably, a catalytic amount of sodium or potassium iodide is added to the reaction mixture when an alkyl chloride or bromide is employed in the reaction.

Examples of alkyl or substituted alkyl halides and sulfonates suitable for use in this reaction include, but are not limited to, tert-butyl bromoacetate, N-tert-butyl chloroacetamide, 1-bromoethylbenzene, ethyl α-bromophenylacetate, 2-(N-ethyl-N-phenylamino)ethyl chloride, 2-(N,N-ethylamino)ethyl chloride, 2-(N,N-diisopropylamino)ethyl chloride, 2-(N,N-dibenzylamino)ethyl chloride, 3-(N,N-ethylamino)propyl chloride, 3-(N-benzyl-N-methylamino)propyl chloride, N-(2-chloroethyl) morpholine, 2-(hexamethyleneimino)ethyl chloride, 3-(N-methylpiperazine)propyl chloride, 1-(3-chlorophenyl)-4-(3-chloropropyl)piperazine, 2-(4-hydroxy-4-phenylpiperidine) ethyl chloride, N-tert-butyloxycarbonyl-3-piperidinemethyl tosylate and the like.

Alternatively, a hydroxyl group present on a substituent of a compound of formula I, or an intermediate thereof, can be O-alkylated using the Mitsunobu reaction. In this reaction, ail alcohol, such as 3-(N,N-dimethylamino)-1-propanol and the like, is reacted with about 1.0 to about 1.3 equivalents of triphenylphosphine and about 1.0 to about 1.3 equivalents of diethyl azodicarboxylate in an inert diluent, such as tetrahydrofuran, at a temperature ranging from about −10° C. to about 5° C. for about 0.25 to about 1 hour. About 1.0 to about 1.3 equivalents of a hydroxy compound, such as N-tert-butyltyrosine methyl ester, is then added and the reaction mixture is stirred at a temperature of about 0° C. to about 30° C. for about 2 to about 48 hours to provide the O-alkylated product.

In a similar manner, a compound of formula I, or an intermediate thereof, containing an aryl hydroxy group can be reacted with an aryl iodide to provide a diaryl ether. Generally, this reaction is conducted by forming the alkali metal salt of the hydroxyl group using a suitable base, such as sodium hydride, in an inert diluent, such as xylenes, at a temperature of about −25° C. to about 10° C. The salt is then treated with about 1.1 to about 1.5 equivalents of cuprous bromide dimethyl sulfide complex at a temperature ranging from about 10° C. to about 30° C. for about 0.5 to about 2.0 hours, followed by about 1.1 to about 1.5 equivalents of an aryl iodide, such as sodium 2-iodobenzoate and the like. The reaction is then heated to a temperature from about 70° C. to about 150° C. for about 2 to about 24 hours to provide the diaryl ether.

Additionally, a hydroxy-containing compound can also be readily derivatized to form a carbamate. In one method for preparing such carbamates, a hydroxy compound of formula I, or an intermediate thereof, is contacted with about 1.0 to about 1.2 equivalents of 4-nitrophenyl chloroformate in an inert diluent, such as dichloromethane, at a temperature ranging from about −25° C. to about 0° C. for about 0.5 to about 2.0 hours. Treatment of the resulting carbonate with an excess, preferably about 2 to about 5 equivalents, of a trialkylamine, such as triethylamine, for about 0.5 to 2 hours, followed by about 1.0 to about 1.5 equivalents of a primary or secondary amine, provides the carbamate. Examples of amines suitable for using in this reaction include, but are not limited to, piperazine, 1-methylpiperazine, 1-acetylpiperazine, morpholine, thiomorpholine, pyrrolidine, piperidine and the like.

Alternatively, in another method for preparing carbamates, a hydroxy-containing compound is contacted with about 1.0 to about 1.5 equivalents of a carbamyl chloride in an inert diluent, such as dichloromethane, at a temperature ranging from about 25° C. to about 70° C. for about 2 to about 72 hours. Typically, this reaction is conducted in the presence of a suitable base to scavenge the acid generated during the reaction. Suitable bases include, by way of example, tertiary amines, such as triethylamine, diisopropylethylamine, N-methylmorpholine and the like. Additionally, at least one equivalent (based on the hydroxy compound) of 4-N,N-dimethylamino)pyridine is preferably added to the reaction mixture to facilitate the reaction. Examples of carbamyl chlorides suitable for use in this reaction include, by way of example, dimethylcarbamyl chloride, diethylcarbamyl chloride and the like.

Likewise, when a compound of formula I, or an intermediate thereof, contains a primary or secondary hydroxyl group, such hydroxyl groups can be readily converted into a leaving group and displaced to form, for example, amines, sulfides and fluorides. For example, derivatives of 4-hydroxy-L-proline can be converted into the corresponding 4-amino, 4-thio or 4-fluoro-L-proline derivatives via nucleophilic displacement of the derivatized hydroxyl group. Generally, when a chiral compound is employed in these reactions, the stereochemistry at the carbon atom attached to the derivatized hydroxyl group is typically inverted.

These reactions are typically conducted by first converting the hydroxyl group into a leaving group, such as a tosylate, by treatment of the hydroxy compound with at least one equivalent of a sulfonyl halide, such as p-toluenesulfonyl chloride and the like, in pyridine. This reaction is generally conducted at a temperature of from about 0° C. to about 70° C. for about 1 to about 48 hours. The resulting tosylate can then be readily displaced with sodium azide, for example, by contacting the tosylate with at least one equivalent of sodium azide in an inert diluent, such as a mixture of N,N-dimethylformamide and water, at a temperature ranging from about 0° C. to about 37° C. for about 1 to about 12 hours to provide the corresponding azido compound. The azido group can then be reduced by, for example, hydrogenation using a palladium on carbon catalyst to provide the amino (—$NH_2$) compound.

Similarly, a tosylate group can be readily displaced by a thiol to form a sulfide. This reaction is typically conducted by contacting the tosylate with at least one equivalent of a thiol, such as thiophenol, in the presence of a suitable base, such as 1,8-diazabicyclo[5.4.0]undec-7-ene (DBU), in an inert diluent, such as N,N-dimethylformamide, at a temperature of from about 0° C. to about 37° C. for about 1 to about 12 hours to provide the sulfide. Additionally, treatment of a tosylate with morpholinosulfur trifluoride in an inert diluent, such as dichloromethane, at a temperature ranging from about 0° C. to about 37° C. for about 12 to about 24 hours affords the corresponding fluoro compound.

Furthermore, a compound of formula I, or an intermediate thereof, having a substituent containing an iodoaryl group, for example, when $R^1$ is a 4-iodophenyl group, can be readily converted either before or after the above coupling reactions into a biaryl compound. Typically, this reaction is conducted by treating the iodoaryl compound with about 1.1 to about 2 equivalents of an arylzinc iodide, such as 2-(methoxycarbonyl)phenylzinc iodide, in the presence of a palladium catalyst, such as palladium tetra(triphenylphosphine), in an inert diluent, such as tetrahydrofuran, at a temperature ranging from about 24° C. to about 30° C. until the reaction is complete. This reaction is further described, for example, in Rieke, *J. Org. Chem.* 1991, 56, 1445.

In some cases, the compounds of formula I, or intermediates thereof, may contain substituents having one or more sulfur atoms. Such sulfur atoms will be present, for example, when the amino acid of formula II employed in the above reactions is derived from L-thiazolidine-4-carboxylic acid, L-(5,5-dimethyl)thiazolidine-4-carboxylic acid, L-thiamorpholine-3-carboxylic acid and the like. When present, such sulfur atoms can be oxidized either before or after the above coupling reactions to provide a sulfoxide or sulfone compound using conventional reagents and reaction conditions. Suitable reagents for oxidizing a sulfide compound to a sulfoxide include, by way of example, hydrogen peroxide, 3-chloroperoxybenzoic acid (MCPBA), sodium periodate and the like. The oxidation reaction is typically conducted by contacting the sulfide compound with about 0.95 to about 1.1 equivalents of the oxidizing reagent in an inert diluent, such as dichloromethane, at a temperature ranging from about −50° C. to about 75° C. for about 1 to about 24 hours. The resulting sulfoxide can then be further oxidized to the corresponding sulfone by contacting the sulfoxide with at least one additional equivalent of an oxidizing reagent, such as hydrogen peroxide, MCPBA, potassium permanganate and the like. Alternatively, the sulfone can be prepared directly by contacting the sulfide with at least two equivalents, and preferably an excess, of the oxidizing reagent. Such reactions are described further in March, *"Advanced Organic Chemistry"*, 4th Ed., pp. 1201–1202, Wiley Publisher (1992).

Lastly, the compounds of formula I, where Q is —C(S)$NR^7$—, can be prepared by using an amino thionoacid derivative in place of amino acid II in the above described synthetic procedures. Such amino thionoacid derivatives can be prepared by the procedures described in Shalaky, et al., *J. Org. Chem.*, 61:9045–9048 (1996) and Brain, et al., *J. Org. Chem.*, 62:3808–3809 (1997) and references cited therein.

Pharmaceutical Formulations

When employed as pharmaceuticals, the compounds of formula I and IA are usually administered in the form of pharmaceutical compositions. These compounds can be administered by a variety of routes including oral, rectal, transdermal, subcutaneous, intravenous, intramuscular, and intranasal. These compounds are effective as both injectable and oral compositions. Such compositions are prepared in a manner well known in the pharmaceutical art and comprise at least one active compound.

This invention also includes pharmaceutical compositions which contain, as the active ingredient, one or more of the compounds of formula I or IA above associated with pharmaceutically acceptable carriers. In making the compositions of this invention, the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound is effective over a wide dosage range and is generally administered in a pharmaceutically effective amount. It will be understood, however, that the amount of the compound actually administered will be determined by a physician in the light of the relevant circumstances, including the condition to be treated, the chosen route of administration, the actual compound administered, the age, weight, and response of the individual patient, the severity of the patient's symptoms and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions suitably flavored with syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably, the compositions are administered by the oral or nasal respiratory route for local or systemic effect. Compositions in preferably pharmaceutically acceptable solvents may be nebulized by use of inert gases. Nebulized solutions may be breathed directly from the nebulizing device or the nebulizing device may be attached to a face mask tent or intermittent positive pressure breathing machine. Solution, suspension, or powder compositions may be administered, preferably orally or nasally, from devices which deliver the formulation in an appropriate manner.

The following formulation examples illustrate the pharmaceutical compositions of the present invention.

Formulation Example 1

Hard gelatin capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatin capsules in 340 mg quantities.

Formulation Example 2

A tablet formula is prepared using the ingredients below:

| Ingredient | Quantity (mg/tablet) |
| --- | --- |
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation Example 3

A dry powder inhaler formulation is prepared containing the following components:

| Ingredient | Weight % |
| --- | --- |
| Active Ingredient | 5 |
| Lactose | 95 |

The active mixture is mixed with the lactose and the mixture is added to a dry powder inhaling appliance.

Formulation Example 4

Tablets, each containing 30 mg of active ingredient, are prepared as follows:

| Ingredient | Quantity (mg/tablet) |
| --- | --- |
| Active Ingredient | 30.0 mg |
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinyl-pyrrolidone is mixed with the resultant powders, which are then passed through a 16 mesh U.S. sieve. The granules so produced are dried at 50° to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 150 mg.

Formulation Example 5

Capsules, each containing 40 mg of medicament, are made as follows:

| Ingredient | Quantity (mg/capsule) |
| --- | --- |
| Active Ingredient | 40.0 mg |
| Starch | 109.0 mg |
| Magnesium stearate | 1.0 mg |
| Total | 150.0 mg |

The active ingredient, cellulose, starch, and magnesium stearate are blended, passed through a No. 20 mesh U.S. sieve, and filled into hard gelatin capsules in 150 mg quantities.

Formulation Example 6

Suppositories, each containing 25 mg of active ingredient, are made as follows:

| Ingredient | Amount |
| --- | --- |
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Example 7

Suspensions, each containing 50 mg of medicament per 5.0 ml dose, are made as follows:

| Ingredient | Amount |
| --- | --- |
| Active Ingredient | 50.0 mg |
| Xanthan gum | 4.0 mg |
| Sodium carboxymethyl cellulose (11%)/ Microcrystalline cellulose (89%) | 50.0 mg |
| Sucrose | 1.75 g |
| Sodium benzoate | 10.0 mg |
| Flavor and Color | q.v. |
| Purified water to | 5.0 ml |

The medicament, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Example 8

| Ingredient | Quantity (mg/capsule) |
| --- | --- |
| Active Ingredient | 15.0 mg |
| Starch | 407.0 mg |
| Magnesium stearate | 3.0 mg |
| Total | 425.0 mg |

The active ingredient, cellulose, starch, and magnesium stearate are blended, passed through a No. 20 mesh U.S. sieve, and filled into hard gelatin capsules in 560 mg quantities.

Formulation Example 9

An intravenous formulation may be prepared as follows:

| Ingredient | Quantity |
| --- | --- |
| Active Ingredient | 250.0 mg |
| Isotonic saline | 1000 ml |

Formulation Example 10

A topical formulation may be prepared as follows:

| Ingredient | Quantity |
| --- | --- |
| Active Ingredient | 1–10 g |
| Emulsifying Wax | 30 g |
| Liquid Paraffin | 20 g |
| White Soft Paraffin | to 100 g |

The white soft paraffin is heated until molten. The liquid paraffin and emulsifing wax are incorporated and stirred until dissolved. The active ingredient is added and stirring is continued until dispersed. The mixture is then cooled until solid.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See. e.g., U.S. Pat. No. 5,023,252, issued Jun. 11, 1991, herein incorporated by reference. Such patches may be constructed for continuous, pulsatile, or on demand delivery of pharmaceutical agents.

It may be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system used for the transport of biological factors to specific anatomical regions of the body is described in U.S. Pat. No. 5,011,472, which is herein incorporated by reference.

Indirect techniques, which are generally preferred, usually involve formulating the compositions to provide for drug latentiation by the conversion of hydrophilic drugs into lipid-soluble drugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

Utility

The compounds of this invention can be employed to bind VLA-4 ($\alpha_4\beta_1$ integrin) in biological samples and, accordingly, have utility in, for example, assaying such samples for VLA-4. In such assays, the compounds can be bound to a solid support and the VLA-4 sample added thereto. The amount of VLA-4 in the sample can be determined by conventional methods such as use of a sandwich ELISA assay. Alternatively, labeled VLA-4 can be used in a competitive assay to measure for the presence of VLA-4 in the sample. Other suitable assays are well known in the art.

In addition, certain of the compounds of this invention inhibit, in vivo, adhesion of leukocytes to endothelial cells mediated by VLA-4 and, accordingly, can be used in the treatment of diseases mediated by VLA-4. Such diseases include inflammatory diseases in mammalian patients such as asthma, Alzheimer's disease, atherosclerosis, AIDS dementia, diabetes (including acute juvenile onset diabetes), inflammatory bowel disease (including ulcerative colitis and Crohn's disease), multiple sclerosis, rheumatoid arthritis, tissue transplantation, tumor metastasis, meningitis, encephalitis, stroke, and other cerebral traumas, nephritis, retinitis, atopic dermatitis, psoriasis, myocardial ischemia and acute leukocyte-mediated lung injury such as that which occurs in adult respiratory distress syndrome.

The biological activity of the compounds identified above may be assayed in a variety of systems. For example, a compound can be immobilized on a solid surface and adhesion of cells expressing VLA-4 can be measured. Using such formats, large numbers of compounds can be screened. Cells suitable for this assay include any leukocytes known to express VLA-4 such as T cells, B cells, monocytes, eosinophils, and basophils. A number of leukocyte cell lines can also be used, examples include Jurkat and U937.

The test compounds can also be tested for the ability to competitively inhibit binding between VLA-4 and VCAM-1, or between VLA4 and a labeled compound known to bind VLA-4 such as a compound of this invention or antibodies to VLA-4. In these assays, the VCAM-1 can be immobilized on a solid surface. VCAM-1 may also be expressed as a recombinant fusion protein having an Ig tail (e.g., IgG) so that binding to VLA-4 may be detected in an immunoassay. Alternatively, VCAM-1 expressing cells, such as activated endothelial cells or VCAM-1 transfected fibroblasts, can be used. For assays to measure the ability to block adhesion to brain endothelial cells, the assays described in International Patent Application Publication No. WO 91105038 are particularly preferred. This application is incorporated herein by reference in its entirety.

Many assay formats employ labelled assay components. The labelling systems can be in a variety of forms. The label may be coupled directly or indirectly to the desired component of the assay according to methods well known in the art. A wide variety of labels may be used. The component may be labelled by any one of several methods. The most common method of detection is the use of autoradiography with $^3H$, $^{125}I$, $^{35}S$, $^{14}C$, or $^{32}P$ labelled compounds or the like. Non-radioactive labels include ligands which bind to labelled antibodies, fluorophores, chemiluminescent agents, enzymes and antibodies which can serve as specific binding pair members for a labelled ligand. The choice of label depends on sensitivity required, ease of conjugation with the compound, stability requirements, and available instrumentation.

Appropriate in vivo models for demonstrating efficacy in treating inflammatory responses include EAE (experimental autoimmune encephalomyelitis) in mice, rats, guinea pigs, or primates, as well as other inflammatory models dependent upon $\alpha_4$ integrins. Compounds having the desired biological activity may be modified as necessary to provide desired properties such as improved pharmacological properties (e.g., in vivo stability, bio-availability), or the ability to be detected in diagnostic applications. For instance, inclusion of one or more D-amino acids in the sulfonamides of this invention typically increases in vivo stability. Stability can be assayed in a variety of ways such as by measuring the half-life of the proteins during incubation with peptidases or human plasma or serum. A number of such protein stability assays have been described (see, e.g., Verhoef, et al., *Eur. J. Drug Metab. Pharnacokinet.*, 1990, 15(2:83–93).

For diagnostic purposes, a wide variety of labels may be linked to the compounds, which may provide, directly or indirectly, a detectable signal. Thus, the compounds of the subject invention may be modified in a variety of ways for a variety of end purposes while still retaining biological activity. In addition, various reactive sites may be introduced at the terminus for linking to particles, solid substrates, macromolecules, or the like.

Labeled compounds can be used in a variety of in vivo or in vitro applications. A wide variety of labels may be employed, such as radionuclides (e.g., gamma-emitting radioisotopes such as technetium-99 or indium-111), fluorescers (e.g., fluorescein), enzymes, enzyme substrates, enzyme cofactors, enzyme inhibitors, chemiluminescent compounds, bioluminescent compounds, and the like. Those of ordinary skill in the art will know of other suitable labels for binding to the complexes, or will be able to ascertain such using routine experimentation. The binding of these labels is achieved using standard techniques common to those of ordinary skill in the art.

In vitro uses include diagnostic applications such as monitoring inflammatory responses by detecting the presence of leukocytes expressing VLA-4. The compounds of this invention can also be used for isolating or labeling such cells. In addition, as mentioned above, the compounds of the invention can be used to assay for potential inhibitors of VLA-4/VCAM-1 interactions.

For in vivo diagnostic imaging to identify, e.g., sites of inflammation, radioisotopes are typically used in accordance with well known techniques. The radioisotopes may be bound to the peptide either directly or indirectly using intermediate functional groups. For instance, chelating agents such as diethylenetriaminepentacetic acid (DTPA) and ethylenediaminetetraacetic acid (EDTA) and similar molecules have been used to bind proteins to metallic ion radioisotopes.

The complexes can also be labeled with a paramagnetic isotope for purposes of in vivo diagnosis, as in magnetic resonance imaging (MRI) or electron spin resonance (ESR), both of which are well known. In general, any conventional method for visualizing diagnostic imaging can be used. Usually, gamma- and positron-emitting radioisotopes are used for camera imaging and paramagnetic isotopes are used for MRI. Thus, the compounds can be used to monitor the course of amelioration of an inflammatory response in an individual. By measuring the increase or decrease in lymphocytes expressing VLA-4, it is possible to determine whether a particular therapeutic regimen aimed at ameliorating the disease is effective.

The pharmaceutical compositions of the present invention can be used to block or inhibit cellular adhesion associated with a number of diseases and disorders. For instance, a number of inflammatory disorders are associated with integrins or leukocytes. Treatable disorders include, e.g., transplantation rejection (e.g., allograft rejection), Alzheimer's disease, atherosclerosis, AIDS dementia, diabetes (including acute juvenile onset diabetes), retinitis, cancer metastases, rheumatoid arthritis, acute leukocyte-mediated lung injury (e.g., adult respiratory distress syndrome), asthma, nephritis, and acute and chronic inflammation, including atopic dermatitis, psoriasis, myocardial ischemia, and inflammatory bowel disease (including Crohn's disease and ulcerative colitis). In preferred embodiments, the pharmaceutical compositions are used to treat inflammatory brain disorders, such as multiple sclerosis (MS), viral meningitis and encephalitis.

Inflammatory bowel disease is a collective term for two similar diseases referred to as Crohn's disease and ulcerative colitis. Crohn's disease is an idiopathic, chronic ulceroconstrictive inflammatory disease characterized by sharply delimited and typically transmural involvement of all layers of the bowel wall by a granulomatous inflammatory reaction. Any segment of the gastrointestinal tract, from the mouth to the anus, may be involved, although the disease most commonly affects the terminal ileum and/or colon. Ulcerative colitis is an inflammatory response limited largely to the colonic mucosa and submucosa. Lymphocytes and macrophages are numerous im lesions of inflammatory bowel disease and may contribute to inflammatory injury.

Asthma is a disease characterized by increased responsiveness of the tracheobronchial tree to various stimuli potentiating paroxysmal constriction of the bronchial airways. The stimuli cause release of various mediators of inflammation from IgE-coated mast cells, including histamine, eosinophilic and neutrophilic chemotactic factors, leukotrines, prostaglandin and platelet activating factor. Release of these factors recruits basophils, eosinophils and neutrophils, which cause inflammatory injury.

Atherosclerosis is a disease of arteries (e.g., coronary, carotid, aorta and iliac). The basic lesion, the atheroma, consists of a raised focal plaque within the intima, having a core of lipid and a covering fibrous cap. Atheromas compromise arterial blood flow and weaken affected arteries. Myocardial and cerebral infarcts are a major consequence of this disease. Macrophages and leukocytes are recruited to atheromas and contribute to inflammatory injury.

Rheumatoid arthritis is a chronic, relapsing inflammatory disease that primarily causes impairment and destruction of joints. Rheumatoid arthritis usually first affects the small joints of the hands and feet but then may involve the wrists, elbows, ankles and knees. The arthritis results from interaction of synovial cells with leukocytes that infiltrate from the circulation into the synovial lining of the joints. See e.g., Paul, *Immunology*, 3d ed., Raven Press (1993).

Another indication for the compounds of this invention is in treatment of organ or graft rejection mediated by VLA4. Over recent years there has been a considerable improvement in the efficiency of surgical techniques for transplanting tissues and organs such as skin, kidney, liver, heart, lung, pancreas and bone marrow. Perhaps the principal outstanding problem is the lack of satisfactory agents for inducing immunotolerance in the recipient to the transplanted allograft or organ. When allogeneic cells or organs are transplanted into a host (i.e., the donor and donee are different individuals from the same species), the host immune system is likely to mount an immune response to foreign antigens in the transplant (host-versus-graft disease) leading to destruction of the transplanted tissue. CD8+ cells, CD4 cells and monocytes are all involved in the rejection of transplant tissues. Compounds of this invention which bind to alpha-4 integrin are useful, inter alia, to block alloantigen-induced immune responses in the donee, thereby preventing such cells from participating in the destruction of the transplanted tissue or organ. See, e.g., Paul et al., *Transplant International* 9: 420–425 (1996); Georczynski et al., *Immunology* 87: 573–580 (1996); Georcyznski et al., *Transplant. Immunol.* 3: 55–61 (1995); Yang et al., *Transplantation* 60: 71–76 (1996); Anderson et al., *APMIS* 102: 23–27 (1994).

A related use for compounds of this invention which bind to VLA-4 is in modulating the immune response involved in "graft versus host" disease (GVHD). See e.g., Schlegel et al., *J. Immunol.* 155: 3856–3865 (1995). GVHD is a potentially fatal disease that occurs when immunologically competent cells are transferred to an allogeneic recipient. In this situation, the donor's immunocompetent cells may attack tissues in the recipient. Tissues of the skin, gut epithelia and liver are frequent targets and may be destroyed during the course of GVHD. The disease presents an especially severe problem when immune tissue is being transplanted, such as in bone marrow transplantation; but less severe GVHD has also been reported in other cases as well, including heart and liver transplants. The therapeutic agents of the present invention are used, inter alia, to block activation of the donor T-cells, thereby interfering with their ability to lyse target cells in the host.

A further use of the compounds of this invention is inhibiting tumor metastasis. Several tumor cells have been reported to express VLA-4 and compounds which bind VLA-4 block adhesion of such cells to endothelial cells. Steinback et al., *Urol. Res.* 23: 175–83 (1995); Orosz et al., *Int. J. Cancer* 60: 867–71 (1995); Freedman et al., *Leuk. Lymphoma* 13: 47–52 (1994); Okahara et al., *Cancer Res.* 54: 3233–6 (1994).

A further use of the compounds of this invention is in treating multiple sclerosis. Multiple sclerosis is a progressive neurological autoimmune disease that affects an estimated 250,000 to 350,000 people in the United States. Multiple sclerosis is thought to be the result of a specific autoimmune reaction in which certain leukocytes attack and initiate the destruction of myelin, the insulating sheath covering nerve fibers. In an animal model for multiple sclerosis, murine monoclonal antibodies directed against VLA-4 have been shown to block the adhesion of leukocytes to the endothelium, and thus prevent inflammation of the central nervous system and subsequent paralysis in the animals[16].

Pharmaceutical compositions of the invention are suitable for use in a variety of drug delivery systems, Suitable formulations for use in the present invention are found in *Remington's Pharmaceutical Sciences*, Mace Publishing Company, Philadelphia, Pa., 17th ed. (1985).

In order to enhance serum half-life, the compounds may be encapsulated, introduced into the lumen of liposomes, prepared as a colloid, or other conventional techniques may be employed which provide an extended serum half-life of the compounds. A variety of methods are available for preparing liposomes, as described in, e.g., Szoka, et al., U.S. Pat. Nos. 4,235,871, 4,501,728 and 4,837,028, each of which is incorporated herein by reference.

The amount administered to the patient will vary depending upon what is being administered, the purpose of the administration, such as prophylaxis or therapy, the state of the patient, the manner of administration, and the like. In therapeutic applications, compositions are administered to a patient already suffering from a disease in an amount sufficient to cure or at least partially arrest the symptoms of the disease and its complications. An amount adequate to accomplish this is defined as a "therapeutically effective dose." Amounts effective for this use will depend on the disease condition being treated as well as by the judgment of the attending clinician depending upon factors such as the severity of the inflammation, the age, weight and general condition of the patient, and the like.

The compositions administered to a patient are in the form of pharmaceutical compositions described above. These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds of the present invention will vary according to, for example, the particular use for which the treatment is made, the manner of administration of the compound, the health and condition of the patient, and the judgment of the prescribing physician. For example, for intravenous administration, the dose will typically be in the range of about 20 μg to about 500 μg per kilogram body weight, preferably about 100 μg to about 300 μg per kilogram body weight. Suitable dosage ranges for intranasal administration are generally about 0.1 pg to 1 mg per kilogram body weight. Effective doses can be extrapolated from dose-response curves derived from in vitro or animal model test systems.

The following synthetic and biological examples are offered to illustrate this invention and are not to be construed in any way as limiting the scope of this invention. Unless otherwise stated, all temperatures are in degrees Celsius.

EXAMPLES

In the examples below, the following abbreviations have the following meanings. If an abbreviation is not defined, it has its generally accepted meaning.

| | |
|---|---|
| aq or aq. | aqueous |
| AcOH | acetic acid |
| bd | broad doublet |
| bm | broad multiplet |
| bs | broad singlet |
| Bn | benzyl |
| Boc | N-tert-butoxylcarbonyl |
| BOC$_2$O | di-tert-butyl dicarbonate |
| BOP | benzotriazol-1-yloxy-tris(dimethylamino)phosphonium hexafluorophosphate |
| Cbz | carbobenzyloxy |
| CHCl$_3$ | chloroform |
| CH$_2$Cl$_2$ | dichloromethane |
| (COCl)$_2$ | oxalyl chloride |
| d | doublet |
| dd | doublet of doublets |
| dt | doublet of triplets |
| DBU | 1,8-diazabicyclo[5.4.0]undec-7-ene |
| DCC | 1,3-dicyclohexylcarbodiimide |

-continued

| | |
|---|---|
| DMAP | 4-N,N-dimethylaminopyridine |
| DME | ethylene glycol dimethyl ether |
| DMF | N,N-dimethylformamide |
| DMSO | dimethylsulfoxide |
| EDC | 1-(3-dimethylaminopropyl)-3-ethylcarbodiimide hydrochloride |
| Et$_3$N | triethylamine |
| Et$_2$O | diethyl ether |
| EtOAc | ethyl acetate |
| EtOH | ethanol |
| eq or eq. | equivalent |
| Fmoc | N-(9-fluorenylmethoxycarbonyl) |
| FmocONSu | N-(9-fluorenylmethoxycarbonyl)-succinimide |
| g | grams |
| h | hour |
| H$_2$O | water |
| HBr | hydrobromic acid |
| HCl | hydrochloric acid |
| HOBT | 1-hydroxybenzotriazole hydrate |
| hr | hour |
| K$_2$CO$_3$ | potassium carbonate |
| L | liter |
| m | multiplet |
| MeOH | methanol |
| mg | milligram |
| MgSO$_4$ | magnesium sulfate |
| mL | milliliter |
| mm | millimeter |
| mM | millimolar |
| mmol | millimol |
| mp | melting point |
| N | normal |
| NaCl | sodium chloride |
| Na$_2$CO$_3$ | sodium carbonate |
| NaHCO$_3$ | sodium bicarbonate |
| NaOEt | sodium ethoxide |
| NaOH | sodium hydroxide |
| NH$_4$Cl | ammonium chloride |
| NMM | N-methylmorpholine |
| Phe | L-phenylalanine |
| Pro | L-proline |
| psi | pounds per square inch |
| PtO$_2$ | platinum oxide |
| q | quartet |
| q.s. | quantity sufficient |
| quint. | quintet |
| rt | room temperature |
| s | singlet |
| sat | saturated |
| t | triplet |
| t-BuOH | tert-butanol |
| TFA | trifluoroacetic acid |
| THF | tetrahydrofuran |
| TLC or tlc | thin layer chromatography |
| Ts | tosyl |
| TsCl | tosyl chloride |
| TsOH | tosylate |
| μL | microliter |

In the examples below, all temperatures are in degrees Celcius (unless otherwise indicated). The following Methods were used to prepare the compounds set forth below as indicated.

Method 1

N-Tosylation Procedure

N-Tosylation of the appropriate amino acid was conducted via the method of Cupps, Boutin and Rapoport, *J. Org. Chem.*, 1985, 50: 3972.

Method 2

Methyl Ester Preparation Procedure

Amino acid methyl esters were prepared using the method of Brenner and Huber, *Helv. Chim. Acta*, 1953, 36: 1109.

Method 3

BOP Coupling Procedure

The desired dipeptide ester was prepared by the reaction of a suitable N-protected amino acid (1 equivalent) with the appropriate amino acid ester or amino acid ester hydrochloride (1 equivalent), benzotriazol-1-yloxy-tris(dimethylamino)phosphonium hexafluorophosphate [BOP] (2.0 equivalent), triethylamine (1.1 equivalent), and DMF. The reaction mixture was stirred at room temperature-overnight. The crude product is purified by flash chromatography to afford the dipeptide ester.

Method 4

Hydrogenation Procedure I

Hydrogenation was performed using 10% palladium on carbon (10% by weight) in methanol at 30 psi overnight. The mixture was filtered through a pad of Celite and the filtrate concentrated to yield the desired amino compound.

Method 5

Hydrolysis Procedure I

To a chilled (0° C.) THF/H$_2$O solution (2:1, 5–10 mL) of the appropriate ester was added LiOH (or NaOH) (0.95 equivalents). The temperature was maintained at 0° C. and the reaction was complete in 1–3 hours. The reaction mixture was extracted with ethyl acetate and the aqueous phase was lyophilized resulting in the desired carboxylate salt.

Method 6

Ester Hydrolysis Procedure II

To a chilled (0° C.) THF/H$_2$O solution (2:1, 5–10 mL) of the appropriate ester was added LiOH (1.1 equivalents). The temperature was maintained at 0° C. and the reaction was complete in 1–3 hours. The reaction mixture was concentrated and the residue was taken up into H$_2$O and the pH adjusted to 2–3 with aqueous HCl. The product was extracted with ethyl acetate and the combined organic phase was washed with brine, dried over MgSO$_4$, filtered and concentrated to yield the desired acid.

Method 7

Ester Hydrolysis Procedure III

The appropriate ester was dissolved in dioxane/H$_2$O (1:1) and 0.9 equivalents of 0.5 N NaOH was added. The reaction was stirred for 3–16 hours and then concentrated. The resulting residue was dissolved in H$_2$O and extracted with ethyl acetate. The aqueous phase was lyophilized to yield the desired carboxylate sodium salt.

Method 8

Sulfonylation Procedure I

To the appropriately protected aminophenylalanine analog (11.2 mmol), dissolved in methylene chloride (25 ml) and cooled to −78° C., was added the desired sulfonyl chloride (12 mmol) followed by dropwise addition of pyridine (2 mL). The solution was allowed to warm to room temperature and was stirred for 48 hr. The reaction solution was transferred to a 250 mL separatory funnel with methylene chloride (100 mL) and extracted with 1N HCl (50 mL×3), brine (50 mL), and water (100 mL). The organic phase was dried (MgSO$^4$) and the solvent concentrated to yield the desired product.

Method 9

Reductive Amination Procedure

Reductive amination of Tos-Pro-p-NH$^2$-Phe with the appropriate aldehyde was conducted using acetic acid, sodium triacetoxyborohydride and methylene chloride, and the combined mixture was stirred at room temperature overnight. The crude product was purified by flash chromatography.

Method 10

BOC Removal Procedure

Anhydrous hydrochloride (HCl) gas was bubbled through a methanolic solution of the appropriate Boc-amino acid ester at 0° C. for 15 minutes and the reaction mixture was stirred for three hours. The solution was concentrated to a syrup and dissolved in Et$_2$O and reconcentrated. This procedure was repeated and the resulting solid was placed under high vacuum overnight.

Method 11

Tert-Butyl Ester Hydrolysis Procedure I

The tert-butyl ester was dissolved in CH$_2$Cl$_2$ and treated with TFA. The reaction was complete in 1–3 hr, at which time the reaction mixture was concentrated and the residue dissolved in H$_2$O and lyophilized to yield the desired acid.

Method 12

EDC Coupling Procedure I

To a CH$_2$Cl$_2$ solution (5–20 mL) of N-(toluene-4-sulfonyl)-L-proline (1 equivalent), the appropriate amino acid ester hydrochloride (1 equivalent), N-methylmorpholine (1.1–2.2 equivalents) and 1-hydroxybenzotriazole (2 equivalents) were added and mixed, placed in an ice bath and 1-(3-dimethylaminopropyl)-3-ethyl carbodiimide (1.1 equivalents) added. The reaction was allowed to rise to room temperature and was stirred overnight. The reaction mixture was poured into H$_2$O and the organic phase was washed with sat. NaHCO$_3$ and brine, dried (MgSO$_4$ or Na$_2$SO$_4$), filtered and concentrated. The crude product was purified by column chromatography.

Method 13

EDC Coupling Procedure II

To a DMF solution (5–20 mL) of the appropriate N-protected amino acid (1 equivalent), the appropriate amino acid ester hydrochloride (1 equivalent), Et$_3$N (1.1 equivalents) and 1-hydroxybenzotriazole (2 equivalents) were added and mixed, placed in an ice bath and 1-(3-dimethylaminopropyl)-3-ethyl carbodiimide (1.1 equivalents) added. The reaction was allowed to rise to room temperature and was stirred overnight. The reaction mixture was partitioned between EtOAc and H$_2$O and the organic phase washed with 0.2 N citric acid, H$_2$O, sat. NaHCO$_3$ and brine, dried (MgSO$_4$ or Na$_2$SO$_4$), filtered and concentrated. The crude product was purified by column chromatography or preparative TLC.

Method 14

Sulfonylation Procedure II

The appropriate sulfonyl chloride was dissolved in $CH_2Cl_2$ and placed in an ice bath. L-Pro-L-Phe-OMe.HCl (1 equivalent) and $Et_3N$ (1.1 equivalent) was added and the reaction allowed to warm to room temperature and stirred overnight under an atmosphere of nitrogen. The reaction mixture was concentrated and the residue partitioned between EtOAc and $H_2O$, and the organic phase was washed with sat. $NaHCO_3$ and brine, dried ($MgSO_4$ or $Na_2SO_4$), filtered and concentrated. The crude product was purified by column chromatography or preparative TLC.

Method 15

Sulfonylation Procedure III

To a solution of L-Pro-L-4-(3-dimethylaminopropyloxy)-Phe-OMe (1 equivalent) [prepared using the procedure described in Method 10] in $CH_2Cl_2$ was added $Et_3N$ (5 equivalents) followed by the appropriate sulfonyl chloride (1.1 equivalent). The reaction was allowed to warm to room temperature and stirred overnight under an atmosphere of nitrogen. The mixture was concentrated, dissolved in EtOAc, washed with sat. $NaHCO_3$ and 0.2 N citric acid. The aqueous phase was made basic with solid $NaHCO_3$ and the product extracted with EtOAc. The organic phase was washed with brine, dried ($MgSO_4$ or $Na_2SO_4$), filtered and concentrated. The crude methyl ester was purified by preparative TLC. The corresponding acid was prepared using the procedure described in Method 7.

Method 16

Hydrogenation Procedure II

To a methanol (10–15 mL) solution of the azlactone was added NaOAc (1 equivalent) and 10% Pd/C. This mixture was placed on the hydrogenator at 40 psi $H_2$. After 8–16 hours, the reaction mixture was filtered through a pad of Celite and the filtrate concentrated to yield the dehydrodipeptide methyl ester. The ester was dissolved in dioxane/$H_2O$ (5–10 mL), to which was added 0.5 N NaOH (1.05 equivalents). After stirring for 1–3 hours, the reaction mix was concentrated and the residue was redissolved in $H_2O$ and washed with EtOAc. The aqueous phase was made acidic with 0.2 N HCl and the product was extracted with EtOAc. The combined organic phase was washed with brine (1×5 mL), dried ($MgSO_4$ or $Na_2SO_4$), filtered and concentrated to yield the acid as approximately a 1:1 mixture of diastereomers.

Method 17

Tert-Butyl Ester Hydrolysis Procedure II

The tert-butyl ester was dissolved in $CH_2Cl_2$ (5 mL) and treated with TFA (5 mL). The reaction was complete in 1–3 hours, at which time the reaction mixture was concentrated and the residue dissolved in $H_2O$ and concentrated. The residue was redissolved in $H_2O$ and lyophilized to yield the desired product.

Example 1

Synthesis of N-Methanesulfonyl)-L-prolyl-L-phenylalanine

Boc-L-Pro-OH and L-Phe-OBn.Hcl were treated with BOP and NMM in DMF to give, after aqueous workup and flash chromatography, Boc-L-Pro-L-Phe-OBn. This product was then treated with TFA and anisole, and the mixture was evaporated. The residue was dissolved in $Et_2O$ and washed with saturated aqueuos $NaHCO_3$ and saturated aqueous NaCl. The $Et_2O$ layer was dried over anhydrous $MgSO_4$, filtered, and the solvent evaporated to give L-Pro-L-Phe-OBn. The residue was treated with $CH_3SO_2Cl$ and $Et_3N$ in $CH_2Cl_2$ to give, after aqueous workup and flash chromatography, N-($CH_3SO_2$)-L-Pro-L-Phe-OBn. This product was then treated with 10% Pd on C in THF, and the mixture was shaken under 50 psi $H_2$. The mixture was filtered through Celite, and evaporated to give the title compound as a clear oil.

NMR data was as follows:

$^1$H NMR (DMSO-$d_6$, 300 MHz): δ=7.93 (d, J=8.2, 1H), 7.27–7.13 (m, 5H), 4.51–4.45 (m, 1H), 4.15 (dd, J=8.7, J=2.6, 1H), 3.59 (t, J=6.1, 1H), 3.30–3.25 (m, 2H), 3.10 (dd, J=13.7, J=4.9, 1H), 2.96 (dd, J =13.7, J=9.1, 1H), 2.87 (s, 3H), 2.03–1.93 (m, 1H), 1.77–1.54 (m, 3H).

$^{13}$C NMR (DMSO-$d_6$, 75 MHz): δ=172.6, 171.1, 137.4, 129.2, 128.1, 126.4, 61.2, 53.0, 48.6, 36.5, 35.2, 30.6, 24.0.

Mass Spectroscopy: (+FAB, 3-nitrobenzyl alcohol) 341 (MH+).

Example 2

Synthesis of N-(α-Toluenesulfonyl)-L-prolyl-L-phenylalanine

Substitution of $PhCH_2SO_2Cl$ for $CH_3SO_2Cl$, and following the methods for preparation of Example 1 (9), gave the title compound as a clear oil.

NMR data was as follows:

$^1$H NMR (DMSO-$d_6$, 300 MHz): δ=8.01 (d, J=8.2, 1H), 7.39–7.20 (m, 5H), 7.18–7.13 (m, 5H), 4.53–4.46 (m, 1H), 4.42 (d, J=13.5, 1H), 4.35 (d, J=13.5, 1H), 4.20–4.17 (m, 1H), 3.31–3.18 (m, 3H), 3.09 (dd, J =13.9, J=4.8, 1H), 2.96 (dd, J=13.8, J=8.9, 1H), 2.03–1.95 (m, 1H), 1.79–1.58 (m, 3H).

$^{13}$C NMR (DMSO-$d_6$, 75 MHz): δ=172.6, 171.5, 137.6, 131.0, 129.3, 129.0, 128.9, 128.1, 128.0, 126.3, 61.5, 53.3, 48.8, 36.5, 30.8, 30.6, 24.0.

Mass Spectroscopy: (+FAB, 3-nitrobenzyl alcohol) 417 (MH+).

Example 3

Synthesis of N-(Toluene-4-sulfonyl)-L-prolyl-L-phenylalanine

Substitution of 4-$CH_3(C_6H_4)SO_2Cl$ for $CH_3SO_2Cl$, and following the methods for preparation of Example 1 (9), gave the title compound as a clear oil.

NMR data was as follows:

$^1$H NMR (DMSO-$d_6$, 300 MHz): δ=8.07 (d, J=8.0, 1H), 7.68 (d, J=8.2, 2H), 7.39 (d, J=8.1, 2H), 7.29–7.15 (m, 5H), 4.52–4.44 (m, 1H), 4.10–4.07 (m, 1H), 3.34–3.27 (m, 1H), 3.12–3.06 (m, 2H), 2.98 (dd, J =13.7, J=8.7, 1H), 2.39 (s, 3H), 1.57–1.36 (m, 4H).

$^{13}$C NMR (DMSO-$d_6$, 75 MHz): δ=172.6, 170.8, 143.6, 137.4, 133.8, 129.8, 129.3, 128.1, 127.5, 126.4, 61.3, 53.2, 49.0, 36.6, 30.4, 23.7, 21.0.

Mass Spectroscopy: (+FAB, glycerol/trifluoroacetic acid) 417 (MH+).

Example 4

Synthesis of N-(Toluene4-sulfonyl)-L-prolyl-L-(N-methyl)phenylalanine

N-Methyl-L-Phe-OH was treated with benzyl alcohol and 4-methylphenylsulfonic acid to give N-Methyl-L-Phe-OBn TsOH. Substitution of L-Pro-OH for D-Pro-OH, and substitution of N-Methyl-Phe-OBn.TsOH for L-Phe-OBn.TsOH, and following the methods for preparation of Example 6 (17), gave the title compound as a clear oil.

NMR data was as follows:

$^1$H NMR (DMSO-$d_6$, 300 MHz): δ=7.60 (d, J=8.2, 2H), 7.34 (d, J=8.2, 2H), 7.27–7.16 (m, 5H), 4.97–4.92 (m, 1H), 4.64–4.61 (m, 1H), 3.33 (bs, 1H), 3.25–3.12 (m, 3H), 3.04 (dd, J=10.5, J=14.6, 1H), 2.85 (s, 3H), 2.37 (s, 3H), 1.86–1.72 (m, 2H), 1.68–1.50 (m, 2H).

$^{13}$C NMR (DMSO-$d_6$, 75 MHz): δ=171.9, 171.1, 143.0, 137.9, 135.6, 129.6, 128.7, 128.2, 127.2, 126.3, 58.6, 48.0, 33.4, 33.0, 30.4, 29.6, 23.9, 21.0.

Mass Spectroscopy: (+FAB, 3-nitrobenzyl alcohol) 431 (MH+).

Example 5

Synthesis of N-(Toluene-4-sulfonyl)-L-pipecolinyl-L-phenylalanine

Substitution of L-pipecolinic acid for D-Pro-OH, and following the methods for preparation of Example 6 (17), gave the title compound as a clear oil.

NMR data was as follows:

$^1$H NMR (DMSO-$d_6$, 300 MHz): δ=8.09 (d, J=8.0, 1H), 7.44 (d, J=8.2, 2H), 7.34–7.21 (m, 5H), 7.17 (d, J=8.2, 2H), 4.44 (d, J=4.8, 1H), 4.32–4.24 (m, 1H), 3.61–3.53 (m, 2H), 3.33 (bs, 1H), 3.17–3.11 (m, 1H), 3.07 (dd, J=13.8, J=4.5, 1H), 2.89 (dd, J=13.8, J=9.9, 1H), 2.33 (s, 3H), 1.88 (bd, J=12.9, 1H), 1.40–1.30 (m, 3H), 1.08–1.05 (m, 2H).

$^{13}$C NMR (DMSO-$d_6$, 75 MHz): δ=172.8, 169.8, 142.7, 137.7, 136.6, 129.4, 129.2, 128.2, 126.8, 126.5, 54.1, 53.4, 42.4, 36.3, 30.4, 26.7, 23.5, 21.0.

Mass Spectroscopy: (+FAB, 3-nitrobenzyl alcohol) 431 (MH+).

Example 6

Synthesis of N-(Toluene-4-sulfonyl)-D-prolyl-L-phenylalanine

D-Pro-OH was treated with TsCl and NaOH in $H_2O$ to give, after acidification, extraction, drying over anhydrous $MgSO_4$, and evaporation, N-(Toluene- 4-sulfonyl)-D-Pro-OH. This product was treated with H-Phe-OBn.Hcl, BOP, and NMM in DMF to give, after aqueous workup and flash chromatography, N-(toluene-4-sulfonyl)-D-Pro-Phe-OBn. This product was treated with 10% Pd on C in THF, and the mixture was shaken under 50 psi $H_2$. The mixture was filtered through celite and evaporated to give the title compound as a clear oil.

NMR data was as follows:

$^1$H NMR (DMSO-$d_6$, 300 MHz): δ=8.10 (d, J=8.4, 1H), 7.70 (d, J=8.2, 2H), 7.40 (d, J=8.2, 2H), 7.28–7.15 (m, 5H), 4.51–4.44 (m, 1H), 4.13 (t, J=5.7, 1H), 3.33–3.25 (m, 2H), 3.11–3.03 (m, 2H), 2.94 (dd, J=13.8, J=9.0, 1H), 2.39 (s, 3H), 1.66–1.57 (m, 1H), 1.50–1.37 (m, 3H).

$^{13}$C NMR (DMSO-$d_6$, 75 MHz): δ=172.6, 170.8, 143.5, 137.3, 134.1, 129.8, 129.3, 128.1, 127.4, 126.4, 61.3, 53.0, 48.9, 36.8, 30.4, 23.8, 21.0.

Mass Spectroscopy: (+FAB, 3-nitrobenzyl alcohol) 417 (MH+).

Example 7

Synthesis of N-(Toluene-4-sulfonyl)-L-(trans-4-hydroxy)-prolyl-L-phenylalanine

Substitution of trans-4-hydroxy-L-proline for D-Pro-OH, and following the methods for preparation of Example 6 (17), gave the title compound as a clear oil.

NMR data was as follows:

$^1$H NMR (DMSO-$d_6$, 300 MHz): δ=8.25 (d, J=8.1, 1H), 7.64 (d, J=8.2, 2H), 7.36 (d, J=8.2, 2H), 7.30–7.15 (m, 5H), 4.81 (bs, 1H), 4.47–4.40 (m, 1H), 4.15–4.10 (m, 2H), 3.44 (dd, J=10.3, J=4.8, 1H), 3.35 (bs, 1H), 3.09–2.91 (m, 3H), 2.38 (s, 3H), 1.72–1.64 (m, 2H).

$^{13}$C NMR (DMSO-$d_6$, 75 MHz): δ=172.6, 171.0, 143.1, 137.4, 134.1, 129.5, 129.3, 128.1, 127.7, 126.4, 68.1, 60.3, 56.1, 53.4, 36.7, 30.4, 21.0.

Mass Spectroscopy: (+FAB, 3-nitrobenzyl alcohol) 433 (MH+).

Example 8

Synthesis of N-(Toluene-4-sulfonyl)-L-(azetidine-2-carbonyl)-L-phenylalanine

Substitution of (S)-2-azetidinecarboxylic acid for D-Pro-OH, and following the methods for preparation of Example 6 (17), gave the title compound as a clear oil.

NMR data was as follows:

$^1$H NMR (DMSO-$d_6$, 300 MHz): δ=8.12 (d, J=8.0, 1H), 7.69 (d, J=8.2, 2H), 7.47 (d, J=8.2, 2H), 7.31–7.13 (m, 5H), 4.54–4.47 (m, 1H), 4.23 (t, J=8.3, 1H), 3.67–3.58 (m, 2H), 3.47 (q, J=8.4, 1H), 3.33 (bs, 1H), 3.10 (dd, J=13.7, J=5.2, 1H), 2.98 (dd, J=13.6, J=7.9, 1H), 2.42 (s, 3H), 2.03–1.87 (m, 2H).

$^{13}$C NMR (DMSO-$d_6$, 75 MHz): δ=172.3, 168.7, 144.3, 137.1, 130.9, 130.0, 129.4, 128.3, 128.2, 126.6, 61.8, 53.1, 47.9, 36.7, 21.1, 19.6.

Mass Spectroscopy: (+FAB, 3-nitrobenzyl alcohol) 403 (NH+).

Example 9

Synthesis of N-(Toluene-4-sulfonyl)-L-prolyl-D,L-homophenylalanine

N-(toluene-4-sulfonyl)-L-proline (250 mg, 0.92 mmol) was dissolved in DMF (20 mL) with D,L-homophenylalanine methyl ester (166 mg, 1.1 eq), $Et_3N$ (2.1 eq, 283 μL), and BOP (1.1 eq, 410 mg). The dipeptide was isolated in 73% yield (300 mg, 0.67 mmol) as an oil. The ester (300 mg, 0.67 mmol) was then hydrolyzed in a 1:1 MeOH:$H_2O$ (5 mL) solution with NaOH (1.1 eq, 28 mg). The acid was isolated as a foam in 60% yield (175 mg, 0.40 mmol).

NMR data was as follows:

$^1$H NMR (300 MHz, $CD_3OD$): δ=7.60 (m, 2H), 7.20 (m, 2H), 7.03 (m, 5H), 4.23–3.87 (m, 2H), 3.42 (m, 1H), 3.29 (m, 1H), 2.58 (m, 2H), 2.20 (s, 3H), 2.02–1.38 (m, 7H).

$^{13}$C NMR (75 MHz, $CD_3OD$); δ=175.53, 175.17, 146.49, 146.19, 142.93, 135.91, 135.04, 131.72, 130.28, 129.61, 129.49, 129.21, 127.70, 64.39, 63.59, 53.76, 53.52, 51.55, 51.17, 35.15, 33.42, 32.74, 32.60, 32.48, 26.28, 26.20, 22.14.

Mass Spectroscopy: (FAB) 431 (M+H).

Example 10

Synthesis of N-(4-Chlorobenzenesulfonyl)-L-prolyl-L-phenylalanine

Substitution of 4-chlorophenyl-$SO_2Cl$ for $CH_3SO_2Cl$, and following the methods for the preparation of Example 1 (9), gave the title compound as a solid, mp=69–71° C.

NMR data was as follows:

¹H NMR (300 MHz, CDCl₃): δ=7.77 (m, 2H), 7.53 (m, 2H), 7.31 (m, 5H), 4.72 (m, 1H), 4.04 (m, 1H), 3.35 (m, 2H), 3.10 (m, 2H), 2.05 (m, 1H), 1.54 (m, 3H).

¹³C NMR (75 MHz, CD₃OD): δ=174.67, 174.41, 141.23, 138.81, 137.55, 135.02, 131.18, 130.04, 129.45, 128.45, 63.75, 55.48, 38.79, 32.32, 25.87 (1C buried under solvent peak).

Mass Spectroscopy: (FAB) 437 (M+H).

Example 11

Synthesis of N-(1-Naphthalenesulfonyl)-L-prolyl-L-phenylalanine

Substitution of 1-naphthyl-SO₂Cl for CH₃SO₂Cl, and following the methods for preparation of Example 1 (9), gave the title compound as a clear oil.

NMR data was as follows:

¹H NMR (DMSO-d₆, 300 MHz): δ=8.73–8.70 (m, 1H), 8.24 (d, J=8.2, 1H), 8.12–8.06 (m, 2H), 7.69–7.57 (m, 2H), 7.33–7.13 (m, 7H), 4.40–4.33 (m, 2H), 3.34–3.23 (m, 3H), 3.03 (dd, J=14.0, J=5.2, 1H), 2.88 (dd, J=13.7, J=8.8, 1H), 1.79–1.15 (m, 4H).

¹³C NMR (DMSO-d₆, 75 MHz): δ=172.6, 170.9, 137.4, 134.3, 134.0, 133.6, 119.2, 129.1, 129.0, 128.23, 128.18, 128.1, 126.9, 126.4, 124.7, 124.6, 60.6, 53.4, 48.7, 36.5, 30.8, 24.0.

Mass Spectroscopy: (+FAB, 3-nitrobenzyl alcohol) 475 (Mna+).

Example 12

Synthesis of N-(2-Naphthalenesulfonyl)-L-prolyl-L-phenylalanine

Substitution of 2-naphthyl-SO₂Cl for CH₃SO₂Cl, and following the methods for preparation of Example 1 (9), gave the title compound as a clear oil.

NMR data was as follows:

¹H NMR (DMSO-d₆, 300 MHz): δ=8.18–8.03 (m, 4H), 7.82 (dd, J=8.7, J=1.8, 1H), 7.74–7.64 (m, 2H), 7.32–7.15 (m, 6H), 4.53–4.46 (m, 1H), 4.25–4.21 (m, 1H), 3.34–3.27 (m, 3H), 3.10 (dd, J=13.8, J=5.1, 1H), 2.99 (dd, J=13.7, J=8.8, 1H), 1.56–1.36 (m, 4H).

¹³C NMR (DMSO-d₆, 75 MHz): δ=172.6, 170.8, 137.4, 134.4, 133.9, 131.8, 129.4, 129.3, 129.0, 128.7, 128.1, 127.8, 127.6, 127.4, 122.8, 61.4, 53.2, 49.1, 36.6, 30.4, 23.8.

Mass Spectroscopy: (+FAB, 3-nitrobenzyl alcohol) 475 (Mna+).

Example 13

Synthesis of N-(4-Methoxybenzenesulfonyl)-L-prolyl-L-phenylalanine

Substitution of 4-methoxyphenyl-SO₂Cl for CH₃SO₂Cl, and following the methods for the preparation of Example 1 (9), gave the title compound as a solid.

NMR data was as follows:

¹H NMR (300 MHz, CDCl₃): δ=7.77 (m, 2H), 7.31 (m, 5H), 7.01 (m, 2H), 4.80 (m, 1H), 4.05 (m, 1H), 3.86 (s, 3H), 3.35 (m, 2H), 3.10 (m, 2H), 1.96 (m, 1H), 1.54 (m, 3H).

¹³C NMR (75 MHz, CD₃OD): δ=174.69, 174.54, 165.63, 136.75, 131.69, 131.07, 130.02, 128.45, 116.13, 63.84, 56.83, 55.35, 51.09, 38.81, 32.15, 26.63.

Mass Spectroscopy: (FAB) 433 (M+H).

Example 14

Synthesis of N-(4-tert-Butylbenzenesulfonyl)-L-prolyl-L-phenylalanine

Substitution of 4-tert-butylphenyl-SO₂Cl for CH₃SO₂Cl, and following the methods for preparation of Example 1 (9), gave the title compound as a solid.

NMR data was as follows:

¹H NMR (300 MHz, CDCl₃): δ=7.75 (d, 2H, J=8.52 Hz), 7.55 (d, 2H, J=8.43 Hz), 7.29 (m, 5H), 4.80 (m, 1H), 4.05 (m, 1H), 3.30 (m, 3H), 3.10 (m, 3H), 1.95 (m, 1H), 1.56 (m, 2H), 1.34 (s, 9H).

¹³C NMR (75 MHz, CD₃OD): δ=174.81, 174.47, 159.01, 138.79, 135.59, 131.09, 130.02, 129.45, 128.43, 128.05, 63.83, 55.46, 51.09, 38.84, 36.66, 32.20, 31.99, 25.83.

Mass Spectroscopy: (FAB) 459 (M+H).

Example 15

Synthesis of N-(Toluene-4-sulfonyl)-L-(trans-4-fluoro)-prolyl-L-phenylalanine

The product from Example 49 (176) was treated with 10% Pd on C in THF and the mixture was shaken under 50 psi H₂. The mixture was filtered through celite and evaporated to give the title compound as a clear oil.

NMR data was as follows:

¹H NMR (DMSO-d₆, 300 MHz): δ=8.43 (d, J=8.1, 1H), 7.66 (d, J=8.3, 2H), 7.35 (d, J=8.3, 2H), 7.29–7.13 (m, 5H), 5.10 (bd, J=53.3, 1H), 4.49–4.42 (mg 1H), 4,19 (t, J=8.3, 1H), 3.63–3.46 (m, 2H), 3.34 (bs, 1H), 3.06 (dd, J=13.7, J=5.4, 1H), 2.95 (dd, J=13.7, J=8.3, 1H), 2.38 (s, 3H), 2.25–2.12 (m, 1H), 1.94–1.72 (m, 1H).

¹³C NMR (DMSO-d₆, 75 MHz): δ=172.5, 170.4, 143.4, 137.4, 134.2, 129.5, 129.4, 128.1, 127.6, 126.5, 92.0 (d, J=177 Hz), 59.9, 55.1, 53.4, 37.6 (d, J=21 Hz), 36.8, 21.0.

Mass Spectroscopy; (+FAB, 3-nitrobenzyl alcohol) 435 (MH+).

Example 16

Synthesis of N-(Toluene-4-sulfonyl)-L-(cis-4-fluoro)-prolyl-L-phenylalanine

The product from Example 50 (177) was treated with 10% Pd on C in THF and was shaken under 50 psi H₂. The mixture was filtered through celite and evaporated to give the title compound as a clear oil.

NMR data was as follows:

¹H NMR (DMSO-d₆, 300 MHz): δ=7.78 (d, J=7.7, 1H), 7.73 (d, J =8.2, 2H), 7.41 (d, J=8.2, 2H), 7.29–7.13 (m, 5H), 5.10 (dt, Jd=52.9, Jt=3.5, 1H), 4.53–4.46 (m, 1H), 4.31–4.27 (m, 1H), 3.60–3.28 (m, 3H), 3.06–2.94 (m, 2H), 2.39 (s, 3H), 2.18 (dd, J=19.8, J=15.2, 1H), 1.93–1.70 (m, 1H).

¹³C NMR (DMSO-d₆, 75 MHz): δ=172.1, 169.7, 144.1, 136.8, 132.8, 130.0, 129.3, 128.1, 127.7, 126.6, 92.0 (d, J=176 Hz), 60.5, 55.1 (d, J=23.5), 53.2, 36.9, 36.2, 21.0.

Mass Spectroscopy: (+FAB, 3-nitrobenzyl alcohol) 435 (MH+).

Example 17

Synthesis of N-(Toluene-4-sulfonyl)-L-(5,5-dimethyl)-thiaprolyl-L-phenylalanine

N-(Toluene-4-sulfonyl)-L-(5,5-dimethyl)-thiazolidine-4-carboxylic acid was prepared from L-(5,5-dimethyl)- thiazolidine-4-carboxylic acid using the procedure described in Method 1. The title compound was prepared according to the procedure described for Example 1 (9) to provide for a solid having a mp=79–81° C.

NMR data was as follows:

$^1$H NMR (CDCl$_3$, 300 MHz): δ=0.98 (s, 3H), 1.08 (s, 3H), 2.42 (s, 3H), 3.04–3.34 (m, 2H), 3.88 (s, 1H), 4.38 (d, 1H, J=10.3 Hz), 4.52 (d, 1H, J=10.2 Hz), 4.90 (m, 1H), 7.09 (bd, 1H), 7.15–7.37 (m, 7H), 7.73 (d, 2H, J=8.2 Hz).

$^{13}$C NMR (CDCl$_3$, 75 MHz): δ=22.3, 24.3, 29.6, 38.3, 51.2, 54.1, 55.3, 73.9, 127.7, 128.7, 129.2, 130.1, 130.7, 133.0, 136.5, 145.6, 169.9, 174.5.

Mass Spectroscopy: (FAB+) 463 (M+H).

Example 18

Synthesis of N-(2-Methoxycarbonylbenzenesulfonyl)-L-prolyl-L-phenylalanine

The title compound was prepared from the product of Example 53 using the procedure described in Method 4, yielding a yellow solid, mp=163–165° C.

NMR data was as follows:

$^1$H NMR (CDCl$_3$, 300 MHz): δ=8.74 (bs, 1H); 7.93 (d, 1H, J=7.57 Hz); 7.70 (d, 1H, J=8.12 Hz); 7.57 & 7.25 (M, 8H); 4.69 (m, 1H); 4.39 (d, 1H, J=7.69 Hz); 3.93 (s, 3H); 3.44 (m, 1H); 3.29 (m, 2H); 2.93 (m, 1H); 1.88, 1.62 & 1.17 (m, 4H).

$^{13}$C NMR (CDCl$_3$, 300 MHz): δ=175.67, 172.45, 169.27, 137.19, 135.39, 134.12, 133.67, 131.42, 130.55, 129.77, 129.52, 129.09, 127.52, 62.19, 54.08, 49.34, 37.58, 31.48, 30.89, 24.21.

Mass Spectroscopy, (+FAB) 461 (M+H) 493 (M+Na).

Example 19

Synthesis of N-(2-Carboxybenzenesulfonyl)-L-prolyl-L-phenylalanine

The product of Example 18 (56) (1.8 mmoles) was mixed with dioxane (25 mL) and 1N NaOH (1.8 mmoles) and the reaction was stirred at room temperature for 16 hours. 1N HCl (1.8 mmoles) was added and the water and dioxane were removed under reduced pressure. The product was extracted with 0.2 N NaOH (50 mL) and EtOAc (2×50 mL) and the recovered organic layer was dried over MgSO$_4$, filtered, and concentrated to yield a colorless oil.

NMR data was as follows:

$^1$H NMR (CDCl$_3$, 300 MHz): δ=11.15 (bs, 2H); 7.95, 7.57, & 7.21 (m, 9H); 4.74 (m, 1H); 4.53 (m, 1H); 3.44 (m, 1H); 3.28 (m, 2H); 2.91 (m, 1H); 1.89 (M, 2H); 1.60 (m, 1H); 1.06 (m, 1H).

$^{13}$C NMR (CDCl$_3$, 300 MHz): δ=175.75, 173.60, 171.31, 136.81, 135.18, 133.72, 131.58, 130.81, 129.70, 129.18, 127.66, 67.52, 61.99, 53.95, 49.36, 45.09, 37.40, 24.19, 21.66.

Mass Spectroscopy: (+FAB) 447 (M+H).

Example 20

Synthesis of N-(Toluene-4-sulfonyl)-L-thiaprolyl-L-phenylalanine

N-(Toluene-4-sulfonyl)-L-thiazolidine-4-carboxylic acid was prepared from L-thiazolidine-4-carboxylic acid using the procedure described in Method 1. The title compound was prepared according to the procedure described for Example 1 (9) as a solid, mp=60–65° C.

NMR data was as follows:

$^1$H NMR (CDCl$_3$, 300 MHz): δ=2.43 (S, 5H), 3.0–3.40 (m, 3H), 4.0 (d, 1H, J=15.7 Hz), 4.55 (d, 1H, J=15.8 Hz), 4.64 (m, 1H), 4.87 (m, 1H), 7.19–7.41 (m, 7H), 7.72 (m, 2H).

$^{13}$C NMR (CDCl$_3$, 75 MHz): δ=22.3, 33.6, 37.7, 52.0, 53.0, 65.8, 127.8, 128.5, 129.4, 129.9, 130.7, 133.9, 136.2, 145.7, 169.4, 175.0.

Mass Spectroscopy: (FAB+) 435 (M+H).

Example 21

Synthesis of N-(3,5-Dichlorobenzenesulfonyl)-L-prolyl-L-phenylalanine

Proline methyl ester hydrochloride (2.68 g, 16.2 mmol) was dissolved in pyridine (20 mL) and 3,5-dichlorophenylsulfonyl chloride (3.57 g, 14.6 mmol) was added to the mixture and stirred for 19 hr. Water (5 mL) was added and the mixture was stirred for 45 minutes before diluting with water (200 mL). The mixture was extracted with Et$_2$O (2×150 mL) and the combined extracts were washed with water (3×100 mL), 1N HCl (150 mL) and saturated aqueous NaHCO$_3$ (150 mL), then dried (MgSO$_4$), filtered and evaporated in vacuo to give 3,5-dichlorophenylsulfonylproline methyl ester as an oil (4.34 g, 88%). The methyl ester was dissolved in MeOH (20 mL) and 1N NaOH (20 mL) was added. The mixture was gently warmed until homogeneous and then stirred for 1.5 hr. The solvent was removed in vacuo and the residue taken up in water (50 mL). The aqueous solution was washed with Et$_2$O (30 mL) and then made acidic with 12 N HCl. The mixture was extracted with CHCl$_3$ (2×40 mL) and the combined extracts were dried over anhydrous MgSO$_4$, filtered and the solvent evaporated in vacuo to give 3,5-dichlorophenylsulfonyl-L-proline as a solid (3.37 g, 83%). 3,5-Dichlorophenylsulfonyl-L-proline was coupled to L-phenylalanine ethyl ester using the procedure described in Method 3 above to give the corresponding dipeptide ethyl ester (348 mg, 45%). The title compound was prepared via hydrolysis of the ethyl ester using NaOH in MeOH (61 mg, 19%). NMR analysis indicated that diastereomers were present.

NMR data was as follows:

$^1$H NMR (CDCl$_3$): δ=8.11 (bs, 1H), 7.72 (d, 2H, J=1.9 Hz), 7.61 (q, 1H, J=2.0 Hz), 7.39–7.20 (6H), 4.92 (m, 1H), 4.15 (m, 1H), 3.52–3.09 (4H), 2.11 (m, 1H), 1.95–1.49 (3H).

$^{13}$C NMR (CDCl$_3$): δ=175.4, 175.2, 171.8, 171.7, 139.5, 139.3, 137.0, 136.6, 135.8, 134.0, 134.0, 129.9, 129.5, 127.7, 126.7, 111.4, 63.1, 62.9, 53.8, 53.6, 50.5, 50.3, 45.1, 37.9, 31.3, 30.8, 24.8, 24.6.

Mass Spectroscopy: FAB m/e 471 (M+H).

Example 22

Synthesis of N-(4-Trifluoromethoxybenzenesulfonyl)-L-prolyl-L-phenylalanine

The title compound was prepared as described in Example 21 (59) except 4-trifluoromethoxyphenylsulfonyl chloride was used in place of 3,5-dichlorophenylsulfonyl chloride.

NMR data was as follows:

$^1$H NMR (CDCl$_3$): δ=7.90 (d, 2H, J=8.8 Hz), 7.38–7.21 (8H), 6.90 (bs, 1H), 4.90 (m, 1H), 4.15 (dd, 1H, J=2.5, 8.4 Hz), 3.38 (m, 2H), 3.12 (m, 2H), 1.98 (m, 1H), 1.55 (2H), 1.41 (m, 1H).

<sup>13</sup>C NMR (CDCl<sub>3</sub>): δ=174.9, 172.0, 153.3, 136.6, 134.9, 130.6, 129.9, 129.2, 127.7, 121.7, 62.8, 53.8, 50.2, 37.9, 30.6, 24.6.

Mass Spectroscopy: FAB m/e 487 (M+H).

Example 23

Synthesis of N-(3,4-Dichlorobenzenesulfonyl)-L-prolyl-L-phenylalanine

The title compound was prepared as in Example 21 (59) except 3,4-dichlorophenylsulfonyl chloride was used in place of 3,5-dichlorophenylsulfonyl chloride.

NMR data was as follows:

$^1$H NMR (CDCl$_3$): δ=7.94 (d, 1H, J=1.9 Hz), 7.64 (m, 2H), 7.55 (bs, 1H), 7.36–7.21 (6H), 4.92 (dt, 1H, J=5.2, 8.0 Hz), 4.16 (m, 1H), 3.36 (m, 2H), 3.11 (m, 1H), 1.98 (m, 1H), 1.58 (m, 2H), 1.40 (m, 1H).

$^{13}$C NMR (CDCl$_3$): δ=175.0, 171.8, 139.5, 136.4, 134.7, 132.1, 130.2, 129.9, 129.2, 127.7, 127.4, 62.9, 53.8, 50.3, 37.9, 30.7, 24.6.

Mass Spectroscopy: FAB m/e 471 (M+H).

Example 24

Synthesis of N-(Toluene-4-sulfonyl)-D,L-(trans-3-phenyl)prolyl-L-phenylalanine

N-(Toluene4-sulfonyl)-trans-3-phenylproline (prepared via the method of Chung et al., *J. Org. Chem.*, 55: 270–275 (1990)) was coupled to L-phenylalanine ethyl ester using the procedure described in Method 3 and purified by silica gel flash chromatography (93/7 CH$_2$Cl$_2$/MeOH) to give the ethyl ester of the title compound as a white solid. The acid was prepared via hydrolysis of the ethyl ester using NaOH in ethanol.

NMR data was as follows:

$^1$H NMR (DMSO-d$_6$ d 8.38 (m,1H), 7.70 (m, 2H), 7.40–7.06 (10H), 6.80 (m, 1H), 6.62 (m, 1H), 4.50 (m, 1H), 4.13 (d, 0.5H, J=5.2 Hz), 3.97 (d, 0.5H, J=5.5 Hz), 3.46 (m, 2H), 3.02 (m, 3H), 2.43 (s, ½×3H), 2.42 (s, ½×3H), 2.07 (m, 1H), 1.45 (m, 1H).

$^{13}$C NMR (DMSO-d$_6$): δ=172.9, 172.8, 170.7, 170.7, 144.1, 143.9, 141.4, 141.3, 138.0, 137.7, 134.9, 134.6, 130.2, 130.1, 129.8, 129.6, 128.7, 128.6, 128.5, 127.8, 127.7, 127.2, 127.1, 126.9, 126.8, 126.7, 79.6, 67.9, 53.6, 53.5, 49.7, 49.5, 49.5, 49.1, 37.2, 37.1, 32.5, 32.3, 21.4.

Mass Spectroscopy: FAB m/e 493 (M+H).

Example 25

Synthesis of N-(3,4-Dimethoxybenzenesulfonyl)-L-prolyl-L-phenylalanine

The title compound was prepared as in Example 21 (59) except that 3,4-dimethoxyphenylsulfonyl chloride was used in place of the 3,5-dichlorophenylsulfonyl chloride. NMR analysis indicated that epimerization had occurred to give a ca. 65:35 mixture of diastereomers.

NMR data was as follows:

$^1$H NMR (CDCl$_3$): δ=7.46 (m, 1H), 7.39–7.20 (6H), 6.97 (dd, 1H, J =4.5, 8.4 Hz), 4.85 (m, 1H), 4.10 (m, 1H), 3.96 (s, 0.35×3H), 3.95 (s, 0.65×3H), 3.93 (s, 0.35×3H), 3.92 (s, 0.65×3H), 3.44–3.22 (2H), 3.11 (m, 2H), 2.01 (m, 1H), 1.60–1.33 (3H).

$^{13}$C NMR (CDCl$_3$): δ=175.1, 174.7, 172.5, 172.3, 153.7, 149.8, 136.6, 135.9, 130.2, 129.9, 129.4, 129.1, 128.0, 128.0, 127.9, 127.7, 122.4, 111.4, 110.7, 63.2, 62.8, 57.0, 56.8, 53.8, 53.6, 50.3, 50.2, 38.0, 31.1, 30.5, 24.8, 24.7.

Mass Spectroscopy: FAB m/e 463 (M+H).

Example 26

Synthesis of N-(Benzene-4-sulfonyl)-D,L-(cis-3-phenyl)prolyl-L-phenylalanine

N-Acetyl-cis-3-phenylproline ethyl ester (614 mg, 2.35 mmol) (prepared via the method of Chung, et al., *J. Org. Chem.*55: 270–275 (1990)) was dissolved in HOAc (4 mL) and 6N HCl (12 mL) and heated at reflux for 18 hr. The mixture was cooled to room temperature and the volatiles were evaporated in vacuo to give a white solid. The solid was dissolved in 1N NaOH (15 mL) and dioxane was added (10 mL), followed by 4-toluene-sulfonyl chloride (458 mg, 2.40 mmol). The mixture was stirred at room temp for 18 hr before addition of 6N HCl to bring the pH<4. The mixture was extracted with Et$_2$O (3×40 mL) and the extracts were dried (MgSO$_4$), filtered, and evaporated in vacuo to give N-(toluene-4-sulfonyl)-cis-3-phenylproline as a white solid (765 mg, 94%).

N-(Toluene-4-sulfonyl)-cis-3-phenylproline was coupled to phenylalanine ethyl ester using the procedure described in Method 3. The title compound was prepared via hydrolysis of the ethyl ester using NaOH in ethanol.

NMR data was as follows:

$^1$H NMR (CDCl$_3$): δ=8.57 (bs, 1H), 7.77 (m, 2H), 7.31–6.70 (12H), 4.65 (m, 0.5H), 4.47 (m, 0.5H), 4.41 (d, 0.5H, J=8.9 Hz), 4.34 (d, 0.5H, J=9.0 Hz). 3.73, (m, 1H), 3.28–2.76 (4H), 2.44 (s, 3H), 2.40 (m, 0.5H), 2.17 (m, 0.5H), 1.8 (m, 1H).

$^{13}$C NMR (CDCl$_3$): δ=174.5, 173.9, 169.5, 168.8, 144.3, 136.1, 135.8, 135.6, 135.3, 133.4, 133.1, 129.9, 129.6, 129.4, 128.6, 128.6, 128.3, 127.8, 127.7, 127.5, 127.1, 127.0, 65.9, 65.8, 53.6, 52.5, 48.5, 48.3, 48.2, 37.5, 37.3, 39.0, 28.6, 21.6.

Mass Spectroscopy: FAB m/e 493 (M+H).

Example 27

Synthesis of N-(4-Nitrobenzenesulfonyl)-L-prolyl-L-phenylalanine

The title compound was prepared as in Example 21 (59) except 4-nitrophenylsulfonyl chloride was used in place of 3,5-dichlorophenylsulfonyl chloride, mp=70–80° C.

NMR data was as follows:

$^1$H NMR (CDCl$_3$): δ=8.38 (d, 2H, J=8.9 Hz), 8.02 (d, 2H, J=8.9 Hz), 7.32–7.20 (6H), 4.90 (m, 1H), 4.25 (dd, 1H, J=2.5, 8.4 Hz), 3.42 (m, 2H), 3.16 (m, 2H), 1.98 (m, 1H), 1.62 (m, 2H), 1.54 (m, 1H).

$^{13}$C NMR (CDCl$_3$): δ=175.0, 171.8, 151.1, 142,5, 136.4, 129.9, 129.7, 127.8, 125.2, 62.9, 53.7, 50.3, 37.9, 30.9, 24.7.

Mass Spectroscopy: FAB m/e 448 (M+H).

Example 28

Synthesis of N-(4-Acetamidobenzenesulfonyl)-L-prolyl-L-phenylalanine

The title compound was prepared as in Example 21 (59) except 4-acetamido-phenylsulfonyl chloride is used in place of 3,5-dichlorophenylsulfonyl chloride.

NMR data was as follows:

$^1$H NMR (DMSO-d$_6$): δ=12.85 (bs, 1H), 10.4 (bs, 1H), 8.07 (d, 1H, J=8.2 Hz), 7.76 (ab q, 4H), 7.25 (m, 5H), 4.49

(dd, 2H, J=3.2, 8.2 Hz), 4.06 (m, 1H), 3.36 (m, 1H), 3.08 (3H), 2.09 (s, 3H), 1.58–1.48 (4H).

$^{13}$C NMR (DMSO-d$_6$): δ=173.0, 171.2, 169.5, 143.9, 137.8, 130.4, 129.7, 129.1, 128.5, 126.8, 119.0, 61.7, 53.5, 49.4, 37.0, 30.7, 24.6, 24.1.

Mass Spectroscopy: FAB m/e 460 (M+H).

Example 29

Synthesis of N-(4-Cyanobenzenesulfonyl)-L-prolyl-L-phenylalanine

The title compound was prepared as in Example 21 (59) except 4-cyanophenyl-sulfonyl chloride is used in place of 3,5-dichlorophenylsulfonyl chloride.

NMR data was as follows:

$^1$H NMR (CDCl$_3$): δ=8.40 (bs, 1H), 7.95 (d, 2H, J=8.3 Hz), 8.07 (d, 2H, J=8.3 Hz), 7.36–7.20 (6H), 4.93, (dt, 1H, J=5.4, 8.0 Hz), 4.22 (m, 1H), 3.38 (m, 2H), 3.13 (m, 2H), 1.92 (m, 1H), 1.56 (m, 2H), 1.40 (m, 1H).

$^{13}$C NMR (CDCl$_3$) δ=175.0, 171.9, 140.8, 136.5, 133.8, 129.9, 129.2, 129.0, 127.8, 117.8, 117.7, 62.8, 53.7, 50.3, 37.9, 30.9, 24.6.

Mass Spectroscopy: FAB mn/e 428 (M+H).

Example 30

Synthesis of N-(Toluene-4-sulfonyl)-L-prolyl-L-tryptophan

N-(Toluene-4-sulfonyl)-L-proline hydrate was coupled to L-tryptophan methyl ester hydrochloride using the procedure described in Method 3. The title compound was prepared via hydrolysis of the methyl ester using LiOH in THF/water.

NMR data was as follows:

$^1$H NMR (CDCl$_3$): δ=8.45 (d, 1H, J=2.0 Hz), 7.64 (d, 2H, J=8.2 Hz), 7.60 (d, 1H, J=7.6 Hz), 7.45 (d, 1H, J=7.4 Hz), 7.33 (d, 1H, J=8.0 Hz), 7.27 (d, 2H, J=8.0 Hz), 7.19–7.06 (3H), 4.88 (m, 1H), 4.07 (dd, 1H, J=2.9, 8.6 Hz), 3.48 (dd, 1H, J=5.4, 14.8 Hz), 3.36 (dd, 1H, J=7.1, 14.8 Hz), 3.03 (m, 2H), 2.40 (s, 3H), 1.88 (m, 1H), 1.47 (m, 1H), 1.32 (m, 1H), 1.22 (m, 1H).

$^{13}$C NMR (CDCl$_3$): δ=174.8, 172.7, 145.0, 136.7, 133.3, 130.6, 128.4, 128.3, 124.3, 122.6, 118.9, 112.0, 110.0, 62.8, 54.0, 50.1, 30.5, 27.5, 24.6, 22.1.

Mass Spectroscopy: FAB m/e 456 (M+H).

Example 31

Synthesis of N-(Toluene-4-sulfonyl)-L-prolyl-β-(1-naphthyl)-L-alanine

N-(Toluene-4-sulfonyl)-L-proline hydrate was coupled to β-(1-naphthyl)alanine methyl ester hydrochloride using the procedure described in Method 3. The title compound was prepared via hydrolysis of the methyl ester using LiOH in THF/water.

NMR data was as follows:

$^1$H NMR (CDCl$_3$): δ=8.16 (d, 1H, J=8.2 Hz), 8.05 (bs, 1H), 7.85 (d, 1H, J=6.9 Hz), 7.77–7.27 (10H), 4.99 (m, 1H), 4.05 (m, 1H), 3.90 (dd, 1H, J=5.0; 14.3 Hz), 3.51 (dd, 1H, J=9.6, 14.3 Hz), 3.11 (m, 1H), 3.02 (m, 1H), 2.41 (s, 3H), 1.74 (m, 1H), 1.34 (m, 2H), 1.00 (m, 1H).

$^{13}$C NMR (CDCl$_3$): δ=174.9, 172.5, 145.0, 134.4, 133.4, 133.1, 132.6, 130.6, 129.4, 128.5, 128.4, 127.2, 126.4, 126.0, 14.0, 62.7, 53.9, 50.1, 34.9, 30.3, 24.5, 22.1.

Mass Spectroscopy: FAB m/e 467 (M+H).

Example 32

Synthesis of N-(Toluene-4-sulfonyl)-L-prolyl-β-(2-naphthyl)-L-alanine

N-(Toluene-4-sulfonyl)-L-proline hydrate was coupled to β-(2-naphthyl)-L-alanine methyl ester hydrochloride using the procedure described in Method 3. The title compound was prepared via hydrolysis of the methyl ester using LiOH in THF/water.

NMR data was as follows:

$^1$H NMR (CDCl$_3$): δ=8.20 (bs, 1H), 7.80–7.67 (6H), 7.55 (d, 1H, J =7.9 Hz), 7.46–7.27 (5H), 4.99 (m, 1H), 4.12 (m, 1H), 3.55 (m, 1H), 3.27 (dd, 1H, J=8.2, 14.1 Hz), 3.17 (m, 1H), 3.01 (m, 1H), 2.39 (s, 3H), 1.83 (m, 1H), 1.40–1.26 (3H).

$^{13}$C NMR (CDCl$_3$): δ=174.8, 172.4, 145.0, 134.3, 133.9, 133.4, 133.0, 130.6, 128.9, 128.8, 128.4, 128.2, 128.1, 127.9, 126.7, 126.3, 62.7, 53.9, 50.1, 38.2, 30.4, 24.5, 22.1.

Mass Spectroscopy: FAB m/e 467 (M+H).

Example 33

Synthesis of N-(Toluene-4-sulfonyl)-L-prolyl-β-(2-thienyl)-L-alanine

N-(Toluene-4-sulfonyl)-L-proline hydrate was coupled to β-(2-thienyl)-L-alanine methyl ester hydrochloride using the procedure described in Method 3. The title compound was prepared via hydrolysis of the methyl ester using LiOH in THF/water.

NMR data was as follows:

$^1$H NMR (CDCl$_3$): δ=8.42 (bs, 1H), 7.73 (d, 2H, J=8.3 Hz), 7.57 (d, 1H, J=7.4 Hz), 7.34 (d, 2H, J=7.9 Hz), 7.16 (dd, 1H, J=1.2, 5.1 Hz), 6.95–6.88 (m, 2H), 4.87 (m, 1H), 4.18 (m, 1H) 3.56–3.41 (3H), 3.17 (m, 1H), 2.43 (s, 3H), 2.08 (m, 1H), 1.60 (m, 3H).

$^{13}$C NMR (CDCl$_3$): δ=174.2, 172.6, 145.1, 137.9, 133.4, 130.6, 128.5, 127.7, 127.6, 125.4, 62.8, 54.0, 50.4, 32.11, 30.7, 24.9, 22.2

Mass Spectroscopy: FAB m/e 423 (M+H).

Example 34

Synthesis of N-(Isopropanesulfonyl)-L-prolyl-L-phenylalanine

Substitution of (CH3)$_2$CHSO$_2$Cl for CH$_3$SO$_2$Cl, and following the procedures described in Example 1 (9), gave the title compound as a clear oil.

NMR data was as follows:

$^1$H NMR (DMSO-d$_6$, 300 MHz): δ=8.10 (d, J=7.9, 1H), 7.28–7.16 (m, 5H), 4.48–4.41 (m, 1H), 4.27–4.24 (m, 1H), 3.47–3.23 (m, 3H), 3.11–3.00 (m, 2H), 2.89 (dd, J=13.9, J=9.4, 1H), 2.11–2.01 (m, 1H), 1.82–1.71 (m, 3H), 1.11 (d, J=6.8, 6H).

$^{13}$C NMR (DMSO-d$_6$, 75 MHz): δ=172.6, 171.1, 137.4, 129.2, 128.1, 126.4, 61.2, 53.0, 48.6, 43.6, 36.5, 30.6, 24.0, 20.0, 19.8

Mass Spectroscopy: (+FAB, 3-nitrobenzyl alcohol) 369 (MH+).

Example 35

Synthesis of N-(Toluene-4-sulfonyl)-L-prolyl-β-(3-pyridyl)-L-alanine

N-(Toluene-4-sulfonyl)-L-proline hydrate was coupled to L-β-(3-pyridyl)alanine methyl ester dihydrochloride using the procedure described in Method 3 to give N-(toluene-4-sulfonyl)prolyl-L-β-(3-pyridyl)alanine. The title compound was prepared via hydrolysis of the methyl ester using 0.5 N aqueous NaOH in THF/water.

NMR data was as follows:

$^1$H NMR (DMSO-d$_6$): δ=8.33 (dd, 1H, J=1.4, 4.7 Hz), 8.27 (d, 1H, J=1.9 Hz), 7.75 (d, 2H, J=8.2 Hz), 7.71 (m, 1H), 7.52 (m, 1H), 7.42 (d, 2H, J=8.5 Hz), 7.19 (dd, 1H, J=4.7, 7.7 Hz), 4.00 (m, 2H), 3.20–3.00 (4H), 2.40 (s, 3H), 1.72 (m, 1H), 1.40 (3H).

$^{13}$C NMR (DMSO-d$_6$): δ=172.7, 170.0, 150.9, 147.4, 144.1, 137.4, 134.6, 133.8, 130.3, 128.1, 123.1, 62.4, 55.1, 49.3, 34.4, 30.5, 24.00, 21.4.

Mass Spectroscopy: FAB m/e 440 (M+Na).

Example 36

Synthesis of N-(Toluene-4-sulfonyl)-L-(cis-4-phenylthio)prolyl-L-phenylalanine Trans-4-hydroxy-L-proline was treated with EtOH and HCl gas, and the mixture was evaporated to give trans-4-hydroxy-L-proline ethyl ester hydrochloride. This product was treated with TsCl in pyridine, to give after aqueous workup N-(toluene-4-sulfonyl)-trans-4-(O-(toluene-4-sulfonyl))-L-proline ethyl ester. This product was treated with PhSH and DBU in DMF to give after aqueous workup and flash chromatography on silica gel, N-(Toluene-4-sulfonyl)-cis-4-(phenylthio)-L-proline ethyl ester. This product was treated with NaOH in CH$_3$OH and H$_2$O, to give after acidification, extraction, drying with MgSO$_4$, filtration and evaporation, N-(toluene-4-sulfonyl)-cis-4-(phenylthio)-L-proline. This product was treated with HCl.Phe-OMe, BOP, and NMM in DMF, to give, after aqueous workup and flash chromatography, N-(toluene-4-sulfonyl)-cis-4-(phenylthio)-Pro-Phe-OMe. This product was treated with NaOH in CH$_3$OH and H$_2$O, to give, after acidification, extraction, drying with MgSO$^4$, filtration and evaporation, the title compound as a clear oil.

NMR data was as follows:
$^1$H NMR (DMSO-d$_6$, 300 MHz): δ=8.19 (d, J=8.0, 1H), 7.71 (d, J=8.3, 2H), 7.41 (d, J=8.2, 2H), 7.35–7.14 (m, 10H), 4.53–4.46 (m, 1H), 4.24 (t, J=7.8, 1H), 3.73 (dd, J=11.6, J=6.7, 1H), 3.36 (bs, 1H), 3.17–2.86 (m, 4H), 2.39 (s, 3H), 2.34–2.25 (m, 1H), 1.57–1.47 (m, 1H).

$^{13}$C NMR (DMSO-d$_6$, 75 MHz): δ=172.4, 170.0, 144.0, 137.3, 134.1, 133.9, 130.0, 129.8, 129.4, 129.3, 128.2, 127.5, 126.9, 126.5, 61.0, 54.9, 53.2, 42.3, 36.7, 36.4, 21.1.

Mass Spectroscopy: (+FAB, 3-nitrobenzyl alcohol) 525 (MH+).

Example 37

Synthesis of N-(Toluene-4-sulfonyl)-L-(cis-4-benzylthio)prolyl-L-phenylalanine Substitution of benzylthiol for phenylthiol, and following the methods for preparation of Example 36 (131), gave the title compound as a clear oil.

NMR data was as follows:
$^1$H NMR (DMSO-d$_6$, 300 MHz) δ=8.18 (d, J=8.1, 1H), 7.65 (d, J=8.3, 2H), 7.38 (d, J=8.2, 2H), 7.29–7.17 (m, 10H), 4.50–4.43 (m, 1H), 4.05 (t, J=7.9, 1H), 3.74–3.56 (m, 3H), 3.35 (bs, 1H), 3.09–2.94 (m, 4H), 2.40 (s, 3H), 2.20–2.10 (m, 1H), 1.40–1.28 (m, 1H).

$^{13}$C NMR (DMSO-d$_6$, 75 MHz): δ=172.4, 170.2, 143.8, 138.5, 137.3, 134.0, 130.0, 129.4, 128.7, 128.4, 128.2, 127.3, 126.9, 126.5, 60.9, 55.5, 53.1, 39.3, 36.7, 36.6, 34.9, 21.1.

Mass Spectroscopy: (+FAB, 3-nitrobenzyl alcohol) 539 (MH+).

Example 38

Synthesis of N-(Toluene-4-sulfonyl)-L-prolyl-L-histidine

N-(Toluene-4-sulfonyl)prolyl-L-(N-benzyl)histidine (237 mg, 0.464 mmol) was dissolved in MeOH (20 mL) and 10% Pd/C (50 mg) was added. The mixture was hydrogenated at 50 psi H$_2$ for 36 hr. The mixture was filtered to remove the catalyst and the filtrate was evaporated in vacuo. The residue was purified by preparative TLC (90:10:1 CH$_2$Cl$_2$/MeOH/NH$_4$OH) to give N-(toluene-4-sulfonyl)-L-prolyl-L-histidine methyl ester (155 mg, 79%). The title compound was prepared via hydrolysis of the methyl ester using 0.5 N NaOH in THF/water (128 mg, 81%).

NMR data was as follows:
$^1$H NMR (DMSO-d$_6$); δ=7.77 (d, 3H, J=6.5 Hz), 7.42 (m,3H), 4.03 (m, 1H), 3.99 (m, 1H), 3.22 (m, 1H), 3.05 (m 2H), 2.95 (m, 1H), 2.41 (s, 3H), 1.80 (m, 1H), 1.45 (3H).

$^{13}$C NMR (DMSO-d$_6$): δ=174.0, 169.8, 144.1, 133.8, 10.3, 128.0, 62.4, 49.4, 40.0, 30.6, 24.0, 21.4.

Mass Spectroscopy: FAB m/e 429 (M+Na).

Example 39

Synthesis of N-(Toluene-4-sulfonyl)-L-(cis-4-anino)prolyl-L-phenylalanine

Trans-4-hydroxy-L-proline was treated with EtOH and HCl gas, and the mixture was evaporated to give trans-4-hydroxy-L-proline ethyl ester hydrochloride. This product was treated with TsCl in pyridine to give, after aqueous workup, N-(toluene-4-sulfonyl)-trans-4-(TsO)-L-proline ethyl ester. This product was treated with NaN$_3$ in DMF and H$_2$O to give, after aqueous workup and flash chromatography, N-(toluene-4-sulfonyl)-cis-4-azido-L-proline ethyl ester. This product was treated with NaOH in CH$_3$OH and H$_2$O to give, after acidification, extraction, drying with MgSO$_4$, filtration and evaporation, N-(toluene-4-sulfonyl)-cis-4-azido-L-proline. This product was treated with 10% Pd on C in THF, AcOH and H$_2$O, and the mixture was shaken under 50 psi H$_2$. The mixture was filtered through Celite and evaporated to give N-(toluene-4-sulfonyl)-cis-4-anino-L-proline. This product was treated with Boc$_2$O and Et$_3$N in t-BuOH and H$_2$O to give, after evaporation, acidification, extraction, drying with MgSO$_4$, filtration, and evaporation, N-(toluene-4-sulfonyl)-cis-4-(t-butoxycarbonylamino)-L-proline. This product was treated with HCl.Phe-O-t-Bu, BOP, and NMM in DMF to give, after aqueous workup and flash chromatography, N-(toluene-4-sulfonyl)-cis-4-(t-butoxycarbonylamino)-Pro-Phe-O-t-Bu. This product was treated with TFA to give after evaporation the trifluoroacetate salt of the title compound as a clear oil.

NMR data was as follows:
$^1$H NMR (CD$_3$OD, 300 MHz): δ=7.47 (d, J=8.3, 2H), 7.22–7.00 (m, 7H), 4.47 (dd, J=7.9, J=5.3, 1H), 4.18 (dd, J=9.8, J=1.7, 1H), 3.64 (t, J=5.2, 1H), 3.43 (d, J=11.2, 1H), 3.22 (dd, J=11.3, J=5.0, 1H), 3.01 (dd, J=14.1, J=5.3, 1H), 2.88 (dd, J=14.0, J=7.9, 1H), 2.23 (s, 3H), 2.21–2.08 (m, 1H), 1.87–1.80 (m, 1H).

$^{13}$C NMR (CD$_3$OD, 75 MHz): δ=174.7, 173.9, 146.1, 138.0, 134.7, 131.1, 130.5, 129.6, 128.7, 128.0, 60.7, 55.6, 53.9, 51.5, 38.2, 35.3, 21.5.

Mass Spectroscopy: (+FAB, 3-nitrobenzyl alcohol) 432 (MH+).

Example 40

Synthesis of N-(Toluene-4-sulfonyl)-L-(trans-4-amino)prolyl-L-phenylalanine Substitution of cis-4-hydroxy-L-proline for trans-4-hydroxy-L-proline, and following the methods for preparation of Example 39 (136), gave the trifluoroacetate salt of the title compound as a clear oil.

NMR data was as follows:

$^1$H NMR (CD$_3$OD, 300 MHz): δ=7.39 (d, J=8.4, 2H), 7.13–7.01 (m, 7H), 4.40–4.33 (m, 1H), 4.28 (dd, J=9.0, J=2.2, 1H), 3.59–3.50 (m, 2H), 3.07–2.97 (m, 2H), 2.81 (dd, J=14.0, J=8.9, 1H), 2.21 (s, 3H), 1.24–2.06 (m, 1H), 1.80–1.68 (m, 1H).

$^{13}$C NMR (CD$_3$OD, 75 MHz): δ=174.1, 172.6, 145.9, 138.3, 135.0, 131.0, 130.5, 129.6, 128.9, 128.0, 61.1, 55.2, 52.0, 49.7, 38.2, 35.4, 21.5.

Mass Spectroscopy: (+FAB, 3-nitrobenzyl alcohol) 432 (MH+).

Example 41

Synthesis of N-(Toluene-4-sulfonyl)-L-prolyl-L-phenylalanine Benzyl Ester

N-(Toluene-4-sulfonyl)-L-proline was coupled to L-phenylalanine benzyl ester toluenesulfonic acid salt using the procedure described in Method 3 to give the title compound as an oil.

NMR data was as follows:

$^1$H NMR (CDCl$_3$): δ=7.68 (d, 2H, J=8.2 Hz), 7.39–7.17 (10H), 7.05 (m, 1H), 5.22 (d, 2H, J=12.2 Hz), 5.14 (d, 1H, J=12.2 Hz), 4.88 (m, 1H), 4.08 (m, 1H), 3.28 (m, 3H), 3.08 (m, 2H), 2.39 (s, 3H), 2.00 (m, 1H), 1.46 (m, 3H).

$^{13}$C NMR (CDCl$_3$): δ=171.4, 171.3, 144.9, 136.5, 135.8, 133.6, 130.6, 129.9, 129.1, 129.1, 129.0, 129.0, 128.4, 127.6, 67.8, 62.8, 54.0, 50.2, 38.4, 30.4, 24.8, 22.2.

Mass Spectroscopy: FAB m/e 507 (M+H).

Example 42

Synthesis of N-(Toluene-4-sulfonyl)-L-prolyl-L-phenylalanine N-Methoxyamide

N-(Toluene-4-sulfonyl)-L-prolyl-L-phenylalanine was coupled to O-methylhydroxylamine hydrochloride using the mixed anhydride procedure (as described in Greenstein, J. P. and Milton Wenitz, "Chemistry of the Amino Acids," volume 2, pp. 978–979, Robert E. Krieger Publishing Co., Malabar, Fla. (1961)) to give the title compound as an oil.

NMR data was as follows:

$^1$H NMR (CDCl$_3$): δ=9.66 (s, 1H), 7.70 (d, 2H, J=8.2 Hz), 7.36 (d, 2H, J=8.0 Hz), 7.33–7.21 (5H), 6.90 (d, 1H, J=9.5 Hz), 4.88 (m, 1H), 3.81 (m, 1H), 3.75 (s, 3H), 3.46 (m, 2H), 3.07 (m, 2H), 2.45 (s, 3H), 1.60 (m, 2H), 1.47 (m, 2H).

$^{13}$C NMR (CDCl$_3$): δ=171.7, 168.1, 145.6, 137.0, 131.8, 130.7, 129.7, 129.3, 128.5, 127.7, 64.9, 62.7, 52.6, 50.6, 37.6, 31.4, 24.7, 22.2.

Mass Spectroscopy: FAB m/e 446 (M+H).

Example 43

Synthesis of N-(Toluene-4-sulfonyl)-L-prolyl-L-phenylalanine N-Benzyloxyamide

N-(Toluene-4-sulfonyl)-L-prolyl-L-phenylalanine was coupled to O-benzylhydroxylamine using the procedure described in Method 3 to give the title compound as a white solid, mp=127–130° C.

NMR data was as follows:

$^1$H NMR (CDCl$_3$): δ=9.54 (s, 1H), 7.61 (d, 2H, J=8.2 Hz), 7.43–7.19 (12H), 6.86 (d, 1H, J=9.3 Hz), 4.91 (m, 2H), 4.82 (m, 1H), 3.72 (m, 1H), 3.42 (m, 2H), 3.07 (m, 2H), 2.45 (s, 3H), 1.64 (m, 2H), 1.44 (m, 1H), 1.26 (m, 1H).

$^{13}$C NMR (CDCl$_3$): δ=171.6, 168.2, 145.5, 136.9, 135.7, 132.0, 130.7, 129.9, 129.7, 129.0, 128.9, 128.5, 127.7, 78.8, 62.7, 52.7, 50.6, 37.6, 31.2, 24.7, 22.2.

Mass Spectroscopy: FAB m/e 522 (M+H).

Example 44

Synthesis of N-(Toluene-4-sulfonyl)-L-prolyl-L-phenylalanine N-(Toluene-4-sulfonyl)amide N-(Toluene-4-sulfonyl)-L-proline was reacted with L-phenylalanine amide using the procedure described in Method 12 to yield N-(toluene-4-sulfonyl)-L-prolyl-L-phenylalanine amide. To a solution of NaH (60% mineral oil—prewashed with THF) in THF at 0° C. was added N-(toluene-4-sulfonyl)-L-prolyl-L-phenylalanine amide and the reaction was stirred at 0° C. for 45 minutes. Toluene-4-sulfonyl chloride was added and the reaction was stirred for 16 hours at room temperature. The reaction mixture was extracted with EtOAc (3×50 mL) and 0.2 N HCl (50 mL), and the combined organic layers were washed successively with sat. NaHCO$_3$ (50 mL), and sat. NaCl (2×50 mL), dried over MgSO$_4$, filtered, and concentrated to yield the title compound as an oil.

NMR data was as follows:

$^1$H NMR (CDCl$_3$, 300 MHz): δ=7.97 (d, 2H, 8.52 Hz); 7.72 (d, 2H, 8.52 Hz); 7.37–7.04 (m, 10 H); 4.80 (m, 1H); 3.86 (m, 1H); 3.42 (m, 1H); 3.29 (m, 1H); 3.01 (m, 2H); 2.45 (bs, 6H); 1.65 (m 2H); 1.45 & 1.31 (m, 2H).

$^{13}$C NMR (CDCl$_3$, 300 MHz): δ=172.46, 169.93, 145.47, 136.43, 132.06, 130.70, 130.07, 129.58, 129.32, 129.17, 128.61, 127.74, 62.68, 54.52, 50.57, 36.91, 31.10, 24.69, 22.30, 22.23.

Mass Spectroscopy: (+FAB) 570 (M+H).

Preparative Example A

Synthesis of N-(Toluene-4-sulfonyl)-L-prolyl-D,L-phenyalanyl-β-alanine Ethyl Ester To N-(toluene-4-sulfonyl)-L-prolyl-L-phenylalanine (~2 eq.) in DMF was added BOP (~2.1 eq.) and NMM (~4 eq.), and the reaction was stirred at room temperature for about 45 minutes. β-alanine ethyl ester (~2 eq.) was added and the reaction stirred for about 16 hours at room temperature. The reaction mixture was extracted with water and diethyl ether. The combined organic solution was then washed with 0.2 N HCl, sat. NaHCO$_3$ and sat. NaCl solutions. The organic layer was dried over anhydrous magnesium sulfate, filtered and concentrated. The residue was purified by silica gel chromatography (50% EtOAc/Hexane, Rf=0.18) to yield the title compound as a colorless oil, which was determined to be a mixture of diastereomers by NMR.

NMR data was as follows:

$^1$H NMR (CDCl$_3$, 300 MHz): δ=7.68 (m, 2H); 7.25 (m, 9H); 4.07 (m, 3H); 3.45 (m, 4H); 3.06 (m, 3H); 2.50 & 2.34 (m, 3H), 2.41 (s, 3H), 1.62 (m, 4H); 1.20 (t, 3H, J=5.55 Hz).

$^{13}$C NMR (CDCl$_3$, 300 MHz): δ=177.62, 172.72, 171.98, 171.73, 171. 25, 170.80, 145.39, 145.02, 137.52, 137.20, 133.28, 132.09, 133.28, 132.09, 130.66, 130.57, 130.02, 129.59, 129.18, 128.49, 128.44, 127.49, 127.46, 63.06, 62.75, 61.18, 61.12, 55.49, 54.17, 50.62, 50.36, 38.27, 37.92, 35.98, 35.32, 34.47, 34.30, 31.27, 30.95, 24.92, 24.62, 22.18, 14.72.

Mass Spectroscopy: (+FAB) 516 (M+H).

Example 45

Synthesis of N-(Toluene-4-sulfonyl)-L-prolyl-D,L-phenylalanyl-β-alanine

The title compound was prepared from Preparative Example A (161) using the procedure described for Example 19 (57), yielding a translucent solid, which was determined to be a mixture of diastereomers by NMR, mp=91–95° C.

NMR data was as follows:

$^1$H NMR (CDCl$_3$, 300 MHz): δ=7.70 & 7.27 (m, 9H); 4.83 (m, 0.5 H); 4.05 (m, 0.5 H); 3.47 (m, 4H); 3.06 (m, 3H); 2.55 (m, 2H); 2.43 (s, 3H); 1.62 (m, 4H).

$^{13}$C NMR (CDCl$_3$, 300 MHz): δ=175.85, 175.68, 172.45, 172.23, 171.67, 171.43, 145.32, 144.96, 137.37, 136.91, 133.42, 132.37, 130.67, 130.56, 130.52, 130.03, 129.65, 129.15, 129.12, 128.51, 128.48, 127.52, 63.01, 62.72, 55.25, 54.34, 50.52, 50.43, 50.39, 38.81,.38.07, 35.82, 35.79, 35.25, 35.23, 34.17, 34.10, 34.08, 31.23, 24.91, 24.61, 22.18.

Mass Spectroscopy: (+FAB) 488 (M+H).

Example 46

Synthesis of N-(Toluene-4-sulfonyl)-L-prolyl-L-phenylalanine N-Hydroxyamide N-(Toluene-4-sulfonyl)-L-prolyl-L-phenylalanine N-benzyloxyamide (see Example 43 (159)) was dissolved in MeOH (10 mL) and 5% Pd/BaSO$_4$ (52 mg) was added. The mixture was hydrogenated at 50 psi H$_2$ for 9 h. The mixture was filtered through a pad of diatomaceous earth and evaporated in vacuo to give a residue which was purified by silica gel chromatography (92:8 CH$_2$Cl$_2$/MeOH) to give the title compound as an oil.

NMR data was as follows:

$^1$H NMR (CDCl$_3$): δ=9.85 (br s, 1H), 7.73 (d, 2H, J=7.2 Hz), 7.36 (d, 2H, J=7.0 Hz), 7.28–7.20 (5H), 7.07 (m, 1H), 4.96 (m, 1H), 3.87 (m, 1H), 3.47 (m, 2H), 3.07 (m, 2H), 2.45 (s, 3H), 1.90 (br s, 1H), 1.63 (m, 2H), 1.46 (m, 1H), 1.36 (m, 1H).

$^{13}$C NMR (CDCl$_3$): δ=171.8, 168.4, 145.5, 136.9, 132.0, 130.7, 129.7, 129.2, 128.6, 127.6, 62.7, 52.2, 50.6, 38.0, 31.2, 24.6, 22.2.

Mass Spectroscopy: FAB m/e 432 (M+H).

Example 47

Synthesis of N-(Toluene-4-sulfonyl)-L-prolyl-L-phenylalanine Isopropyl Ester N-(Toluene-4-sulfonyl)-L-proline hydrate was coupled to phenylalanine isopropyl ester trifluoroacetate using the procedure described in Method 3 to give the title compound as an oil.

NMR data was as follows:

$^1$H NMR (CDCl$_3$): δ=7.68 (d, 2H, J=8.2 Hz), 7.33–7.12 (8H), 5.05 (p, 1H, J=6.3 Hz), 4.77 (m, 1H), 4.06 (m, 1H), 3.33 (m, 1H), 3.22 (dd, 1H, J=5.8, 14.0 Hz), 3.06 (m, 2H), 2.40 (s, 3H), 1.99 (m, 1H), 1.46 (3H), 1.23 (d, 6H, J=6.3 Hz).

$^{13}$C NMR (CDCl$_3$): δ=171.3, 170.9, 144.9, 136.7, 133.5, 130.5, 129.9, 129.0, 128.4, 127.5, 70.0, 62.9, 54.0, 50.2, 38.5, 30.4, 24.7, 22.3, 22.2, 22.1.

Mass Spectroscopy: FAB m/e 459 (M+H)

Example 48

Synthesis of N-(Toluene-4-sulfonyl)-L-(cis-4-hydroxy)-prolyl-L-phenylalanine Substitution of cis4-hydroxy-L-proline for D-Pro-OH, and following the methods described in Example 6 (17), gave the title compound as a clear oil.

NMR data was as follows:

$^1$H NMR (DMSO-d$_6$, 300 MHz): δ=8.14 (d, J=7.9, 1H), 7.70 (d, J=8.2, 2H), 7.41 (d, J=8.2, 2H), 7.28–7.15 (m, 5H), 5.30 (bs, 1H), 4.52–2.45 (m, 1H), 4.15 (dd, J=9.0, J=4.1, 1H), 3.85 (bs, 1H), 3.31 (bs, 1H), 3.24 (dd, J=10.6, J=4.9, 1H), 3.17 (dd, J=10.9, J=3.4, 1H), 3.01–2.94 (m, 2H), 2.40 (s, 3H), 1.92–1.82 (m, 1H), 1.79–1.69 (m, 1H).

$^{13}$C NMR (DMSO-d$_6$, 75 MHz): δ=172.2, 171.2, 143.8, 136.9, 133.4, 129.9, 129.5, 128.1, 127.59 126.5, 68.6, 60.3, 56.4, 53.4, 38.0, 37.0, 21.0.

Mass Spectroscopy: (+FAB, 3-nitrobenzyl alcohol) 433 (MH+).

Example 49

Synthesis of N-(Toluene-4-sulfonyl)-L-(trans-4-fluoro)-prolyl-L-phenylalanine Benzyl Ester Substitution of cis-4-hydroxy-L-proline for trans-4-hydroxy-L-proline, and following the methods for preparation of Example 50 (177), gave the title compound as a clear oil.

NMR data was as follows:

$^1$H NMR (CDCl$_3$, 300 MHz): δ=7.70 (d, J=8.3, 2H), 7.41–7.20 (m, 10H), 7.10–7.07 (m, 2H), 5.24 (dd, J=12.1, 1H), 5.16 (dd, J=12.2, 1H), 4.93–4.87 (m, 1H), 4.88 (bd, J=52.4, 1H), 4.15–4.09 (m, 1H), 3.80 (ddd, J=1.6, J=20.7, J=12.5, 1H), 3.37 (ddd, J=3.1, J=13.9, J=36.8, 1H), 3.28 (dd, J=13.9, J=5.8, 1H), 3.06 (dd, J=13.9, J=7.2, 1H), 2.43 (s, 3H), 2.32–2.18 (m, 1H), 2.11–1.91 (m, 1H).

$^{13}$C NMR (CDCl$_3$, 75 MHz): δ=170.7, 170.0, 144.4, 135.8, 135.1, 129.7, 129.4, 128.58, 128.56, 128.4, 128.1, 127.0, 91.2 (d, J=181.0 Hz), 67.3, 60.8, 55.6 (d, J=23.0 Hz), 53.2, 37.9, 37.0 (d, J=22.0 Hz), 21.6.

Mass Spectroscopy: (+FAB, 3-nitrobenzyl alcohol) 525 (MH+).

Example 50

Synthesis of N-(Toluene-4-sulfonyl)-L-(cis-4-fluoro)-prolyl-L-phenylalanine Benzyl Ester Trans-4-hydroxy-L-proline was treated with EtOH and HCl gas, and the mixture was evaporated to give trans-4-hydroxy-L-proline ethyl ester hydrochloride. This product was treated with TsCI and Et$_3$N in CH$_2$Cl$_2$, to give after aqueous workup N-(toluene-4-sulfonyl)-trans-4-hydroxy-L-proline ethyl ester. This product was treated with morpholinosulfur trifluoride in CH$_2$Cl$_2$, to give after aqueous workup N-(toluene-4-sulfonyl)-cis-4-fluoro-L-proline ethyl ester. This product was treated with NaOH in CH$_3$OH and H$_2$O to give, after acidification, extraction, drying with MgSO$^4$, filtration and evaporation, N-(toluene-4-sulfonyl)-cis-4-fluoro-L-proline. This product was treated with HCl.Phe-OBn, BOP, and NMM in DMF, to give after aqueous workup and flash chromatography the title compound as a clear oil.

NMR data was as follows:

$^1$H NMR (CDCl$_3$, 300 MHz): δ=7.69 (d, J=8.3, 2H), 7.41 (d, J=7.8, 1H), 7.38–7.27 (m, 7H), 7.21–7.17 (m, 3H), 7.07–7.04 (m, 2H), 5.19 (d, J=12.1, 1H), 5.12 (d, J=12.1, 1H), 5.05 (dt, Jd=52.7, Jt=3.4, 1H), 4.89 (dt, Jd=7.9, Jt=6.0, 1H), 4.27 (d, J=9.9, 1H), 3.68 (ddd, J=1.6, J=12.6, J=21.1, 1H), 3.37 (ddd, J=3.7, J=12.4, J=35.7, 1H) 3.13 (dd, J=5.9, J=13.8, 1H), 3.08 (dd, J=6.1, J=13.8, 1H), 2.62 (t, J=15.9, 1H), 2.43 (s, 3H), 1.82–1.59 (m, 1H).

$^{13}$C NMR (CDCl$_3$, 75 MHz): δ=170.5, 169.9, 144.8, 135.5, 135.1, 132.4, 130.1, 129.41, 129.39, 128.6, 128.5, 128.4, 127.9, 126.9, 91.7 (d, J=179.4 Hz), 67.1, 55.6 (d, J=23.8 Hz), 36.3 (d, J=21.5 Hz), 21.6.

Mass Spectroscopy: (+FAB, 3-nitrobenzyl alcohol) 525 (MH+).

Example 51

Synthesis of N-(Toluene-4-sulfonyl)-L-thiaprolyl-L-phenylalanine Benzyl Ester The title compound was prepared following the procedure outlined for the preparation of Example 3 (11).

NMR data was as follows:

$^1$H NMR (CDCl$_3$, 300 MHz): δ=2.45 (s, 3H), 3.05–3.35 (m, 2H), 4.03 (d, 1H, J=10.3 Hz), 4.55 (d, 1H, J=10.3 Hz), 4.60 (m, 1H), 4.86 (m, 1H), 5.20 (dd, 2H, J=12.1 and 13.6 Hz), 7.03 (m, 1H), 7.14–7.40 (m, 12H), 7.70 (d, 2H, J=8.2 Hz).

$^{13}$C NMR (CDCl$_3$, 75 MHz): δ=22.3, 33.5, 38.1, 52.0, 54.2, 65.8, 68.0, 127.8, 128.5, 129.1, 129.2, 129.9, 130.7, 134.0, 135.6, 136.0, 145.6, 168.7, 171.1.

Mass Spectroscopy: (FAB+) 525 (M+H).

Example 52

Synthesis of N-(Toluene-4-sulfonyl)-L-(5,5-dimethyl)thiaprolyl-L-phenylalanine Benzyl Ester The title compound was prepared following the procedure described for the preparation of Example 3 (11).

NMR data was as follows:

$^1$H NMR (CDCl$_3$, 300 MHz): δ=1.10 (s, 6H), 2.44 (s, 3H), 3.08–3.14 (m, 2H), 3.85 (s, 1H), 4.39 (d, 1H, J=9.7 Hz), 4.52 (d, 1H, J=9.7 Hz), 4.94 (m, 1H), 5.17 (m, 2H), 7.01 (d, 1H, J=2.5 Hz), 7.10–7.40 (m, 12H), 7.74 (d, 2H, J=8.3 Hz).

$^{13}$C NMR (CDCl$_3$, 75 MHz): δ=22.3, 24.5, 29.8, 38.9, 51.2, 53.9, 55.2, 67.9, 74.1, 127.6, 128.7, 129.0, 129.1, 129.2, 129.3, 130.0, 130.5, 133.3, 135.7, 136.4, 145.3, 169.0, 171.3.

Mass Spectroscopy: (FAB+) 553 (M+H).

Example 53

Synthesis of N-(2-Methoxycarbonylbenzenesulfonyl)-L-prolyl-L-phenylalanine Benzyl Ester To L-prolyl-L-phenylalanine benzyl ester (4.64 mmoles) in THF (15 mL) was added triethylamine (4.70 mmoles) and the reaction proceeded for 30 minutes at room temperature. The reaction mixture was chilled to 0° C. and methyl 2-(chlorosulfonyl) benzoate (4.64 mmoles) was added and the reaction proceeded for 4 hours at room temperature. The reaction was extracted with EtOAc (3×50 mL) and water (50 mL), and the combined organic layers were successively washed with sat. NaHCO$_3$ (50 mL) and sat NaCl (2×50 mL), dried over MgSO$_4$, filtered and roto-evaporated to yield a colorless oil (2.30 g, 90%). The crude product was purified by silica gel chromatography (50% EtOAc/Hexane, Rf=0.47) to yield a colorless oil (1.49 g, 58%).

NMR data was as follows:

$^1$H NMR (CDCl$_3$, 300 MHz): δ=7.88 (d, 1H, J=7.29 Hz); 7.48 & 7.16 (m, 14H); 5.04 (m, 2H); 4.75 (m, 1H); 4.37 (d, 1H, 6.92 Hz); 3.86 (s, 3H); 3.40 & 3.28 (m, 2H); 3.06 (m, 2H); 1.75, 1.61, & 1.32 (m, 4H).

$^{13}$C NMR (CDCl$_3$, 300 MHz): δ=171.61, 171.32, 171.23, 169.03, 136.75, 135.89, 135. 51, 133.89, 133.62, 131.14, 130.34, 129.77, 129.38, 129.09, 129.00, 128.96, 128.88, 128.79, 127.48, 62.13, 60.90, 53.97, 49.48, 38.10, 31.07, 24.48, 21.56.

Mass Spectroscopy: (+FAB) 551 (M+H).

Example 54

Synthesis of N-(3,5-Dichlorobenzenesulfonyl)-L-prolyl-L-phenylalanine

L-Proline methyl ester hydrochloride (2.68 g, 16.2 mmol) was dissolved in pyridine (20 mL), 3,5-dichlorophenylsulfonyl chloride (3.57 g, 14.6 mmol) was added and the mixture was stirred for 19 hr. Water (5 mL) was added and the mixture was stirred for 45 min before diluting with water (200 mL). The mixture was extracted with Et$_2$O (2×150 mL) and the combined extracts were washed with water (3×100 mL), 1N HCl (150 mL) and saturated aq NaHCO$_3$ (150 mL), then dried (MgSO$_4$), filtered and evaporated in vacuo to give 3,5-dichlorophenylsulfonyl-L-proline methyl ester as an oil (4.34 g, 88%).

The methyl ester was dissolved in MeOH (20 mL) and 1N NaOH (20 mL) was added. The mixture was gently warmed until homogeneous and then stirred for 1.5 hr. The solvent was removed in vacuo and the residue taken up in water (50 mL). The aqueous solution was washed with Et$_2$O (30 mL) and then made acidic with 12 N HCl. The mixture was extracted with CHCl$_3$ (2×40 mL) and the combined extracts were dried (MgSO$_4$), filtered and evaporated in vacuo to give N-(3,5-dichlorophenylsulfonyl)-L-proline as a solid (3.37 g, 83%).

3,5-Dichlorophenyl-sulfonyl-L-proline was coupled to L-phenylalanine ethyl ester using the procedure described in Method 3 to give the ethyl ester of the title compound (348 mg, 45%).

The title compound was prepared via hydrolysis of the ethyl ester using NaOH in MeOH. NMR analysis indicated that diastereomers were present.

NMR data was as follows:

$^1$H NMR (CDCl$_3$): δ=8.11 (br s, 1H), 7.72 (d, 2H, J=1.9 Hz), 7.61 (q, 1H, J=2.0 Hz), 7.39–7.20 (6H), 4.92 (m, 1H), 4.15 (m, 1H), 3.52–3.09 (4H), 2.11 (m, 1H), 1.95–1.49 (3H).

$^{13}$C NMR (CDCl$_3$): δ=175.4, 175.2, 171.8, 171.7, 139.5, 139.3, 137.0, 136.6, 135.8, 134.0, 134.0, 129.9, 129.5, 127.7, 126.7, 111.4, 63.1, 62.9, 53.8, 53.6, 50.5, 50.3, 45.1, 37.9, 31.3, 30.8, 24.8, 24.6.

Mass Spectroscopy: FAB m/e 471 (M+H).

Example 55

Synthesis of N-(Toluene-4-sulfonyl)-L-prolyl-L-phenylalanine N-Hydroxysuccinimide ester Equimolar amounts of Cbz-L-phenylalanine, N-hydroxysuccinimide and DCC in CH$_2$Cl$_2$ were stirred for 3 hr at room temperature. Hexane was added and the reaction mixture filtered through a bed of Celite. The filtrate was extracted with 10% citric acid, water and saturated NaCl, dried over MgSO$_4$, filtered and concentrated to yield the title compound as a solid, mp=186–188° C.

NMR data was as follows:

$^1$H NMR (CDCl$_3$, 300 MHz): δ=7.66 (m, 3H); 7.28 (m, 6H); 4.64 (m, 1H); 4.01 (m, 1H); 3.36 (m, 1H); 2.89 (m, 6H); 2.42 (s, 3H); 1.90 & 1.68 (m, 3H); 1.33 & 1.15 (m, 4H).

$^{13}$C NMR (CDCl$_3$, 300 MHz): δ=173.07, 171.83, 166.89, 144.86, 137.90, 133.35, 130.51, 130.44, 129.06, 128.33, 127.36, 63.21, 50.12, 47.74, 45.09, 38.30, 36.53, 34.30, 30.67, 25.454, 24.35, 22.15.

Mass Spectroscopy: (+FAB) 528 (M+H).

Example 56

Synthesis of N-(Thiophene-2-sulfonyl)-L-prolyl-L-phenylalanine Methyl Ester

The title compound was prepared via Method 14 and isolated the as an oil.

NMR data was as follows:

$^1$H NMR (CDCl$_3$, 300 MHz): δ=7.63 (m, 1H); 7.32–7.10 (br m, 7H); 4.85 (m, 1H); 4.09 (m, 1H); 3.77 (s, 3H); 3.40 (m, 1H); 3.38 (m, 1H); 3.17 (m, 1H); 3.05 (m, 1H); 2.05 (m; 1H); 1.62–1.40 (br m, 3H).

$^{13}$C NMR (CDCl$_3$, 75 MHz): δ=171.9, 170.9, 136.6, 136.2, 133.9, 133.4, 129.8, 129.1, 128.3, 127.7, 63.2, 53.9, 53.1, 38.4, 30.1, 24.8.

Mass Spectroscopy: (PI-FAB) 423, (M+H)$^+$.

Example 57

Synthesis of N-(Thiophene-2-sulfonyl)-L-prolyl-L-phenylalanine

The title compound was prepared from Example 56 (285) via Method 6 and the product was isolated as a solid.

NMR data was as follows:

$^1$H NMR (DMSO-d$_6$, 300 MHz): δ=8.14 (d, 1H, J=8.0 Hz); 8.02 (d, 1H, J=5.0 Hz); 7.70 (d, 1H, J=4.0 Hz); 7.25 (m, 6H); 4.51 (m, 1H); 4.05 (m, 1H); 3.40 (m, 1H); 3.40 (m, 1H); 3.20–2.90 (br m, 3H); 1.65–1.32 (br m, 4H).

$^{13}$C NMR (DMSO-d$_6$, 75 MHz): δ=172.9, 170.9, 137.8, 136.4, 134.1, 133.4, 129.7, 128.6, 128.5, 126.8, 62.1, 53.5, 49.7, 36.8, 30.7, 24.1.

Mass Spectroscopy: (PI-FAB) 409, (M+H)$^+$.

Example 58

Synthesis of N-(1,3-Dimethyl-5-chloropyrazole-4-sulfonyl)-L-prolyl-L-phenylalanine The title compound was prepared using Method 14 and Method 7, and the product was isolated as a white solid.

NMR data was as follows:

$^1$H NMR (CD$_3$OD, 300 MHz): δ=7.00–6.93 (br m, 5H); 4.21 (m, 1H); 3.96 (m, 1H); 3.59 (s, 3H); 3.16–3.03 (br m, 3H); 2.88 (m, 1H); 2.14 (s, 3H); 1.68 (m, 2H); 1.56–1.29 (br m, 2H).

$^{13}$C NMR (CD$_3$OD, 75 MHz): δ=177.9, 173.6, 150.9, 139.7, 131.8, 131.4, 129.9, 127.9, 115.3, 63.7, 57.6, 50.7, 39.4, 37.7, 32.6, 25.8, 14.9.

Mass Spectroscopy: (PI-FAB) 477, (M+H)$^+$.

Example 59

Synthesis of N-(1-Phenylethanesulfonyl)-L-prolyl-L-phenylalanine

PhCH$_2$CH$_2$SH was treated with Cl$_2$ in a rapidly stirred mixture of CHCl$_3$ and H$_2$O, and then the CHCl$_3$ layer was washed with 5% NaHSO$_3$ and sat. NaCl, dried with MgSO$_4$, filtered, and concentrated to give PhCH$_2$CH$_2$SO$_2$Cl. This product was treated with Pro-OtBu and Et$_3$N in CH$_2$Cl$_2$ to give, after aqueous workup, PhCH$_2$CH$_2$SO$_2$-Pro-OtBu. This product was treated with HCO$_2$H, and the mixture was evaporated to give PhCH$_2$CH$_2$SO$_2$-Pro-OH. This product was treated with HCl.Phe-OtBu, EDAC, HOBT, and Et$_3$N in CH$_2$Cl$_2$ to give, after aqueous workup and flash chromatography, PhCH$_2$CH$_2$SO$_2$-Pro-Phe-OtBu. This product was treated with HCO$_2$H, and the mixture was evaporated to give the title compound as a clear oil.

NMR data was as follows:

$^1$H NMR (DMSO-d$_6$, 300 MHz): δ=8.06 (d, J=8.1, 1H), 7.32–7.14 (m, 10H), 4.52–4.24 (m, 1H), 4.26 (dd, J=7.0, J=2.6, 1H), 3.40–3.31 (m, 3H), 3.29–3.23 (m, 2H), 3.08 (dd, J=13.8, J=4.8, 1H), 2.97–2.90 (m, 3H), 2.05–1.99 (m, 1H), 1.77–1.65 (m, 3H).

$^{13}$C NMR (DMSO-d$_6$, 75 MHz): δ=172.7, 171.4, 138.5, 137.4, 129.2, 128.6, 128.5, 128.1, 126.5, 126.4, 60.8, 53.1, 50.0, 48.6, 36.6, 30.9, 28.6, 24.2.

Mass Spectroscopy: (+FAB, 3-nitrobenzyl alcohol) 431 (MH+).

Example 60

Synthesis of N-(1-Methylimidazole-4-sulfonyl)-L-prolyl-L-phenylalanine Methyl Ester The title compound was prepared using Method 14 and was isolated as an oil.

NMR data was as follows:

$^1$H NMR (CDCl$_3$, 300 MHz): δ=7.55–7.40 (br m, 3H); 7.31–7.10 (br m, 5 H); 4.80 (m, 1H); 4.31 (m, 1H); 3.70 (s, 3H); 3.49–3.18 (br m, 3H); 3.05 (m, 1 H); 2.05 (m, 1H); 1.74 (m, 2 H); 1.41 (m, 1H).

$^{13}$C NMR (CDCl$_3$, 75 MHz): δ=172.0, 171.6, 140.1, 137.9, 136.8, 129.8, 129.0, 127.5, 126.1, 63.1, 53.9, 52.9, 50.3, 38.4, 34.6, 30.4, 24.9.

Mass Spectroscopy: (PI-FAB) 421, (M+H)$^+$.

Example 61

Synthesis of N-(1-Methylimidazole-4-sulfonyl)-L-prolyl-L-phenylalanine

The title compound was prepared from Example 60 (297) using Method 7 and was isolated as a white solid.

NMR data was as follows:

$^1$H NMR (DMSO-d$_6$, 300 MHz): δ=7.83 (d, 2H, J=9.0 Hz), 7.65 (d, 1H, J=5.0 Hz), 7.20–7.05 (br m, 5H), 4.14 (m, 1H); 3.94 (m, 1H); 3.67 (s, 3H); 3.04 (m, 4H), 1.81 (m, 1H), 1.50 (m, 2H); 1.29 (m, 1H).

$^{13}$C NMR (DMSO-d$_6$, 75 MHz): δ=173.1, 169.9, 140.7, 139.2, 136.0, 130.0, 127.8, 126.7, 125.9, 63.0, 55.1, 49.7, 36.8, 33.9, 30.5, 23.9.

Mass Spectroscopy: (PI-FAB) 429, (M +H)$^+$.

Example 62

Synthesis of N-(4-Amidinobenznesulfonyl)-L-prolyl-L-phenylalanine Methyl Ester

The title compound was prepared by refluxing the product from Example 64 (313) (0.26 mmol) with ammonium acetate (0.32 mmol) in methanol (3 mL) for 3.5 hours and then concentrating under vacuum to give an oil (114 mg, 96%). The crude product was purified on silica gel chromatography (100% EtOAc, Rf=0.01) to yield a colorless oil (40 mg, 34%).

NMR data was as follows:

$^1$H NMR (CD$_3$OD, 300 MHz): δ=7.77 (m, 4 H); 7.07 (m, 5H); 4.48 (m, 1H); 4.01 (m, 1H); 3.51 (s, 3H); 3.25 (m, 1H); 3.04 (m, 3H); 2.85 (m, 1H); 1.50 (m, 4H).

$^{13}$C NMR (CD$_3$OD, 300 MHz): δ=174.45, 173.58, 168.09, 143.77, 138.72, 134.54, 131.01, 130.84, 130.16, 130.11, 128.57, 63.71, 55.72, 53.45, 51.09 38.72, 32.61, 25.97.

Mass Spectroscopy: (+FAB) 459 (M+H).

Example 63

Synthesis of N-(4-Amidinobenzenesulfonyl)-L-prolyl-L-phenylalanine

The title compound was prepared from the product of Example 62 (303) using the procedure described in Method 7.

NMR data was as follows:

$^1$H NMR (CD$_3$OD, 300 MHz): δ=7.72 (m, 4H); 7.00 (m, 5H); 4.51 (m, 0.5 H); 4.20 (t, 1H, J=5.92); 3.93 (m, 1H); 3.23 (m, 0.5H); 3.14 (s, 1H); 3.04 (m, 1H); 2.85 (m, 1H); 1.48 (m, 4H).

$^{13}$C NMR (CD$_3$OD, 300 MHz): δ=178.07, 173.31, 141.62, 141.36, 139.70, 138.57, 131.36, 131.05, 131.00, 130.21, 130.17, 130.13, 130.02, 129.92, 129.78, 129.71, 128.60, 128.03, 64.12, 57.64, 51.20, 39.52, 32.36, 25.88.

Mass Spectroscopy: (+FAB) 467 (M+H), 489 (M+Na).

Example 64

Synthesis of N-(4-Thiomethoxyimidatylbenzenesulfonyl)-L-prolyl-L-phenylalanine Methyl Ester The title compound was prepared by refluxing the product from Example 65 (314) (0.20 mmoles) with acetone (3 mL) and methyl iodide (0.2 mL) for 30 minutes, and concentrating the reaction under vacuum to yield a yellow oil (130 mg, <100%). The crude product was purified on silica gel chromatography (80% EtOAc/Hexane, Rf=0.49) to yield a yellow oil (110 mg, 99%).

NMR data was as follows:

$^1$H NMR (CDCl$_3$, 300 MHz): δ=9.37 (bs, 2H); 8.11 (d, 2H, J=8.43 Hz); 7.96 (d, 2H, J=8.49 Hz); 7.20 (m, 6H); 4.82 (m, 1H); 4.11 (m, 1H); 3.74 (s, 3H); 3.41 (m, 1H); 3.23 (m, 1H); 3.09 (m, 2H); 2.94 (s, 3H), 1.83 (m, 1H); 1.62 (m, 3H).

$^{13}$C NMR (CDCl$_3$, 300 MHz): δ=186.47, 172.23, 171.65, 141.68, 136.53, 136.04, 130.32, 129.84, 129.16, 129.12, 127.74, 62.98, 53.98, 53.33, 50.48, 38.21, 31.58, 31.15, 24.83, 18.30.

Mass Spectroscopy: (+FAB) 490 (M+H).

Example 65

Synthesis of N-[4-(N-Methyl) thioamidobenzenesulfonyl]-L-prolyl-L-phenylalanine Methyl Ester The title compound was prepared by bubbling hydrogen sulfide through a solution of the methyl ester of Example 29 (71) (0.3 mmoles) in pyridine (3 mL) and triethylamine (0.3 mL) at room temperature for 5 minutes. The flask was sealed and the reaction stirred at room temperature for 18 hours. The reaction mixture was concentrated under a stream of nitrogen. The residue was diluted with EtOAc (100 mL) and successively washed with 2N KHSO$_4$ (2×50 mL) and saturated NaCl (50 mL), dried over MgSO$_4$, filtered and rotoevaporated to yield a yellow oil (146 mg, 100%). Silica gel TLC in 80% EtOAc/Hexane showed a single spot, Rf=0.06.

NMR data was as follows:

$^1$H NMR (CDCl$_3$, 300 MHz): δ=8.13 (d, 2H, J=11.54 Hz); 7.94 (d, 2H, J=8.37 Hz); 7.69 (d, 2H, J=8.43 Hz); 7.20 (m, 6H); 4.83 (m, 1H); 3.99 (d, 1H, J=6.17 Hz); 3.77 (s, 3H); 3.34 (t, 1H, J=6.59 Hz); 3.25 (m, 1H); 3.03 (m, 1H); 1.87 (m, 1H); 1.45 (m, 5H).

$^{13}$C NMR (CDCl$_3$, 300 MHz): δ=201.09, 172.29, 171.28, 144.50, 138.26, 136.37, 129.76, 129.21, 128.71, 128.21, 127.82, 62.92, 53.74, 53.31, 50.20, 38.37, 30.64, 30.54, 24.68, 21.68.

Mass Spectroscopy: (+FAB) 476 (M+H).

Example 66

Synthesis of N-(Toluene-4-sulfonyl)-L-prolyl-D,L-β-(1,2,4-triazol-3-yl)alanine An equimolar solution of β-(1,2,4-triazol-3-yl)-D,L-alanine methyl ester, N-(toluene-4-sulfonyl)]-L-proline hemibenzenate and benzotriazol-1-yloxytris (dimethylamino)phosphonium hexafluorophosphate with three equivalents of triethyl amine in acetonitrile (0.45M) was stirred at ambient temperature, under nitrogen, for 16 hr. The solvent was stripped off giving a dark reddish colored oil. The oil was dissolved in ethyl acetate and washed with copious amounts of water, brine, and saturated sodium bicarbonate solution and once again with water. The organic phase was dried (Na$_2$SO$_4$) and the solvent stripped off yielding a brown oil. The oil was hydrolyzed following the procedure described in Method 7 yielding the title compound as a beige solid, mp=153–163° C.

NMR data was as follows:

$^1$H NMR (DMSO-d$_6$, 400 Mhz): δ=8.29 (s, 1H); 7.77 (s, 1H); 7.57–7.52 (m, 2H); 7.37 (d, 1H, J=8.1 Hz); 7.32–7.29 (m, 2H); 7.22–7.19 (m, 1H); 4.40 (dd, 1H, J=9.9 Hz, 4.2 Hz); 4.29–4.25 (m, 1H); 3.95–3.87 (m, 1H); 3.82–3.77 (m, 1H); 3.15–3.06 (m, 1H); 2.96–2.85 (m, 1H); 2.61–2.56 (m, 1H); 2.27 (s, 1H); 2.22 (s, 1H); 1.81 (t, 1H, J=7.7 Hz); 1.75 (s, 3H); 1.75–1.50 (m, 1H); 1.17–1.15 (m, 1H); 1.05–0.94 (m, 1H); 0.92–0.89 (m, 1H).

IR (KBr, cm-1): 3400; 2960; 2850; 2500; 1775; 1600; 1450; 1400; 1200; 1175; 1050; 1025; 875; 830; 775; 700; 600; 575; 550.

Mass Spectroscopy: (+FAB) 428.3 (M+Na); 406.3 (M−H); 319.4; 269.4; 227.4; 205.4; 173.3; 113.12.

Example 67

Synthesis of N-(Toluene-4-sulfonyl)-L-prolyl-D,L-β-(2-thiazolyl)alanine

The methyl ester of the title compound was prepared using the procedure described in Method 3. The ester was hydrolyzed following the procedure described in Method 6 to afford the title compound as a foam.

NMR data was as follows:

$^1$H NMR (DMSO-d$_6$, 400 MHz): δ=8.36 (d, 0.5H, J=8 Hz); 8.24 (d, 0.5H, J=8 Hz); 7.7 (m, 3H); 7.58 (d, 1H, J=3 Hz); 7.4, (m, 2H); 4.65 (m, 1H); 4.14 (m, 0.5H); 4.1 (m, 0.5H); 3.45 (m, 8H); 3.1 (m, 1H); 2.39 (s, 3H); 1.75–1.4 (brd m, 4H).

IR (KBr, cm$^{-1}$): 3425, 2900, 1730, 1660, 1625, 1525, 1510, 1440, 1340, 1160, 1080, 660, 580,550.

Mass Spectroscopy: (+FAB) 424 ([M+H]$^+$); 323; 279; 237; 215; 197; 181; 149; 131; 109.

HPLC (Primesphere C-18; 40/60 methanol/0.01 M KH2PO4 buffer pH=3.5; flow rate=1 ml/min): 16.6 min retention time diasteomer A (49%); 19.1 min retention time diasteomer B (51%).

Example 68

Synthesis of N-[4-(3-Dimethylaminopropyloxy)-benzenesulfonyl]-L-prolyl-L-phenylalanine 4-(Methoxy)benzenesulfonyl chloride was dissolved in CH$_2$Cl$_2$ and chilled in an ice bath to 0° C. To this solution was added the hydrochloride of Pro-Phe-OMe (1 eq.) and TEA (2.2 eq). The reaction was allowed to warm to room temperature and stirred overnight under a stream of $N_2$. The reaction mixture was then concentrated and the residue taken up in EtOAc and $H_2O$ and the organic phase was washed with sat. $NaHCO_3$ and brine, dried ($MgSO_4$), filtered, concentrated to a tacky solid and used without further purification. The solid product was treated with $BBr_3$ (1M in $CH_2Cl_2$, 3.0 eq., −78° C. for one hour then warmed to rt). The reaction was then chilled in an ice bath and quenched with water. Following concentration, the residue was taken-up in EtOAc and water. The organic phase was washed with brine, dried ($MgSO_4$), filtered and concentrated to a foam. The product was esterified with MeOH and HCl gas (0° C. to rt, 16 hours) and purified by column chromatography. This product was then added to a chilled (0° C.) THF solution of triphenylphosphine (1.10 eq), 3-dimethylmino-1-propanol (1.0 eq) and diethyl azodicarboxylate (1.10 eq). The reaction temperature was held at 0° C. for 30 minutes and then allowed to warm to room tempeture and stirred overnight. The reaction mixture was concentrated and taken-up in EtOAc and washed with sat. $NaHCO_3$. The product was than extracted with 0.2 N citric acid, and the aqueous phase washed with EtOAc. The aqueous phase was then made basic with solid $NaHCO_3$ and the product extracted with EtOAc. The organic phase was washed with brine, dried ($MgSO_4$), filtered and concentrated. The product was purified by preparative TLC. The hydrolysis was performed using Method 7 to yield the title compound as a mixture of diastereomers and was isolated as a white, hygroscopic solid.

NMR data was as follows:

$^1$H NMR (DMSO-$d_6$, 300 MHz): δ=7.76 (d, 2H, J=9.0 Hz); 7.74 (m, 1H; 7.15–7.10 (br m, 6 H); 4.07 (t, 2H, J=5.0 Hz); 3.90 (m, 2H); 3.21–2.85 (m, 4H); 2.37 (m, 2H); 2.37 (t, 2H, J=7.0 Hz); 2.13 (s, 6H); 1.85 (m, 2H); 1.69 (m, 1H); 1.50–1.25 (m, 3H).

$^{13}$C NMR (DMSO-$d_6$, 75 MHz): δ=172.3, 169.7, 162.6, 139.3, 130.3, 130.1, 130.1, 128.1, 127.9, 127.8, 125.9, 125.8, 115.3, 115.2, 66.7, 62.4, 55.8, 55.2, 49.3, 45.5, 36.96, 30.6, 27.0, 23.9.

Mass Spectroscopy: (PI-FAB) 548, (M−H+Na)$^+$.

Example 69

Synthesis of N-(4-Thiocarbamoylbenzenesulfonyl)-L-(5,5-dimethyl)thiaprolyl-L-phenylalanine Benzyl Ester The title compound was prepared following the procedure of Example 65 (314).

NMR data was as follows:

$^1$H NMR (CDCl$_3$): δ=8.48 (bs, 1H), 8.24 (bs, 1H), 8.00–7.97 (d, 2H), 7.78–7.75 (d, 2H), 7.29–7.09 (m, 10H), 5.12 (m, 2H), 4.48 (m, 1H), 4.49–4.46 (d, 1H), 4.33–4.30 (d, 1H), 3.09 (m, 2H), 1.03–0.99 (d, 6H), 3.91 (s, 1H).

$^1$H NMR (CDCl$_3$): δ=200.5, 171.6, 169.2, 144.3, 138.4, 136.2, 135.6, 130.0, 129.2, 128.8, 128.4, 127.8, 74.1, 68.1, 55.1, 54.1, 51.1, 38.5, 29.8, 24.2, 21.7.

Example 70

Synthesis of N-(4-Cyanobenzenesulfonyl)-L-(5,5-dimethyl)thiaprolyl-L-phenylalanine Benzyl Ester The title compound was prepared following the procedure outlined for the preparation of Example 29 (71).

NMR data was as follows:

$^1$H NMR (CDCl$_3$): δ=7.95–7.92 (d, 2H), 7.77–7.74 (d, 2H), 7.34–7.33 (m, 10H), 7.19–7.18 (m, 10H), 7.10–7.09 (m, 10H), 6.97–6.95 (d, 1H), 5.15 (m, 2H), 4.91 (m, 1H), 4.47 (s, 2H), 3.10 (m, 2H), 1.19–1.11 (2s, 6H).

$^{13}$C NMR (CDCl$_3$): δ=171.3, 168.4, 141.0, 136.3, 135.6, 133.7, 130.0, 129.2, 127.7, 117.8, 74.1, 68.0, 55.3, 53.86, 51.1, 38.7, 29.9, 24.4.

Example 71

Synthesis of N-(Toluene-4-sulfonyl)-L-(thiamorpholyl-3-carbonyl)-L-phenylalanine L-thiamorpholine-5-carboxylic acid was prepared by the method of Larsson and Carlson (*Acta Chemica Scan.* 48: 517–525 (1994)). N-(toluene-4-sulfonyl)-L-thiamorpholine-5-carboxylic acid was prepared using the procedure described in Method 1. The title compound was prepared according to the procedure described in Example 1 (9).

NMR data was as follows:

$^1$H NMR (CD$_3$OD): δ=7.49–7.04 (m, 9H), 4.62 (m, 1H), 4.47 (m, 1H), 3.88 (m, 1H), 3.12–2.36 (m, 5H), 2.18 (s, 3H), 2.18–1.92 (m, 5H).

$^{13}$C NMR (CD$_3$OD): δ=175.1, 174.8, 170.8, 170.7, 146.2, 146.1, 138.9, 138.5, 131.8, 131.1, 130.3, 129.1, 128.7, 57.0, 56.9, 55.7, 45.5, 45.2, 38.9, 38.5, 28.6, 28.1, 26.8, 26.9, 22.3.

Example 72

Synthesis of N-(Toluene-4-sulfonyl)-L-[(1,1-dioxo)thiamorpholyl-3-carbonyl]-L-phenylalanine The title compound was prepared from the product of Example 71 (500) using the procedure described by Larsson and Carlson (*Acta Chemica Scan.* 48, 522 (1994)).

NMR data was as follows:

$^1$H NMR (CD$_3$OD): δ=7.54 (m, 2H), 7.17–6.90 (m, 10H), 5.07 (m, 1H), 4.45 (m, 1H), 4.08 (m, 1H), 3.8–3.3 (m, 2H), 3.09–2.6 (m, 5H), 2.22 (s, 3H), 2.11 (s, 3H).

$^{13}$C NMR (CD$_3$OD): δ=175.1, 174.5, 168.5, 146.9, 139.5, 138.4, 137.8, 132.0, 131.1, 131.6, 130.2, 129.2, 128.8, 126.9, 62.6, 57.8, 57.6, 55.7, 55.5, 51.6, 51.4, 43.8, 43.6, 43.6, 38.7, 38.5, 22.2, 22.1.

Example 73

Synthesis of N-(Toluene-4-sulfonyl)-L-[(1,1-dioxo)thiamorpholyl-3-carbonyl]-L-phenylalanine Ethyl Ester The title compound was prepared following the procedure outlined for the preparation of Example 72 (501).

NMR data was as follows:

$^1$H NMR (CDCl$_3$): δ=7.72 (d, 1H), 7.63 (d, 1H), 7.35 (m, 7H), 7.13 (m, 2H), 6.80 (d, 0.5H), 6.69 (d, 0.5H), 5.13 (m, 0.5H), 5.00 (m, 0.5H), 4.89 (m, 0.5H), 4.77 (m, 0.5H), 4.21 (m, 2H), 3.99 (m, 1H), 3.19 (m, 2H), 3.02 (m, 2H), 2.88 (m, 2H), 2.44 (s, 3H), 1.25 (m, 3H).

$^{13}$C NMR (CDCl$_3$): δ=171.5, 171.4, 165.4, 165.1, 146.1, 136.1, 135.5, 131.2, 130.0, 130.0, 129.3, 129.2, 128.0, 127.8, 62.5, 62.4, 56.8, 56.6, 54.2, 53.9, 50.2, 49.9, 49.4, 49.3, 42.6, 42.3, 38.1, 37.8, 22.3, 14.7.

Example 74

Synthesis of N-(toluene-4-sulfonyl)-L-prolyl-L-phenylalanine 2-(1-methyl-1,4-dihydropyridinyl-3-amido)ethyl ester A solution of (S,S)-1-methyl-3-[2-(3-phenyl-2-{[(1-toluene-4-sulfonyl)-pyrrolidine-2-carbonyl]-amino}- propionyloxy)-ethylcarbamoyl]-pyridinium iodide (3.8 g) was prepared in nitrogen degassed water (1000 mL) and acetonitrile (55 mL). At ambient temperature, a mixture of $Na_2S_2O_4$ (2.82 g) and $NaHCO_3$ (2.268 g) was added at once and the reaction mixture stirred another 3 hours at room temperature while being exposed to a slow nitrogen throughput. Thereafter, the aqueous phase was extracted with chloroform (3×200 mL), and the organic extracts were combined, dried over $MgSO_4$, filtered and evaporated. The residue was flash chromatographed on 200 g silica gel. Elution with 2% methanol/chloroform gave 800 mg of the titled compound as a solid, mp=68–72° C.

Other compounds prepared by the methods described above include those set forth in Table II below:

TABLE II $$R^1-SO_2-N(R^2)-\underset{H}{\overset{R^3}{\underset{|}{C}}}-Q-\underset{R^5}{\overset{|}{CH}}-\overset{O}{\overset{\|}{C}}-R^{6'}$$

| $R^1$ | $R^2$ | $R^3$ | $R^5$ | $R^{6'}$ | Q = —C(O)$NR^7$—$R^7$ | Example No. |
|---|---|---|---|---|---|---|
| n-butyl | $R^2/R^3$ = cyclic 3 carbon atoms (L-pyrrolidinyl) | | —$CH_2$-φ | —OH | H | 75 |
| p-$CH_3$-φ- | $R^2/R^3$ = cyclic 3 carbon atoms (L-pyrrolidinyl) | | —$CH_2$-φ | —$NH_2$ | H | 76 |
| p-$CH_3$-φ- | $R^2/R^3$ = cyclic 3 carbon atoms (L-pyrrolidinyl) | | —$CH_2$-φ | —O-ethyl | H | 77 |
| p-$CH_3$-φ- | $R^2/R^3$ = cyclic 3 carbon atoms (L-pyrrolidinyl) | | —$CH_2$-φ | —O$CH_2$NC(O)φ \| EtOC(O)$CH_2$ | H | 78 |
| p-$CH_3$-φ- | $R^2/R^3$ = cyclic —$CH_2$S—C$(CH_3)_2$— (L-5,5-dimethylthiazolidin-4-yl) | | —$CH_2$-φ | —O$CH_2CH_3$ | H | 79 |
| p-$CH_3$-φ- | $R^2/R^3$ = cyclic —$CH_2$CH(O$CH_3$)$CH_2$— (3-methoxy-L-pyrrolidin-2-yl) | | —$CH_2$-φ | OH | H | 80 |
| p-$CH_3$-φ- | $R^2/R^3$ = cyclic 3 carbon atoms (L-pyrrolidinyl) | | —$CH_2$-φ | 2-β-isopropyl-4-α-methyl-cyclohex-1-oxy | H | 81 |
| p-$CH_3$-φ- | $R^2/R^3$ = cyclic 3 carbon atoms (L-pyrrolidinyl) | | —$CH_2$-φ | —O$CH_2CH_2$— NHC(O)- pyrid-3-yl | H | 82 |
| p-$CH_3$-φ- | $R^2/R^3$ = cyclic 3 carbon atoms (L-pyrrolidinyl) | | —$CH_2$-φ | —O$CH_2CH_2$— NHC(O)—N-methylpyrid-3-yl | H | 83 |
| p-$CH_3$-φ- | $R^2/R^3$ = cyclic 3 carbon atoms (L-pyrrolidinyl) | | —$CH_2$-φ | —O-cholest-5-en-3-β-yl | H | 84 |
| p-$CH_3$-φ- | $R^2/R^3$ = cyclic 3 carbon atoms (L-pyrrolidinyl) | | —$CH_2$-φ | —O$CH_2CH_2$— NHC(O)—N-methyl-1,4-dihydro-pyrid-3-yl | H | 85 |
| p-$CH_3$-φ- | $R^2/R^3$ = cyclic 3 carbon atoms (L-pyrrolidinyl) | | —$CH_2$-φ | —OH | Q = —C(S)NH— | 86 |
| p-$CH_3$-φ- | $R^2/R^3$ = cyclic 3 carbon atoms (L-pyrrolidinyl) | | —$CH_2$-φ | —OH | H | 87 |
| p-$CH_3$-φ- | $R^2/R^3$ = cyclic —$CH_2$—$CH_2$—C$(CH_3)_2$— (L-4,4-dimethylpyrrolidinyl) | | —$CH_2$-φ | —OH | H | 88 |
| p-$CH_3$-φ- | $R^2/R^3$ = cyclic —$CH_2$—$SO_2$—C$(CH_3)_2$— (L-1,1-dioxo-5,5-dimethylthiazolidin-4-yl) | | —$CH_2$-φ | —OH | H | 89 |
| p-$CH_3$-φ- | $R^2/R^3$ = cyclic 3 carbon atoms (L-pyrrolidinyl) | | —$CH_2$-φ | —OC$(CH_3)_3$ | H | 90 |
| p-$CH_3$-φ- | $R^2/R^3$ = cyclic 3 carbon atoms (L-pyrrolidinyl) | | —$CH_2$-φ | —O$CH_3$ | Q = —C(S)NH— | 91 |
| φ- | $R^2/R^3$ = cyclic 3 carbon atoms (L-pyrrolidinyl) | | —$CH_2$-φ | —O$CH_3$ | H | 92 |

TABLE II-continued $$R^1\text{---}SO_2\text{---}N(R^2)\text{---}\underset{H}{\overset{R^3}{\underset{|}{\overset{|}{C}}}}\text{---}Q\text{---}\underset{R^5}{\overset{|}{CH}}\text{---}\overset{O}{\overset{\|}{C}}\text{---}R^{6'}$$

| $R^1$ | $R^2$ | $R^3$ | $R^5$ | $R^{6'}$ | Q = —C(O)NR$^7$—R$^7$ | Example No. |
|---|---|---|---|---|---|---|
| p-CH$_3$-φ- | $R^2/R^3$ = cyclic —C(O)—CH$_2$—CH$_2$— (L-5-oxopyrrolidinyl) | | —CH$_2$-φ | —OCH$_2$CH$_3$ | H | 93 |
| p-CH$_3$-φ- | $R^2/R^3$ = cyclic —C(O)—CH$_2$—CH$_2$— (L-5-oxopyrrolidinyl) | | —CH$_2$-φ | —OH | H | 94 |

Example 95

In vitro Assay For Determining Binding of Candidate Compounds to VLA-4

An in vitro assay was used to assess binding of candidate compounds to $\alpha_4\beta_1$ integrin. Compounds which bind in this assay can be used to assess VCAM-1 levels in biological samples by conventional assays (e.g., competitive assays). This assay is sensitive to IC$_{50}$ values as low as about 1 nM.

The activity of $\alpha_4\beta_1$ integrin was measured by the interaction of soluble VCAM-1 with Jurkat cells (e.g., American Type Culture Collection Nos. TIB 152, TIB 153, and CRL 8163), a human T-cell line which expresses high levels of $\alpha_4\beta_1$ integrin. VCAM-1 interacts with the cell surface in an $\alpha_4\beta_1$ integrin-dependent fashion (Yednock, et al. *J. Biol. Chem.* 270: 28740 (1995)).

Recombinant soluble VCAM-1 was expressed as a chimeric fusion protein containing the seven extracellular domains of VCAM-1 on the N-terminus and the human IgG$_1$ heavy chain constant region on the C-terminus. The VCAM-1 fusion protein was made and purified by the manner described by Yednock, supra.

Jurkat cells were grown in RPMI 1640 supplemented with 10% fetal bovine serum, penicillin, streptomycin and glutamine as described by Yednock, supra.

Jurkat cells were incubated with 1.5 mM MnCl$_2$ and 5 μg/mL 15/7 antibody for 30 minutes on ice. Mn$^{+2}$ activates the receptor to enhance ligand binding, and 15/7 is a monoclonal antibody that recognizes an activated/ligand occupied conformation of $\alpha_4\beta_1$ integrin and locks the molecule into this conformation, thereby stabilizing the VCAM-1/$\alpha_4\beta_1$ integrin interaction. Yednock, et al., supra. Antibodies similar to the 15/7 antibody have been prepared by other investigators (Luque, et al., *J. Biol. Chem.* 271:11067 (1996)) and may be used in this assay.

Cells were then incubated for 30 minutes at room temperature with candidate compounds, in various concentrations ranging from 66 μM to 0.01 μM using a standard 5-point serial dilution. 15 μL soluble recombinant VCAM-1 fusion protein was then added to Jurkat cells and incubated for 30 minutes on ice. (Yednock et al., supra.).

Cells were then washed two times and resuspended in PE-conjugated goat F(ab')$_2$ anti-mouse IgG Fc (Immunotech, Westbrook, Me.) at 1:200 and incubated on ice, in the dark, for 30 minutes. Cells were washed twice and analyzed with a standard fluorescence activated cell sorter ("FACS") analysis as described in Yednock, et al., supra.

Compounds having an IC$_{50}$ of less than about 15 μM possess binding affinity to (X4P$_1$ When tested in this assay, each of the compounds in Examples 1–91 has an IC$_{50}$ of 15 μM or less.

Example 96

In vitro Saturation Assay For Determining Binding of Candidate Compounds to $\alpha_4\beta_1$ The following describes an in vitro assay to determine the plasma levels needed for a compound to be active in the Experimental Autoimmune Encephalomyelitis ("EAE") model, described in the next example, or in other in vivo models.

Log-growth Jurkat cells are washed and resuspended in normal animal plasma containing 20 μg/ml of the 15/7 antibody (described in the above example).

The Jurkat cells are diluted two-fold into either normal plasma samples containing known candidate compound amounts in various concentrations ranging from 66 μM to 0.01 μM, using a standard 12 point serial dilution for a standard curve, or into plasma samples obtained from the peripheral blood of candidate compound-treated animals.

Cells are then incubated for 30 minutes at room temperature and washed twice with phosphate-buffered saline ("PBS") containing 2% fetal bovine serum and 1 mM each of calcium chloride and magnesium chloride (assay medium) to remove unbound 15/7 antibody.

The cells are then exposed to phycoerythrin-conjugated goat F(ab')$_2$ anti-mouse IgG Fc (Immunotech, Westbrook, Me.), which has been adsorbed for any non-specific cross-reactivity by co-incubation with 5% serum from the animal species being studied, at 1:200 and incubated in the dark at 4° C. for 30 minutes.

Cells are washed twice with assay medium and resuspended in the same. They are then analyzed with a standard fluorescence activated cell sorter ("FACS") analysis as described in Yednock et al., *J. Biol. Chem.* 270: 28740 (1995).

The data is then graphed as fluorescence versus dose, e.g., in a normal dose-response fashion. The dose levels that result in the upper plateau of the curve represent the levels needed to obtain efficacy in an in vivo model.

This assay may also be used to determine the plasma levels needed to saturate the binding sites of other integrins, such as the $\alpha_9\beta_1$ integrin, which is the integrin most closely related to $\alpha_4\beta_1$ (Pahner et al., *J. Cell Bio.* 123: 1289 (1993)). Such binding is predictive of in vivo utility for inflammatory conditions mediated by $\alpha_9\beta_1$ integrin, including, by way of example, airway hyper-responsiveness and occlusion that occurs with chronic asthma, smooth muscle cell proliferation in atherosclerosis, vascular occlusion following angioplasty, fibrosis and glomerular scarring as a result of renal disease, aortic stenosis, hypertrophy of synovial membranes in rheumatoid arthritis, and inflammation and scarring that occur with the progression of ulcerative colitis and Crohn's disease.

Accordingly, the above-described assay may be performed with a human colon carcinoma cell line, SW 480 (ATTC #CCL228), transfected with cDNA encoding $\alpha_9$ integrin (Yokosaki et al., *J. Biol. Chem.* 269; 26691 (1994)), in place of the Jurkat cells, to measure the binding of the $\alpha_9\beta_1$ integrin. As a control, SW 480 cells which express other $\alpha$ and $\beta_1$ subunits may be used.

Accordingly, another aspect of this invention is directed to a method for treating a disease in a mammalian patient, which disease is mediated by $\alpha_9\beta_1$, and which method comprises administering to said patient a therapeutically effective amount of a compound of this invention. Such compounds are preferably administered in a pharmaceutical composition described herein above. Effective daily dosing will depend upon the age, weight and condition of the patient, which factors can be readily ascertained by the attending clinician. However, in a preferred embodiment, the compounds are administered from about 20 to 500 µg/kg per day.

Example 97

In vivo Evaluation—Experimental Autoimmune Encephalomyelitis

The standard multiple sclerosis model, Experimental Autoimmune (or Allergic) Encephalomyelitis ("EAE"), was used to determine the effect of candidate compounds to reduce motor impairment in rats or guinea pigs. Reduction in motor impairment is based on blocking adhesion between leukocytes and the endothelium and correlates with anti-inflammatory activity in the candidate compound. This model has been previously described by Keszthelyi et al., *Neurology* 47:1053–1059 (1996), and measures the delay of onset of disease.

Brains and spinal cords of adult Hartley guinea pigs were homogenized in an equal volume of phosphate-buffered saline. An equal volume of Freund's complete adjuvant (100 mg *mycobacterium tuberculosis* plus 10 ml Freund's incomplete adjuvant) was added to the homogenate. The mixture was emulsified by circulating it repeatedly through a 20 ml syringe with a peristaltic pump for about 20 minutes.

Female Lewis rats (2–3 months old, 170–220 g) or Hartley guinea pigs (20 day old, 180–200 g) were anesthetized with isoflurane and three injections of the emulsion, 0.1 ml each, were made in each flank. Motor impairment onset is seen in approximately 9 days.

Candidate compound treatment began on Day 8, just before onset of symptoms. Compounds were administered subcutaneously ("SC"), orally ("PO") or intraperitoneally ("IP"). Doses were given in a range of 10 mg/kg to 200 mg/kg, bid, for five days, with typical dosing of 10 to 100 mg/kg SC, 10 to 50 mg/kg PO, and 10 to 100 mg/kg IP.

Antibody GG5/3 against $\alpha_4\beta_1$ integrin Keszthelyi et al., *Neurology* 47:1053–1059 (1996)), which delays the onset of symptoms, was used as a positive control and was injected subcutaneously at 3 mg/kg on Day 8 and 11.

Body weight and motor impairment were measured daily. Motor impairment was rated with the following clinical score:

| 0 | no change |
|---|---|
| 1 | tail weakness or paralysis |
| 2 | hindlimb weakness |
| 3 | hindlimb paralysis |
| 4 | moribund or dead |

A candidate compound was considered active if it delayed the onset of symptoms, e.g., produced clinical scores no greater than 2 or slowed body weight loss as compared to the control.

When tested in this in vivo assay, at least the compound of Example 3 was active.

Example 98

In vivo Evaluation—Asthma

Inflammatory conditions mediated by $\alpha_4\beta_1$ integrin include, for example, airway hyper-responsiveness and occlusion that occurs with chronic asthma. The following describes an asthma model which can be used to study the in vivo effects of the compounds of this invention for use in treating asthma.

Following the procedures described by Abraham et al, *J. Clin. Invest.* 93:776–787 (1994) and Abraham et al, *Am J. Respir Crit Care Med.* 156:696–703 (1997), both of which are incorporated by reference in their entirety, compounds of this invention are formulated into an aerosol and administered to sheep which are hypersensitive to *Ascaris suum* antigen. Compounds which decrease the early antigen-induced bronchial response and/or block the late-phase airway response, e.g., have a protective effect against antigen-induced late responses and airway hyper-responsiveness ("AHR"), are considered to be active in this model.

Allergic sheep which are shown to develop both early and late bronchial responses to inhaled *Ascaris suum* antigen are used to study the airway effects of the candidate compounds. Following topical anesthesia of the nasal passages with 2% lidocaine, a balloon catheter is advanced through one nostril into the lower esophagus. The animals are then intubated with a cuffed endotracheal tube through the other nostril with a flexible fiberoptic bronchoscope as a guide.

Pleural pressure is estimated according to Abraham (1994). Aerosols (see formulation below) are generated using a disposable medical nebulizer that provides an aerosol with a mass median aerodynamic diameter of 3.2 µm as determined with an Andersen cascade impactor. The nebulizer is connected to a dosimeter system consisting of a solenoid valve and a source of compressed air (20 psi). The output of the nebulizer is directed into a plastic T-piece, one end of which is connected to the inspiratory port of a piston respirator. The solenoid valve is activated for 1 second at the beginning of the inspiratory cycle of the respirator. Aerosols are delivered at $V_T$ of 500 ml and a rate of 20 breaths/minute. A 0.5% sodium bicarbonate solution only is used as a control.

To assess bronchial responsiveness, cumulative concentration-response curves to carbachol can be generated according to Abraham (1994). Bronchial biopsies can be taken prior to and following the initiation of treatment and 24 hours after antigen challenge. Bronchial biopsies can be preformed according to Abraham (1994).

An in vitro adhesion study of alveolar macrophages can also be performed according to Abraham (1994), and a percentage of adherent cells is calculated.

Aerosol Formulation

A solution of the candidate compound in 0.5% sodium bicarbonate/saline (w/v) at a concentration of 30.0 mg/mL is prepared using the following procedure:

|

D. when $R^1$ is 4-methylphenyl, $R^2$ and $R^3$ together with the pendent nitrogen and carbon atoms form a pyrrolidin-2-yl ring, $R^5$ is D-benzyl and Q is —C(O)NH—, then $R^6$ is not —OCH$_2$CH$_3$;

E. when $R^1$ is 4-methylphenyl, $R^2$ and $R^3$ together with the pendent nitrogen and carbon atoms form a 5,5-dimethyl-1,1-dioxo-thiaprolyl ring, $R^5$ is benzyl and Q is —C(O)NH—, then $R^6$ is not —OC(CH$_3$)$_3$; and F. when $R^1$ is 4-dibenzofuran or 7-nitro-2-dibenzofuran, $R^2$ and $R^3$ together with the pendent nitrogen and carbon atoms form a pyrrolidin-2-yl ring, $R^5$ is methanol, benzyl, or 4-hydroxybenzyl, and Q is —C(O)NH—, then $R^6$ is not —OCH$_3$.

3. The compound according to claims 1 or 2, wherein $R^1$ is selected from the group consisting of aryl, substituted aryl, heterocyclic, substituted heterocylic, heteroaryl and substituted heteroaryl.

4. The compound according to claims 1 or 2, wherein $R^1$ is selected from the group consisting of 4-methylphenyl, methyl, benzyl, n-butyl, 4-chlorophenyl, 1-naphthyl, 2-naphthyl, 4-methoxyphenyl, phenyl, 2,4,6-trimethylphenyl, 2-(methoxycarbonyl)phenyl, 2-carboxyphenyl, 3,5-dichlorophenyl, 4-trifluoromethylphenyl, 3,4-dichlorophenyl, 3,4-dimethoxyphenyl, 4-(CH$_3$C(O)NH—)phenyl, 4-trifluoromethoxyphenyl, 4-cyanophenyl, isopropyl, 3,5-di-(trifluoromethyl)phenyl, 4-t-butylphenyl, 4-t-butoxyphenyl, 4-nitrophenyl, 2-thienyl, 1-N-methyl-3-methyl-5-chloropyrazol-4-yl, phenethyl, 1-N-methylimidazol-4-yl, 4-bromophenyl, 4-amidinophenyl, 4-methylamidinophenyl, 4-[CH$_3$SC(=NH)]phenyl, 5-chloro-2-thienyl, 2,5-dichloro-4-thienyl, 1-N-methyl-4-pyrazolyl, 2-thiazolyl, 5-methyl-1,3,4-thiadiazol-2-yl, 4-[H$_2$NC(S)]phenyl, 4-aminophenyl, 4-fluorophenyl, 2-fluorophenyl, 3-fluorophenyl, 3,5-difluorophenyl, pyridin-3-yl, pyrimidin-2-yl, and 4-(3'-dimethylamino-n-propoxy)-phenyl.

5. The compound according to claims 1 or 2, wherein $R^2$ and $R^3$ together with the nitrogen atom bound to the $R^2$ substituent and the carbon bound to the $R^3$ substituent form a heterocyclic or substituted heterocyclic group of 4 to 6 ring atoms having 1 to 2 heteroatoms in the ring selected from the group consisting of nitrogen, oxygen and sulfur, which ring is optionally substituted with 1 to 2 substituents selected from the group consisting of fluoro, methyl, hydroxy, amino, phenyl, thiophenyl and thiobenzyl, or can be fused to another saturated heterocyclic or cycloalkyl ring such as a cyclohexyl ring to provide for a fused ring heterocycle of from 10 to 14 ring atoms having 1 to 2 heteroatoms in the ring selected from the group consisting of nitrogen, oxygen and sulfur.

6. A compound according to claims 1 or 2, wherein the $R^2$ and $R^3$ heterocyclic ring is selected from the group consisting of azetidin-2-yl, thiazolidin-4-yl, piperidin-2-yl, piperizin-2-yl, thiomorpholin-3-yl and pyrrolidin-2-yl.

7. The compound according to claims 1 or 2, wherein the $R^2$ and $R^3$ substituted heterocyclic ring is selected from the group consisting of 4-hydroxypyrrolidin-2-yl, 4-fluoropyrrolidin-2-yl, 3-phenylpyrrolidin-2-yl, 3-thiophenylpyrrolidin-2-yl, 4-aminopyrrolidin-2-yl, 3-methoxypyrrolidin-2-yl, 4,4-dimethylpyrrolidin-2-yl, 4-N-Cbz-piperizin-2-yl, 5,5-dimethylthiazolidin-4-yl, 1,1-dioxo-thiazolidin-4-yl, L-1,1-dioxo-5,5-dimethylthiazolidin-4-yl and 1,1-dioxothiomorpholinyl.

8. The compound according to claims 1 or 2, wherein $R^5$ is selected from the group consisting of benzyl, phenethyl, —CH$_2$-(3-indolyl), —CH$_2$-(1-naphthyl), —CH$_2$-(2-naphthyl), —CH$_2$-(2-thienyl), —CH$_2$-(3-pyridyl), —CH$_2$-(5-imidazolyl), —CH$_2$-3-(1,2,4-triazolyl) and —CH$_2$-(2-thiazolyl).

9. The compound according to claim 2, wherein $R^6$ is selected from the group consisting of methoxy, ethoxy, iso-propoxy, n-butoxy, t-butoxy, cyclopentoxy, neo-pentoxy, 2-α-iso-propyl-4-β-methylcyclohexoxy, 2-β-isopropyl-4-β-methylcyclohexoxy, —NH$_2$, benzyloxy, —NHCH$_2$COOH, —NHCH$_2$CH$_2$COOH, —NH-adamantyl, —NHCH$_2$CH$_2$COOCH$_2$CH$_3$, —NHSO$_2$-p-CH$_3$-φ, —NHOR$^8$ where $R^8$ is hydrogen, methyl, iso-propyl or benzyl, O-(N-succinimidyl), —O-cholest-5-en-3-β-yl, —OCH$_2$—OC(O)C(CH$_3$)$_3$, —O(CH$_2$)$_z$NHC(O)W where z is 1 or 2 and W is selected from the group consisting of pyrid-3-yl, N-methylpyridyl, and N-methyl-1,4-dihydro-pyrid-3-yl and —NR"C(O)—R' where R' is aryl, heteroaryl or heterocyclic and R" is hydrogen or —CH$_2$C(O)OCH$_2$CH$_3$.

10. A compound selected from the group consisting of:
N-(methanesulfonyl)-L-prolyl-L-phenylalanine
N-(α-toluenesulfonyl)-L-prolyl-L-phenylalanine
N-(toluene-4-sulfonyl)-L-prolyl-L-phenylalanine
N-(toluene-4-sulfonyl)-L-prolyl-L-(N-methyl) phenylalanine
N-(toluene-4-sulfonyl)-L-pipecolinyl-L-phenylalanine
N-(toluene-4-sulfonyl)-D-prolyl-L-phenylalanine
N-(toluene-4-sulfonyl)-L-(4-hydroxy)prolyl-L-phenylalanine
N-(toluene-4-sulfonyl)-L-prolyl-D,L-homophenylalanine
N-(4-chlorobenzenesulfonyl)-L-prolyl-L-phenylalanine
N-(1-naphthalenesulfonyl)-L-prolyl-L-phenylalanine
N-(2-naphthalenelsulfonyl)-L-prolyl-L-phenylalanine
N-(4-methoxybenzenesulfonyl)-L-prolyl-L-phenylalanine
N-(4-tert-butylbenzenesulfonyl)-L-prolyl-L-phenylalanine
N-(toluene-4-sulfonyl)-L-(4-fluoro)prolyl-L-phenylalanine
N-(n-butanesulfonyl)-L-prolyl-L-phenylalanine
N-(toluene-4-sulfonyl)-L-(5,5-dimethyl)thiaprolyl-L-phenylalanine
N-(2-methoxycarbonylbenzenesulfonyl)-L-prolyl-L-phenylalanine
N-(2-carboxybenzenesulfonyl)-L-prolyl-L-phenylalanine
N-(toluene-4-sulfonyl)-L-thiaprolyl-L-phenylalanine
N-(3,5-dichlorobenzenesulfonyl)-L-prolyl-L-phenylalanine
N-(4-trifluoromethoxybenzenesulfonyl)-L-prolyl-L-phenylalanine
N-(3,4-dichlorobenzenesulfonyl)-L-prolyl-L-phenylalanine
N-(toluene-4-sulfonyl)-D,L-(3-phenyl)prolyl-L-phenylalanine
N-(3,4-dimethoxybenzenesulfonyl)-L-prolyl-L-phenylalanine
N-(4-nitrobenzenesulfonyl)-L-prolyl-L-phenylalanine
N-(4-acetamidobenzenesulfonyl)-L-prolyl-L-phenylalanine
N-(4-cyanobenzenesulfonyl)-L-prolyl-L-phenylalanine
N-(toluene-4-sulfonyl)-L-prolyl-L-tryptophan
N-(toluene-4-sulfonyl)-L-prolyl-β-(1-naphthyl)-L-alanine
N-(toluene-4-sulfonyl)-L-prolyl-β-(2-naphthyl)-L-alanine
N-(toluene-4-sulfonyl)-L-prolyl-β-(2-thienyl)-L-alanine
N-(isopropanesulfonyl)-L-prolyl-L-phenylalanine
N-(toluene-4-sulfonyl)-L-prolyl-β-(3-pyridyl)-L-alanine
N-(toluene-4-sulfonyl)-L-(4-phenylthio)prolyl-L-phenylalanine
N-(toluene-4-sulfonyl)-(4-benzylthio)-L-prolyl-L-phenylalanine
N-(toluene-4-sulfonyl)-L-prolyl-L-histidine
N-(toluene-4-sulfonyl)-L-(4-amino)prolyl-L-phenylalanine
N-(toluene-4-sulfonyl)-L-prolyl-L-phenylalaninamide
N-(toluene-4-sulfonyl)-L-prolyl-L-phenylalanine benzyl ester N-(toluene-4-sulfonyl)-L-prolyl-L-phenylalanine ethyl ester
N-(toluene-4-sulfonyl)-L-prolyl-L-phenylalanine N-methoxyamide
N-(toluene-4-sulfonyl)-L-prolyl-L-phenylalanine N-benzyloxyamide
N-(toluene-4-sulfonyl)-L-prolyl-L-phenylalanine N-(toluene4-sulfonyl)amide
N-(toluene-4-sulfonyl)-L-prolyl-L-phenylalaninyl-β-alanine
N-(toluene-4-sulfonyl)-L-prolyl-L-phenylalanine N-hydroxyamide
N-(toluene-4-sulfonyl)-L-prolyl-L-phenylalanine isopropyl ester
N-(toluene-4-sulfonyl)-L-(4-hydroxy)prolyl-L-phenylalanine
N-(toluene-4-sulfonyl)-L-prolyl-L-phenylalaninyl-(N-benzoyl)glycine ethyl ester
N-(toluene-4-sulfonyl)-L-(4-fluoro)prolyl-L-phenylalanine benzyl ester
N-(toluene-4-sulfonyl)-L-thiaprolyl-L-phenylalanine benzyl ester
N-(toluene-4-sulfonyl)-L-(5,5-dimethyl)thiaprolyl-L-phenylalanine benzyl ester
N-(toluene-4-sulfonyl)-L-(5,5-dimethyl)thiaprolyl-L-phenylalanine ethyl ester
N-(2-methoxycarbonylbenzenesulfonyl)-L-prolyl-L-phenylalanine benzyl ester
N-(toluene-4-sulfonyl)-L-(3-phenyl)prolyl-L-phenylalanine ethyl ester
N-(toluene-4-sulfonyl)-L-(4-methoxy)prolyl-L-phenylalanine
N-(toluene-4-sulfonyl)-L-prolyl-L-phenylalanine (1S,2R, 5S)-(+)-menthyl ester
N-(toluene-4-sulfonyl)-L-prolyl-L-phenylalanine N-hydroxysuccinimide ester
N-(toluene-4-sulfonyl)-L-prolyl-L-phenylalanine 2-(nicotinamido)ethyl ester
N-(toluene-4-sulfonyl)-L-prolyl-L-phenylalanine 2-(1-methylpyridinium-3-amido)ethyl ester
N-(toluene-4-sulfonyl)-L-prolyl-L-phenylalanine cholesteryl ester
N-(toluene-4-sulfonyl)-L-prolyl-L-phenylalanine 2-(1-methyl-1,4-dihydropyridinyl-3-amido)ethyl ester
N-(thiophene-2-sulfonyl)-L-prolyl-L-phenylalanine methyl ester
N-(thiophene-2-sulfonyl)-L-prolyl-L-phenylalanine
N-(5-chloro-1,3-dimethylpyrazole-4-sulfonyl)-L-prolyl-L-phenylalanine
N-(2-phenylethanesulfonyl)-L-prolyl-L-phenylalanine
N-(1-methylimidazole-4-sulfonyl)-L-prolyl-L-phenylalanine methyl ester
N-(1-methylimidazole-4-sulfonyl)-L-prolyl-L-phenylalanine
N-(4-amidinobenzenesulfonyl)-L-prolyl-L-phenylalanine methyl ester
N-(4-amidinobenzenesulfonyl)-L-prolyl-L-phenylalanine
N-(4-thiomethoxyimidatylbenzene-4-sulfonyl)-L-prolyl-L-phenylalanine methyl ester
N-[4-(N-methylthioamido)benzenesulfonyl]-L-prolyl-L-phenylalanine methyl ester
N-(toluene-4-sulfonyl)-L-prolyl-D,L-β-(1,2,4-triazol-3-yl) alanine
N-(toluene-4-sulfonyl)-L-prolyl-D,L-β-(thiazol-2-yl) alanine
N-[4-(3-dimethylaminopropyloxy)benzenesulfonyl]-L-prolyl-L-phenylalanine
N-(toluene-4-sulfonyl)-L-pyrrolidin-2-yl-thiocarbonyl-L-phenylalanine
N-(4-thiocarbamoylbenzenesulfonyl)-L-(5,5-dimethyl) thiaprolyl-L-phenylalanine benzyl ester
N-(4-cyanobenzenesulfonyl)-L-(5,5-dimethyl)thiaprolyl-L-phenylalanine benzyl ester
N-(toluene-4-sulfonyl)-L-prolyl-D-phenylalanine
N-(toluene-4-sulfonyl)-L-(thiamorpholin-3-carbonyl)-L-phenylalanine
N-(toluene-4-sulfonyl)-[(1,1-dioxo)thiamorpholin-3-carbonyl]-L-phenylalanine
N-(toluene-4-sulfonyl)-L-(3,3-dimethyl)prolyl-L-phenylalanine
N-(toluene-4-sulfonyl)-L-(5,5-dimethyl-1,1-dioxo) thiaprolyl-L-phenylalanine
N-(toluene-4-sulfonyl)-[(1,1-dioxo)thiamorpholin-3-carbonyl]-L-phenylalanine ethyl ester
N-(toluene-4-sulfonyl)-L-prolyl-L-phenylalanine tert-butyl ester
N-(toluene-4-sulfonyl)-L-pyrrolidin-2-yl-thiocarbonyl-L-phenylalanine methyl ester
N-(benzenesulfonyl)-L-prolyl-L-phenylalanine methyl ester
N-(toluene-4-sulfonyl)-L-(5-oxo)prolyl-L-phenylalanine ethyl ester
N-(toluene-4-sulfonyl)-L-(5-oxo)prolyl-L-phenylalanine
and pharmaceutically acceptable salts thereof as well as any of the ester compounds recited above wherein one ester is replaced with another ester selected from the group consisting of methyl ester, ethyl ester, n-propyl ester, isopropyl ester, n-butyl ester, isobutyl ester, sec-butyl ester and tert-butyl ester.

11. A method for binding VLA-4 in a biological sample which method comprises contacting the biological sample with a compound according to claim 1 or 2 under conditions wherein said compound binds to VLA-4.

12. A pharmaceutical composition comprising a pharmaceutically acceptable carrier and a therapeutically effective amount of one or more of the compounds of claims 1 or 2.

13. A method for the treatment of an inflammatory disease in a patient mediated by VLA-4 which method comprises administering to the patient the pharmaceutical composition of claim 12.

14. The method according to claim 13 wherein said inflammatory disease is selected from the group consisting of asthma, Alzheimer's disease, atherosclerosis, AIDS dementia, diabetes (including acute juvenile onset diabetes), inflammatory bowel disease (including ulcerative colitis and Crohn's disease), multiple sclerosis, rheumatoid arthritis, tissue transplantation, tumor metastasis, meningitis, encephalitis, stroke and other cerebral traumas, nephritis, retinitis, atopic dermatitis, psoriasis, myocardial ischemia and acute leukocyte-mediated lung injury such as that which occurs in adult respiratory distress syndrome.

15. The method according to claim 14 wherein said inflammatory disease is asthma.

16. A compound of formula III:

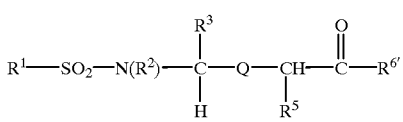

wherein:
$R^1$ is selected from the group consisting of alkyl, substituted alkyl, aryl, substituted aryl, cycloalkyl, heterocyclic, substituted heterocyclic, heteroaryl and substituted heteroaryl;

R² and R³, together with the nitrogen atom bound to R² and the carbon atom bound to R³, form a saturated heterocyclic group or a saturated substituted heterocyclic group wherein said saturated heterocyclic group or saturated substituted heterocyclic group is selected to form a thiazolin-4-yl group, with the proviso that when monosubstituted, the substituent on said saturated heterocyclic group is not carboxyl;

R⁵ is selected from the group consisting of —(CH₂)ₙ-aryl and —(CH₂)ₙ-heteroaryl, where n is an integer equal to 1 to 4;

R⁶' is selected from the group consisting of hydroxy, amino, alkoxy, substituted alkoxy, cycloalkoxy, substituted cycloalkoxy, —O-(N-succinimidyl), —NH-adamantyl, —O-cholest-5-en-3-β-yl, —NHOY where Y is hydrogen, alkyl, substituted alkyl, aryl, and substituted aryl, —NH(CH₂)ₚCOOY where p is an integer of from 1 to 8 and Y is as defined above, —OCH₂NR⁹R¹⁰ where R⁹ is selected from the group consisting of —C(O)-aryl and —C(O)-substituted aryl and R¹⁰ is selected from the group consisting of hydrogen and —CH₂COOR¹¹ where R¹¹ is alkyl, and —NHSO₂Z where Z is alkyl, substituted alkyl, cycloalkyl, substituted cycloalkyl, aryl, substituted aryl, heteroaryl, substituted heteroaryl, heterocyclic and substituted heterocyclic;

Q is —C(X)NR⁷— wherein R⁷ is selected from the group consisting of hydrogen and alkyl, and X is selected from the group consisting of oxygen and sulfur;

and pharmaceutically acceptable salts thereof;

with the following proviso:
when R¹ is 4-methylphenyl, R² and R³ together with the pendent nitrogen and carbon atoms form a 5,5-dimethyl-1,1-dioxo-thiaprolyl ring, R⁵ is benzyl and Q is —C(O)NH—, then R⁶' is not —OC(CH₃)₃.

17. The compound according to claim 16, wherein the R² and R³ substituted heterocyclic ring is selected from the group consisting of 5,5-dimethyl-thaizolidin-4-yl, 1,1-dioxo-thiazolidin-yl, and L-1,1-dioxo-5,5-dimethylthiazolidin-4-yl.

18. The compound according to claim 16, selected from the group consisting of:

N-(toluene-4-sulfonyl)-L-(5,5-dimethyl)thiaprolyl-L-phenylalanine

N-(toluene-4-sulfonyl)-L-thiaprolyl-L-phenylalanine

N-(toluene-4-sulfonyl)-L-thiaprolyl-L-phenylalanine benzyl ester

N-(toluene-4-sulfonyl)-L-(5,5-dimethyl)thiaprolyl-L-phenylalanine benzyl ester

N-(toluene-4-sulfonyl)-L-(5,5-dimethyl)thiaprolyl-L-phenylalanine ethyl ester

N-(4-thiocarbarnoylbenzenesulfonyl)-L-(5,5-dimethyl) thiaprolyl-L-phenylalanine benzyl ester N-(4-cyanobenzenesulfonyl)-L-(5,5-dimethyl)thiaprolyl-L-phenylalanine benzyl ester N-(toluene-4-sulfonyl)-L-(5,5-dimethyl-1,1-dioxo) thiaprolyl-L-phenylalanine;

and pharmaceutically acceptable accepted salts thereof.

* * * * *